United States Patent
Xu et al.

(10) Patent No.: US 9,861,703 B2
(45) Date of Patent: Jan. 9, 2018

(54) MULTI-TARGETED UBENIMEX PRODRUG DERIVATIVE AND PREPARATION METHOD AND USE THEREOF

(71) Applicant: Jinan Platinum Pharmatech Co. Ltd., Shandong (CN)

(72) Inventors: Wenfang Xu, Ji'nan (CN); Yuqi Jiang, Ji'nan (CN); Yingjie Zhang, Ji'nan (CN); Mingming Zou, Ganzhou (CN); Jinning Hou, Ji'nan (CN); Jin Li, Ji'nan (CN); Xuejian Wang, Weifang (CN); Xiaoyang Li, Ji'nan (CN)

(73) Assignee: Jinan Platinum Pharmatech Co. Ltd., Shandong (CN)

( * ) Notice: Subject to any disclaimer, the term of this patent is extended or adjusted under 35 U.S.C. 154(b) by 0 days.

(21) Appl. No.: 14/762,084

(22) PCT Filed: Jun. 6, 2014

(86) PCT No.: PCT/CN2014/079312
§ 371 (c)(1),
(2) Date: Jul. 20, 2015

(87) PCT Pub. No.: WO2014/194848
PCT Pub. Date: Dec. 11, 2014

(65) Prior Publication Data
US 2016/0193347 A1    Jul. 7, 2016

(30) Foreign Application Priority Data

Jun. 7, 2013 (CN) ............ 2013 1 0225754
Sep. 3, 2013 (CN) ............ 2013 1 0393152

(51) Int. Cl.
| | |
|---|---|
| A61K 38/00 | (2006.01) |
| A61K 47/00 | (2006.01) |
| A61K 47/48 | (2006.01) |
| A61K 31/553 | (2006.01) |
| C07D 239/553 | (2006.01) |
| C07D 417/12 | (2006.01) |
| C07D 309/14 | (2006.01) |
| C07C 275/64 | (2006.01) |
| A61K 31/17 | (2006.01) |
| A61K 31/198 | (2006.01) |
| A61K 31/506 | (2006.01) |
| A61K 31/513 | (2006.01) |
| A61K 31/704 | (2006.01) |
| A61K 38/05 | (2006.01) |
| A61K 47/55 | (2017.01) |

(52) U.S. Cl.
CPC ........... *A61K 47/481* (2013.01); *A61K 31/17* (2013.01); *A61K 31/198* (2013.01); *A61K 31/506* (2013.01); *A61K 31/513* (2013.01); *A61K 31/553* (2013.01); *A61K 31/704* (2013.01); *A61K 38/05* (2013.01); *A61K 47/55* (2017.08); *C07C 275/64* (2013.01); *C07D 239/553* (2013.01); *C07D 309/14* (2013.01); *C07D 417/12* (2013.01)

(58) Field of Classification Search
CPC .............................. A61K 38/00; A61K 47/00
See application file for complete search history.

(56) References Cited

U.S. PATENT DOCUMENTS

2008/0206917 A1    8/2008  Dast

FOREIGN PATENT DOCUMENTS

| | | |
|---|---|---|
| CN | 101531613 A | 9/2009 |
| CN | 103044437 A | 4/2013 |
| CN | 103588713 A | 2/2014 |
| JP | 2000327568 | 11/2000 |
| JP | 2001131066 A | 5/2001 |
| JP | 2009509151 | 3/2009 |

(Continued)

OTHER PUBLICATIONS

Mittwoch, MedChem5_lead, 2009, available online at http://www.chem.uzh.ch/zerbe/MedChem/MedChem5_Lead.pdf.*

(Continued)

*Primary Examiner* — Kaipeen Yang
(74) *Attorney, Agent, or Firm* — Calfee, Halter & Griswold LLP

(57) ABSTRACT

The present invention relates to the design, synthesis, and biological study of multi-targeted Ubenimex pro-drug derivative. More particularly, provided in the present invention is a compound as shown by general structural formula (I) (wherein the definition of R is shown in the description). The derivative is a multi-targeted compound obtained by binding an aminopeptidase (APN/CD13) inhibitor, Ubenimex, with some anti-tumor drugs already on the market through an ester bond or amide bond, and is suitable for use as an anti-tumor drug for the treating various malignant tumors, and is especially suitable for treating various solid tumors.

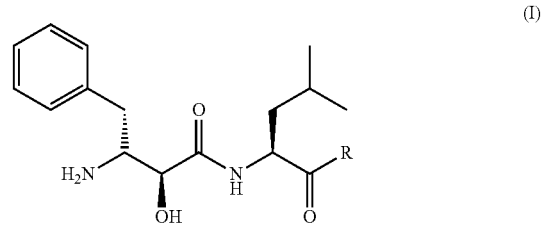

4 Claims, 7 Drawing Sheets

(56) References Cited

FOREIGN PATENT DOCUMENTS

JP          201356837   A    3/2013
WO         2013026942  A1   2/2013

OTHER PUBLICATIONS

Bis(2-chloroethyl)amine hydrochloride, Ningbo Taikang Chemical Co., Ltd., produced on Mar. 29, 2012.*
Chemical Book, CAS DataBase 821-48-7, available online at: http://www.chemicalbook.com/CASEN_821-48-7.htm, accessed on Mar. 3, 2017.*
International Search Report from PCT/CN2014/079312 dated Aug. 5, 2014.
Rawlings et al., MEROPS: the peptidase database, Nucleic Acids Res., 1999,27(1):325-331.
Breljak et al., The abstract of 'Haema.,2003,4(6):453-461', and the downloading website is http://www.journals.indexcopernicus.com/issue.php?id=6001&id_issue=568&id_lang=6.
Luan et al., The Structure and Main Functions of Aminopeptidase N, Current Medicinal Chemistry, 2007, 14, 639-647.
Guzman-Rojas et al., Cooperative effects of aminopeptidase N (CD13) expressed by nonmalignant and cancer cells within the tumor microenvironment, PNAS Jan. 31, 2012, 109, 1637-1642.
Haraguchi et al., CD13 is a therapeutic target in human liver cancer stem cells, J Clin Invest, Sep. 2010, 120, 3326-3339.
Aozuka et al., Anti-tumor angiogenesis effect of aminopeptidase inhibitor bestatin against B16-BL6 meanoma cells orthotopically implanted into syngeneic mice, Cancer let, 2004, 216(1):35-42.
Fuji et al., Inhibition of Tumor Cell Invasion and Matrix Degradation by Aminopeptidase Inhibitors, Bio. Pharm. Bull., 1996, 19(1):6-10.
Ogata-Ikeda et al., Cytotoxic action of bisabololoxide A German chamomile on human leukemia K562 cells in combination with 5-flourouracil, Phytomedicine 18 (2011) 362-365.
Lee et al., BMS-354825 potently inhibits multiple selected oncogenic tyrosine kinases prossesses broad-spectrum antitumor activities in vitro and in vivo, Proc Am Assoc Cancer Res, May 1, 2005, 46: 159.
Segler et al., Lenalidomide in solid tumors, Cancer Chemother Pharmacol.Jun. 2012;69(6):1393-406.
Itoh, Yukihiro et al., "Protein Knockdown Using Methyl Bestatin-Ligand Molecules: Design and Synthesis of Inducers of Ubiquitination-Mediated Degradation of Cellular Retinoic Acid-Binding Proteins," J. Am. Chem. Soc., vol. 132, 2010 pp. 5820-5826.
Das, N. et al., "Codrug: An Efficient Approach for Drug Optimization," European Journal of Pharmaceutical Sciences, vol. 41, 2010, pp. 571-588.
European Search Report to European Patent Appl. No. 14807120.0, dated Jun. 29, 2016, 11 pages.
Japanese Office Action and Search Report to JP2016-517149, 5 pages.
Office Action from JP 2016-517149 dated Jan. 10, 2017.

* cited by examiner

MULTI-TARGETED UBENIMEX PRODRUG DERIVATIVE AND PREPARATION METHOD AND USE THEREOF

CROSS REFERENCE to RELATED APPLICATIONS

This application is the U.S. national phase entry of PCT/CN2014/079312, with an international filing date of Jun. 6, 2014, which claims priority to and any benefit of Chinese Patent Application No. 201310225754.2, filed Jun. 7, 2013, and Chinese Patent Application No. 201310393152.8, filed Sep. 3, 2013, the entire contents of which are incorporated by reference in their entirety.

FIELD OF THE INVENTION

The present invention relates to pharmaceutical chemistry field, particularly relates to a multi-targeted Ubenimex prodrug derivative and preparation method thereof, and its medical use especially as anti-tumor drug (for solid tumor in particular).

BACKGROUND OF THE INVENTION

Aminopeptidase N (APN/CD13) is a zinc-dependent type II trans-membrane metallopeptidase, belonging to the Gluzincins subfamily of the M1 family, which binds to cellular membrane in a form of a homodimer (*Nucleic Acids Res.*, 1999, 27(1):325-331). CD13 is expressed on diverse cell surfaces, such cells as central nervous system synapse cells, synovial fluid fibroblasts, activated endothelial cells, liver cells, intestinal epithelial cells, placenta, bone marrow progenitors, monocytes, osteoclasts and so on, particularly is enriched on kidney and intestinal brush border (*Haema.*, 2003, 4(6):453-461). Moreover, compared with normal cells, many tumor cells have a relatively high expression of CD13 on their cell surface, such as melanoma, ovarian cancer, prostate cancer, colon cancer, pancreatic cancer, breast cancer, lung cancer and so on.

In recent studies, it is found CD13 is a multifunctional protein, playing a role as proteolytic enzyme, virus receptor, signal transduction molecule on cell surface and so on, while CD13 is involved in cancer invasion, metastasis, and angiogenesis (*Current Medicinal Chemistry*, 2007, 14, 639-647). Recently, it is reported that the CD13 on surface of tumor cells could change surrounding tissue microenvironment, and has a significant effect on angiogenesis (*PNAS* 2012, 109, 1637-1642). In addition, Haraguchi etc. suggest that CD13 is a functional bio-marker of semi-dormant liver cancer stem cells (HCSCs) in Human hepatoma cells and its clinical samples, and could prevent an increasing of Reactive Oxygen Species inducing by radiotherapy/chemotherapy to increase resistance for treatment (*J Clin Invest* 2010, 120, 3326-3339). It is well-known that tumor stem cells are the main factor causing tumor chemotherapy resistance, recurrence and metastasis. It is shown in further studies that, CD13$^+$ liver cancer cells proliferate slowly, and have a capability of self-renewing, differentiating and resisting to treatment, and are related to tumor resistance. CD13 inhibitors and CD13 neutralizing antibody can both induce cell apoptosis and affect tumor cells with multi-drug resistance, cytotoxic anti-tumor drug and CD13 inhibitor can highly enhance inhibiting and killing of tumor, thus the combination of ubenimex with other cytotoxic anti-tumor drugs can highly enhance therapeutic effect compared with ubenimex, what is more, can prevent recurrence and metastasis of tumor (*J Clin Invest* 2010, 120, 3326-3339).

Ubenimex (Ubenimex, Bestatin, Ube) is a compound with a dipeptide structure found from a nutrient solution of *Streptomyces olivoreticuli*, which was used as immunoenhancement for the treatment of leukaemia in 1987 in Japan. And then it was on market in 1998 in China with a trade name Bestatin. Bestatin is an immunoenhancement with targeted anti-cancer capacity and dual mechanism. Lots of studies have reported an inhibiting activity of Bestatin on CD13 with IC$_{50}$ value of 2.5-16.9 μM against CD13. In vitro, Bestatin can inhibit an invasion of a murine melanoma B16BL6 with high metastasis; and also can inhibit a tubular structure formation of HUVECs (*Cancer let*, 2004, 216(1): 35-42). Moreover, mice xenografts experiments suggest that Bestatin can inhibit carcinoma metastasis and angiogenesis induced by tumor cells (*Bio. Pharm. Bull.*, 1996, 19(1):6-10); in clinical study, Bestatin can cooperate with chemotherapy, radiotherapy and combination application to be used in treatment of disease such as leukaemia, multiple myeloma, myelodysplastic syndrome, and other diverse solid tumors. However, mechanism of synergy effect thereof is uncertain.

Recently, in a mice liver cancer xenograft experiment, the combination of ubenimex and 5-Fluorouracil presented an enhanced effect on inhibiting tumor comparing with a single treatment using ubenimex or 5-Fluorouracil (shown in FIG. 1, 2). Otherwise, it was found in further experiment that, the liver cells of a mouse treated by 5-Fluorouracil before was transplanted into other mouse, and by comparing the tumor recurrence of a mice group using ubenimex with the mice group without using ubenimex, it results that, tumor did not recur in the mice group using ubenimex, but the mice group without using ubenimex presented tumor recurrence cases. This study provides great evidence for combination of ubenimex with 5-Fluorouracil and other chemotherapeutics (*J Clin Invest* 2010, 120, 3326-3339). And it also validates the importance of inhibiting tumor stem cells in tumor chemotherapy.

5-Fluorouracil (5-Fluorouracil, 5-Fu) is a kind of pyrimidine fluoride with a chemical name of 2,4-dihydroxy-5-fluoropyrimidine and belongs to antimetabolite anti-tumor drugs, and can inhibit thymidylate synthase, block deoxythymidylate converting into thymidylate, interfere with DNA synthesis and inhibit RNA synthesis in some degree. 5-Fluorouracil is a widely used clinical anti-tumor drug for treatment of colon cancer, colorectal cancer, stomach cancer, breast cancer, ovarian cancer, choriocarcinoma, malignant mole, head and neck squamous cell carcinoma, skin cancer, liver cancer, bladder cancer, etc., which presents no cross resistance with other general anti-tumor drugs. Otherwise, many antitumor drugs combining with 5-FU exhibit enhanced cytotoxic effect, there has been some studies on drug combination of 5-FU for treating leukaemia (*Phytomedicine* 18 (2011) 362-365). However, 5-FU is used widely in clinical and has therapeutic effect on many tumor diseases, while having many disadvantages: the effective dose of 5-FU is less different with its toxic dose, which induces the relatively severe myelosuppression and gastrointestinal toxicity in clinical. Short half-life, poor metabolic stability (degraded to FUH$_2$ by dihydropyrimidine dehydrogenase soon) and some tumors with high expression of thymidylate synthase resisting to it are also its disadvantages. Because of oral irregular, large individual differences, low fat-solubility and poor tissue penetration, it is difficult to prepare a convenient oral formation of 5-fluorouracil, therefore, it is administrated by artery or vein mostly, and is not suitable for the long-term chemotherapy.

In decades, many researchers want to reduce or avoid the disadvantages of 5-FU. Among which, the main method is developing pro-drug of 5-FU to improve metabolic stability, reduce toxicity and increase therapeutic index of it. So far, many pro-drug derivatives of 5-FU have been synthesized and some of those have been used in clinial, such as tegafur (FTO), carmofur (HCFU), doxifluridine, capecitabine (Xeloda), atofluding (ATFU), BOF-A2 and so on. Xeloda is one of those approved by FDA to be an oral fluoropyrimidine drug with the best clinical effect in present, which could meet or exceed the efficacy of fluorouracil by continuous intravenous administration; atofluding can be progressively degraded into TFU and 5-Fu in body so as to have continuous effect. In this invention, by using Xeloda and TFU as the positive control drugs, we evaluate the oral pharmacodynamic effect of a multi-target ubenimex-5-FU binded pro-drug derivative synthesized by ourselves.

Hydroxyurea (Hydroxycarbamide), a nucleoside diphosphate reductase inhibitor, can block reduction of nucleotides to deoxynucleotides, interfere with biosynthesis of purine and pyrimidine bases, selectively impede DNA biosynthesis but has no impact on RNA and protein biosynthesis. As a cell cycle-specific drug, cells in s-phase are sensitive to it. Now, it is mainly used for the treatment of solid tumors, such as malignant melanoma, stomach cancer, colon cancer, breast cancer, bladder cancer and so on.

Epirubicin (Epirubicin), an antibiotic anti-tumor drug, is an isomer of doxorubicin, which can directly embed in DNA base pairs in nucleus to interfere with transcription progress, and then prevent formation of mRNA to inhibit biosynthesis of DNA and RNA. Moreover, many other researchers find that epirubicin can inhibit the topoisomerase II and is a cell cycle nonspecific agent. Now, it is mainly used for the treatment of solid tumors in clinical, such as acute leukemia, nephroblastoma, soft tissue sarcoma, bladder cancer, testicular cancer, prostate cancer, stomach cancer, malignant lymphoma, breast cancer, bronchial carcinoma, ovarian cancer, liver cancer (including primary hepatocellular carcinoma and metastatic hepatocellular carcinoma) and so on. So far, combination application of epirubicin has been widely reported, for example, combination of epirubicin with paclitaxel or sorafenib is useful for treatment of advanced breast cancer.

Dasatinib (Dasatinib), explored by the Bristol-Myers Squibb corporation, was approved by FDA in June of 2006 for treatment of imatinib-resistant CML patients or patients with imatinib failure. As a kind of oral tyrosine kinase inhibitor, it can treat chronic myeloid leukemia by preventing leukemia cell excessively proliferating in CML or Ph+ALL patients through targeting tyrosine kinase inhibition enzyme cascade. Other than, Dasatinib can inhibit Src kinase, thus can prevent other human tumor cells with no BCR-ABL expression, such as PC-3 (prostate cancer cells, $IC_{50}$ is 5~9 nmol/L), MDA-MB-211 (breast cancer cells, $IC_{50}$ is 10~12 nmol/L), and WiDr (colorectal cancer cells, $IC_{50}$ is 38~52 nmol/L), etc. (*Proc Am Assoc Cancer Res*, 2005, 46: 159).

Lenalidomide (Lenalidomide/Revlimid), explored by the U.S. Celgene corporation, is a derivative of thalidomide with a chemical name of 3-(7-amino-3-oxo-1H-isoindol-2-yl)piperidine-2,6-dione and is used for treating myelodysplastic syndrome and combining with dexamethasone for treating multiple myeloma. Lenalidomide has an impact on multiple intracellular biological pathways. Now, all the phases I, II, III clinical researches have been ended. The studies of phase I and phase II clinical researches demonstrate that it has inhibitory effect on many tumors such as multiple myeloma, prostate cancer, thyroid cancer, renal cancer, melanoma, liver cancer and chronic lymphocytic leukemia (*Cancer Chemotherapy and Pharmacology*, 2012, 1-14).

The chemical structures of ubenimex, 5-fluorouracil, hydroxyurea, cyclophosphamide, gemcitabine, tirapazamine, lenalidomide, hydroxycamptothecine, epirubicin, dasatinib, and paclitaxel are shown as below:

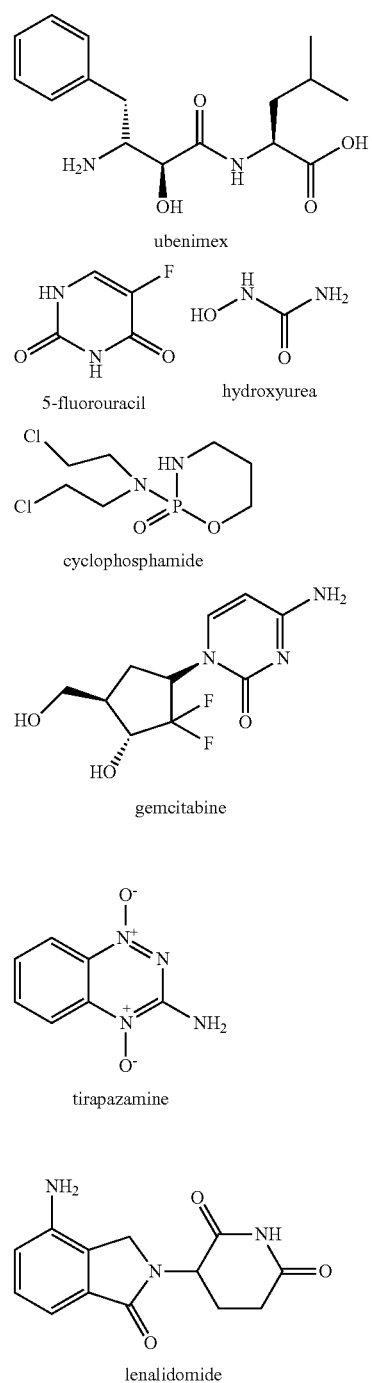

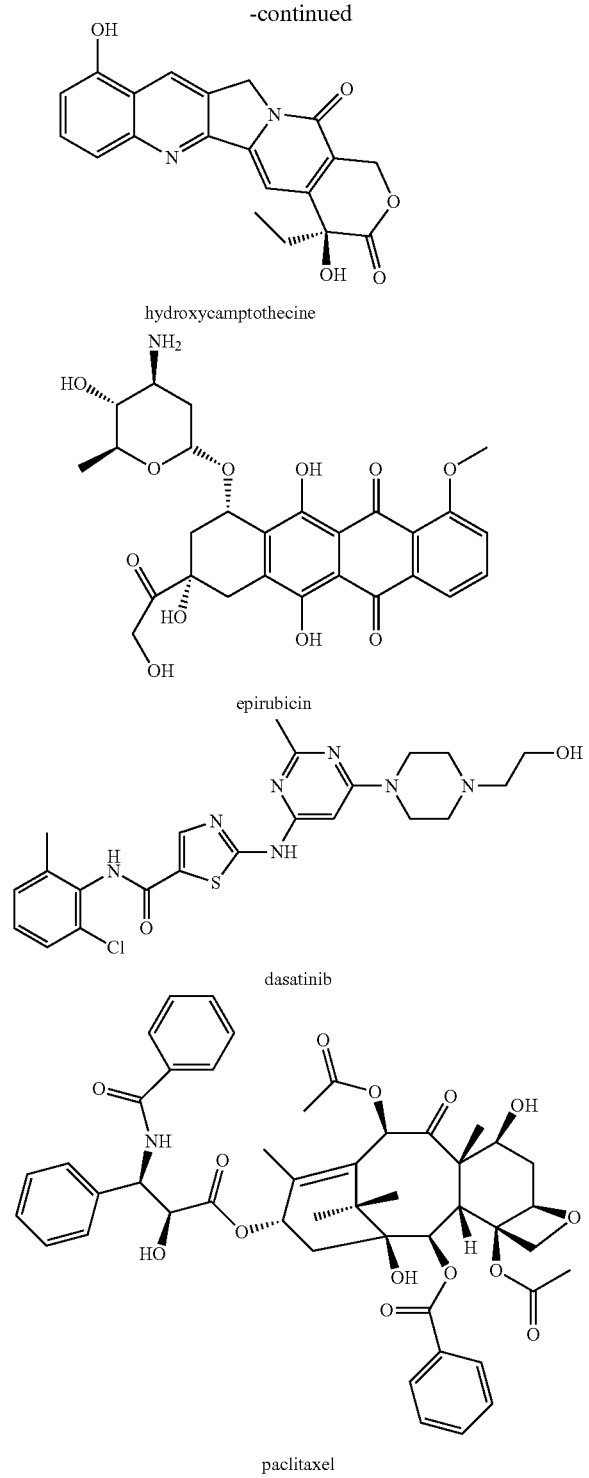

hydroxycamptothecine epirubicin dasatinib paclitaxel

Multi-targeted drug (multitarget drugs) is an important trend in today's drug research. A multi-targeted drug refers to a drug which can simultaneously act on diverse targets associated with one disease to have a synergistic therapeutic effect, and exhibits better therapeutic effects, less side effects by completely regulating multiple targets associated with one disease, and is especially useful for treating various major diseases associated with complicated pathological mechanism and polygene, including leukemia and other malignancies, central nervous system diseases, cardiovascular diseases and metabolic disorders and so on. So far, multi-targeted treatment using multi-targeted drug is one of the most effective treatments for therapy of various malignancies including leukemia.

A mutual pro-drug or a multi-targeted drug has single physical and chemical property and uniform pharmacokinetic characteristics when comparing with drug combination and a multi-targeted drug may avoid problems such as interaction of different components and differential absorption, distribution and metabolism of different components in a drug mixture, and thus can have synergistic effect, especially in a case of low concentration. A multi-targeted drug shows an obviously better therapeutic effect than combination of corresponding single-targeted drugs. Therefore, it is of great significance to design and synthesize a novel anti-cancer drug with synergistic therapeutic effect based on hybridization principle to be used to treat tumor recurrence, metastasis and drug resistance, especially binding ubenimex as a tumor stem cells inhibitor with other anti-tumor drugs.

SUMMARY OF THE INVENTION

The present invention is aimed at providing a multi-targeted ubenimex pro-drug derivative and preparation method thereof, and its medical use to overcome the defects in the prior art, and in the present invention, a series of novel mutual pro-drugs are designed and synthesized by blending a CD13 inhibitor ubenimex into molecular structure of another marketed drug (such as 5-FU, hydroxyurea, epirubicin, dasatinib, and paclitaxel) through an ester bond or an amido bond by using pharmacophore hybridization method. These pro-drugs retain an inhibition activity against CD13, which will play a targeted anti-cancer role on inhibiting tumor stem cells by inhibiting CD13 after these CD13 inhibitors entering into body.

In order to solve the above problems, a technical solution of the present invention is as follows: to provide a multi-target pro-drug derivatives of ubenimex as represented by general formula (I), as well as an enantiomer, a diastereoisomer and a racemate thereof, and a pharmaceutically acceptable salt or solvate thereof:

(I)

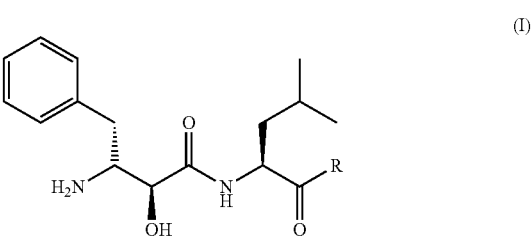

wherein, R in general structural formula (1) represents one of the following substituents:

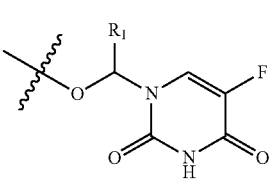

7
-continued
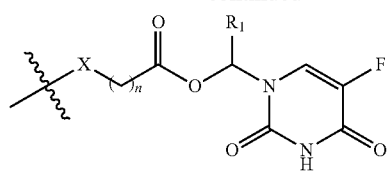
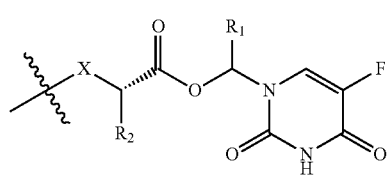
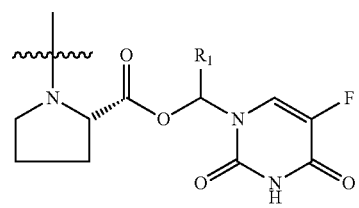
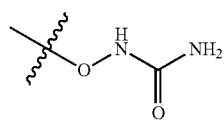
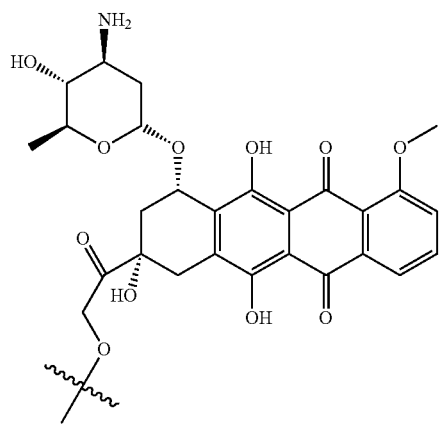
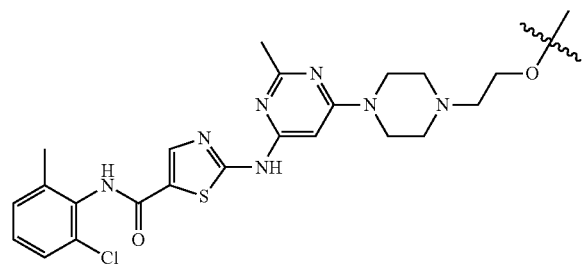
8
-continued
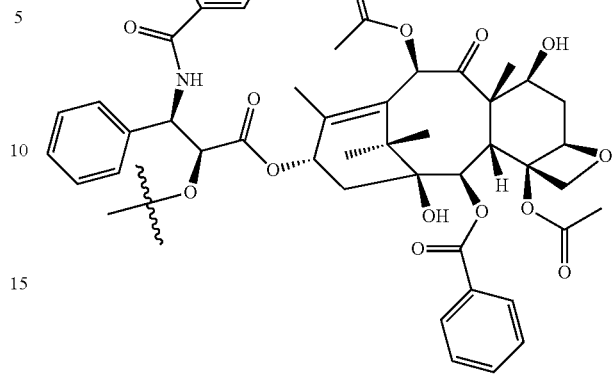
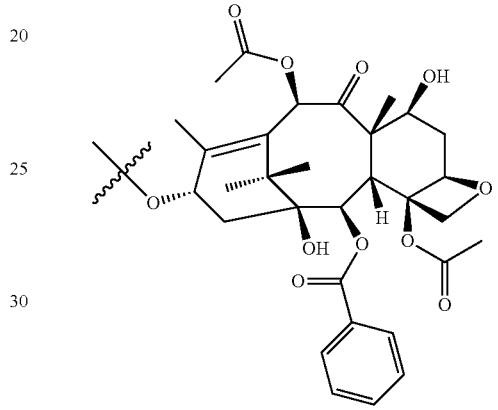
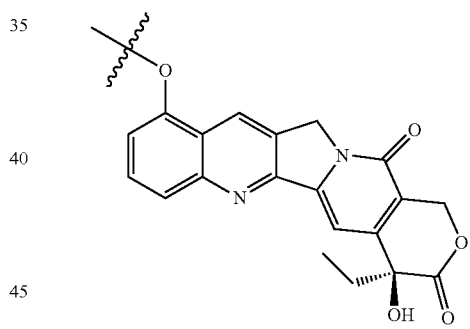
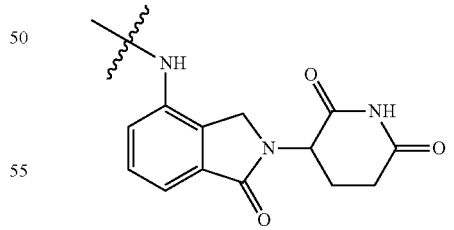
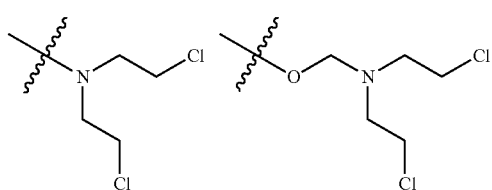

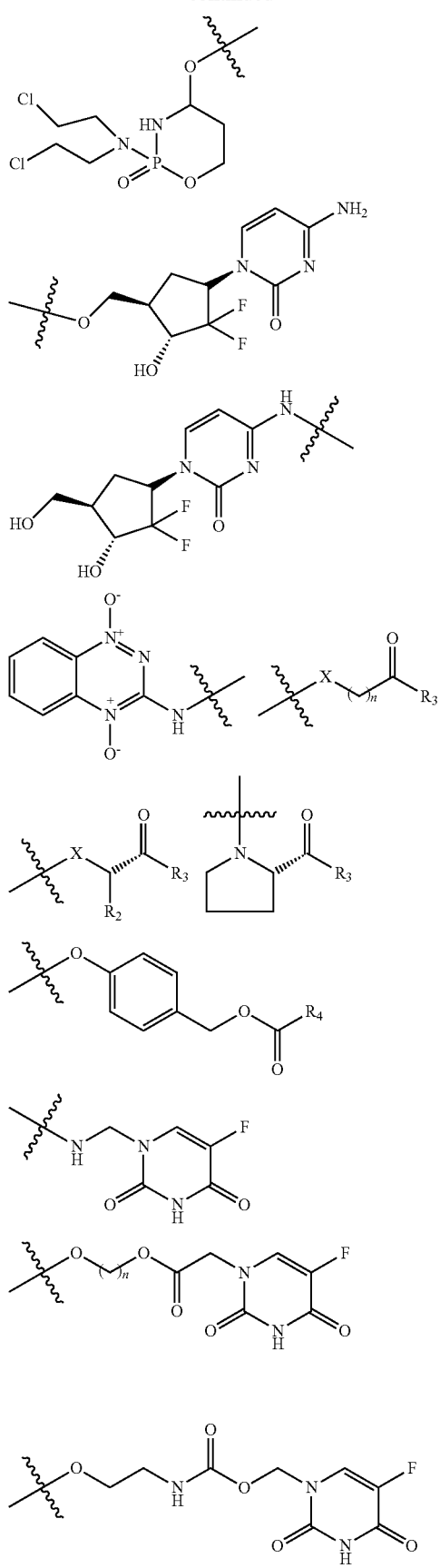
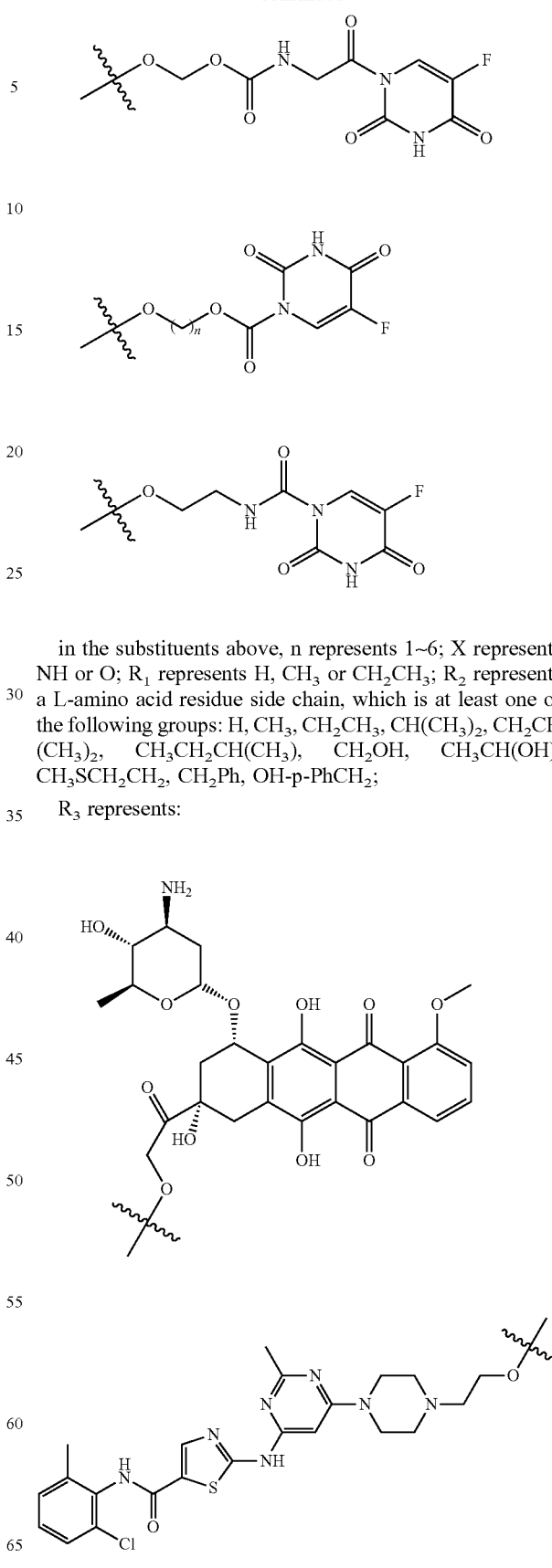
in the substituents above, n represents 1~6; X represents NH or O; $R_1$ represents H, $CH_3$ or $CH_2CH_3$; $R_2$ represents a L-amino acid residue side chain, which is at least one of the following groups: H, $CH_3$, $CH_2CH_3$, $CH(CH_3)_2$, $CH_2CH(CH_3)_2$, $CH_3CH_2CH(CH_3)$, $CH_2OH$, $CH_3CH(OH)$, $CH_3SCH_2CH_2$, $CH_2Ph$, OH-p-$PhCH_2$;
$R_3$ represents:

11
-continued
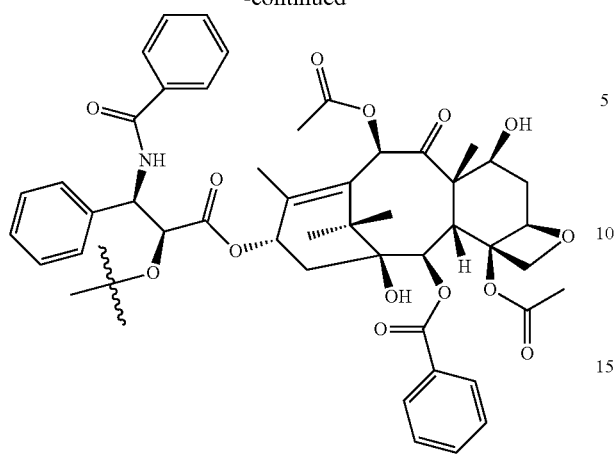
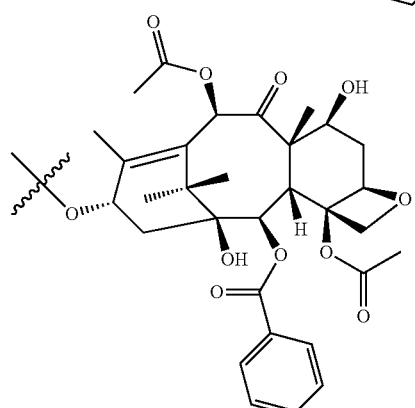
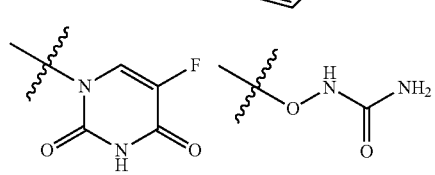
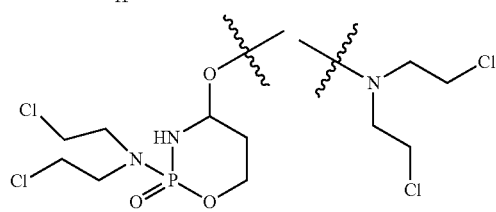
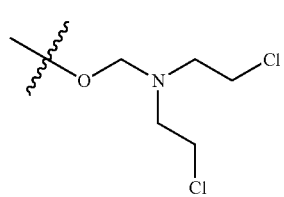
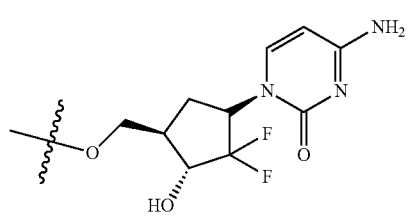
12
-continued
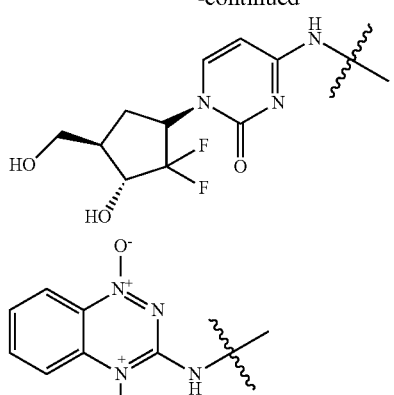
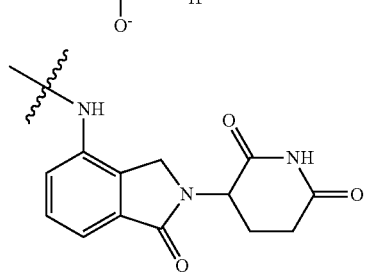
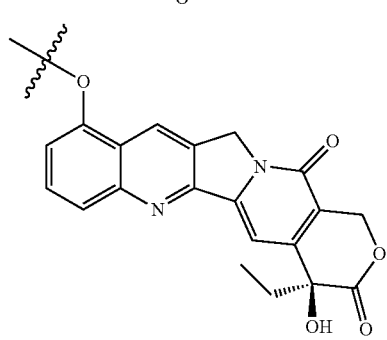
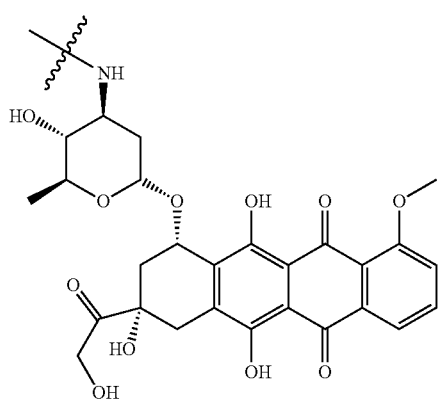
$R_4$ represents:
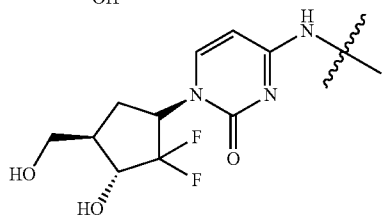

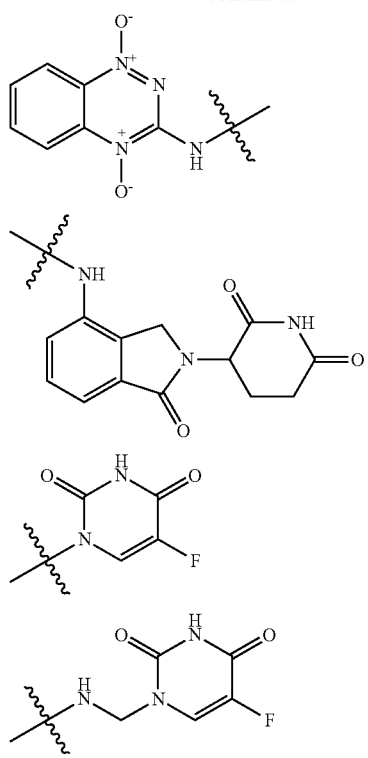
In the general structural formula (I) of the present invention, R may represent the following substituents:
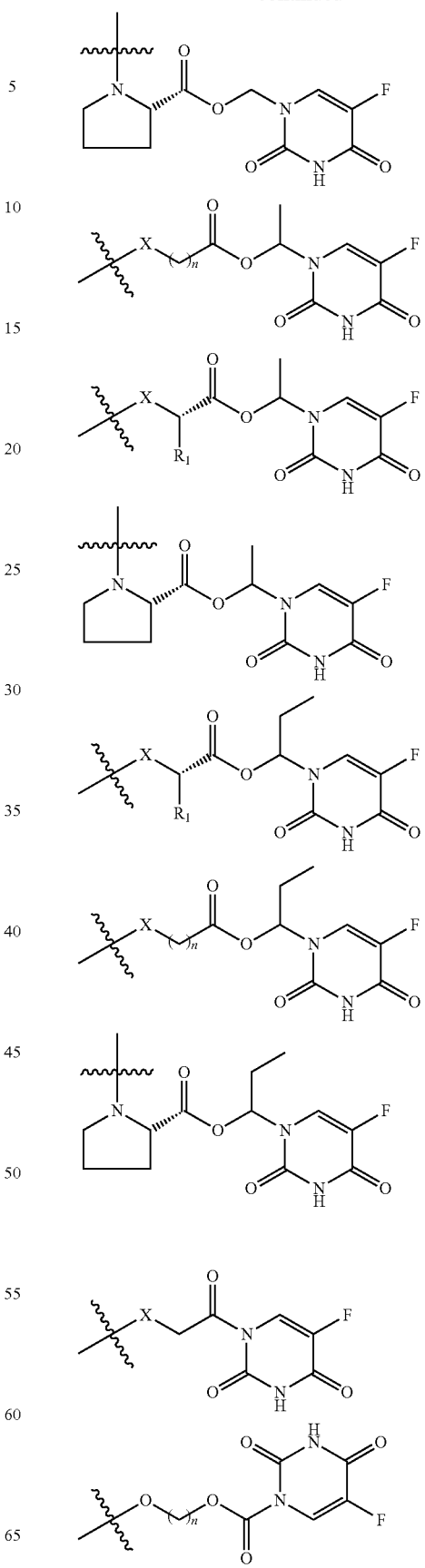

15
-continued
16
-continued
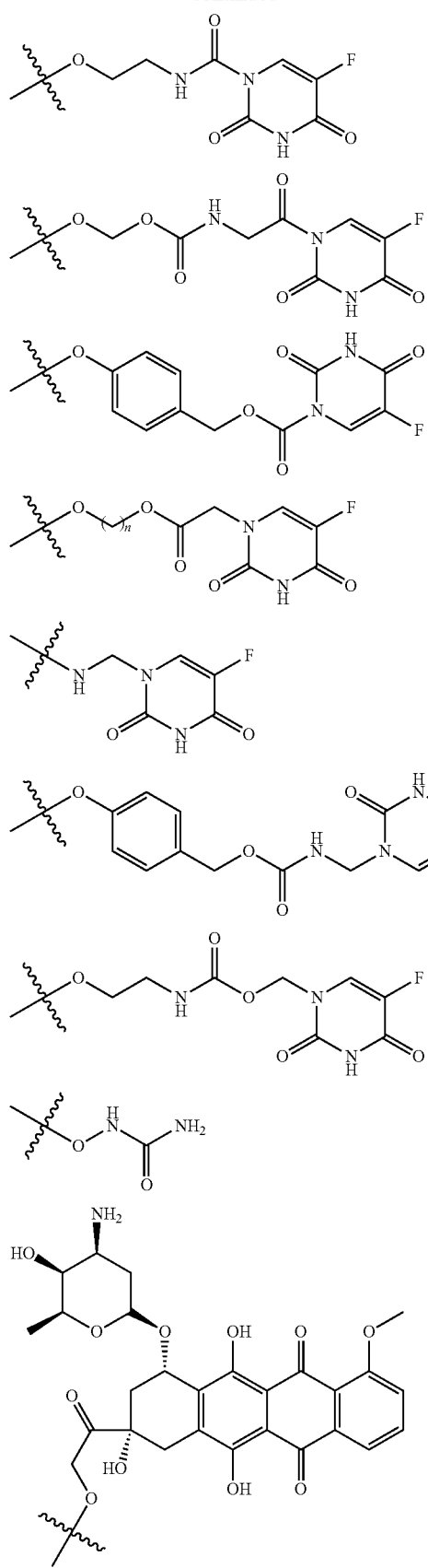
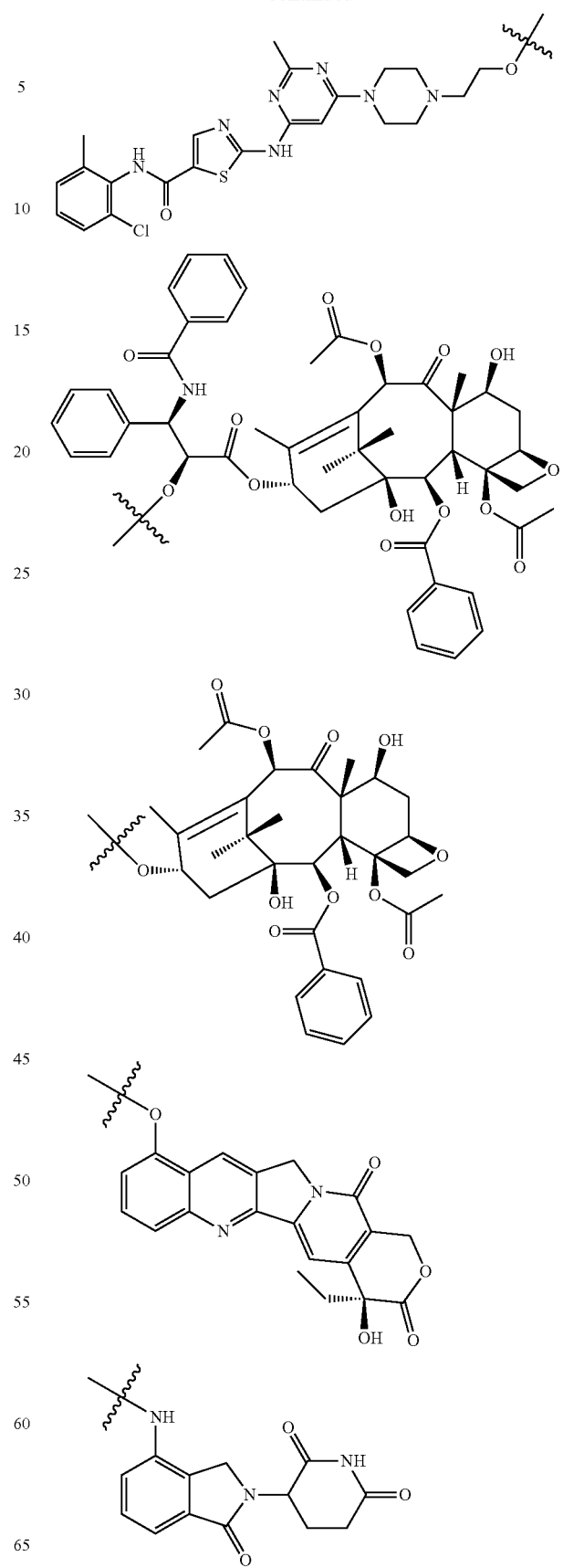

-continued
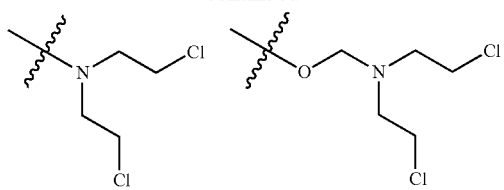
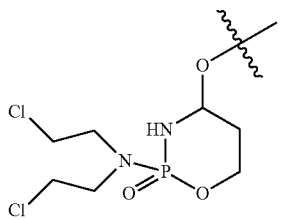
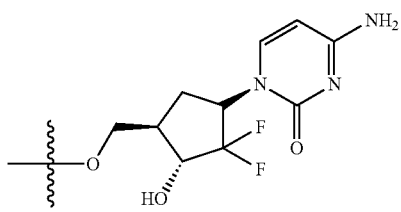
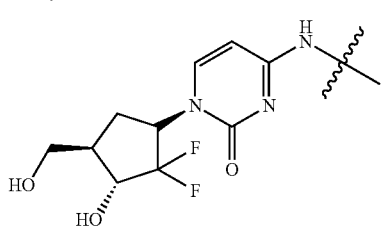
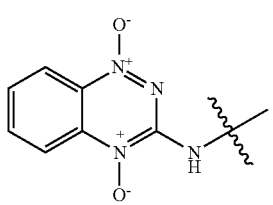
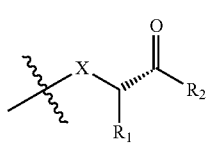
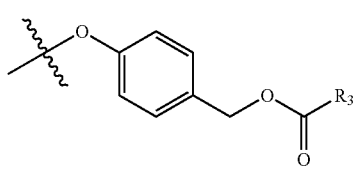
wherein, in the substituents above, n represents 1~6; X represents NH or O; $R_2$ represents a L-amino acid residue side chain, which is at least one of the following groups: H, $CH_3$, $CH_2CH_3$, $CH(CH_3)_2$, $CH_2CH(CH_3)_2$, $CH_3CH_2CH(CH_3)$, $CH_2OH$, $CH_3CH(OH)$, $CH_3SCH_2CH_2$, $CH_2Ph$, OH-p-$PhCH_2$;
$R_3$ represents:
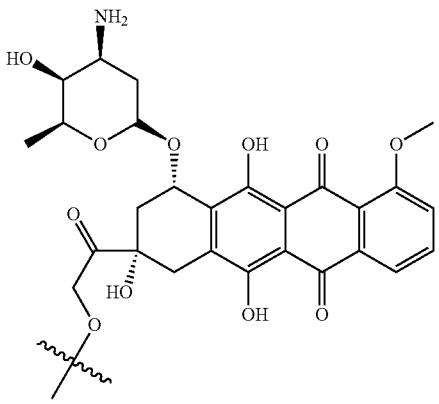
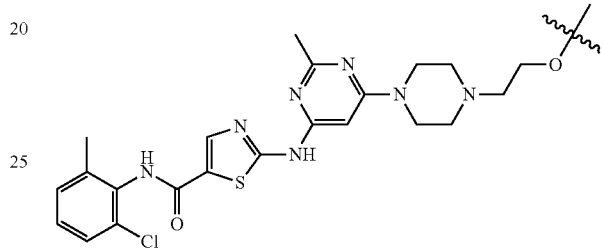
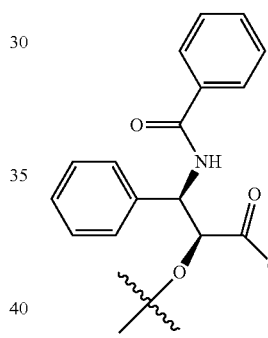
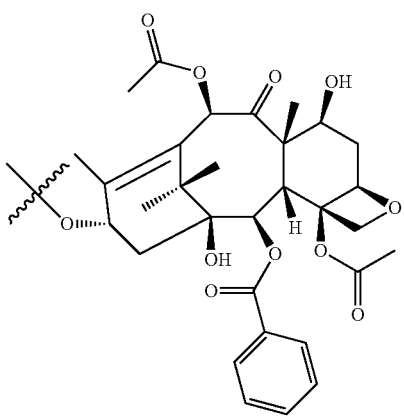
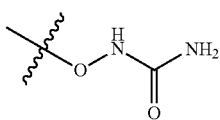

-continued
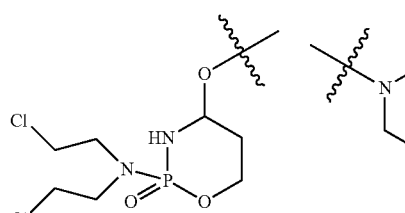
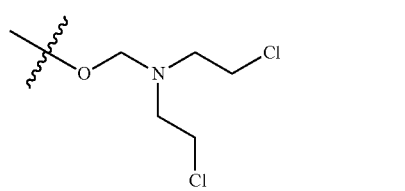
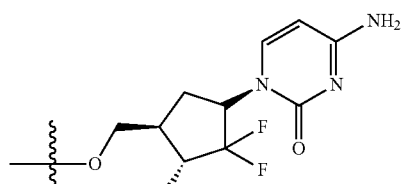
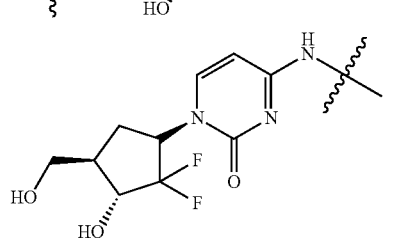
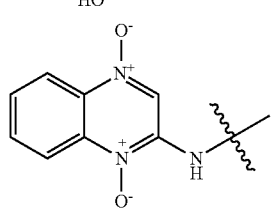
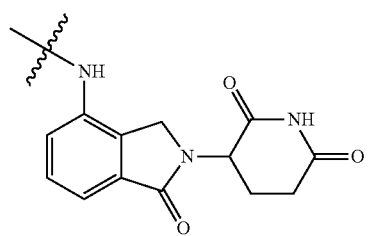
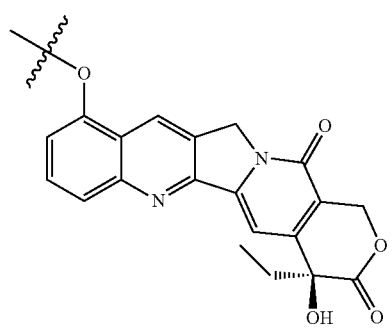
$R_4$ represents:
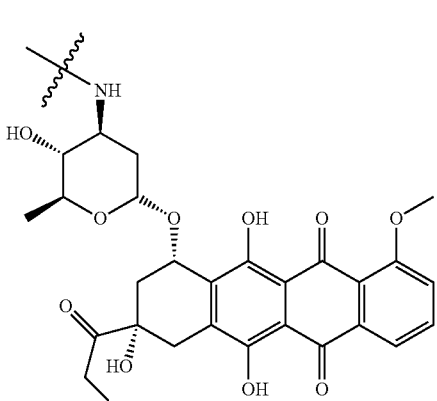
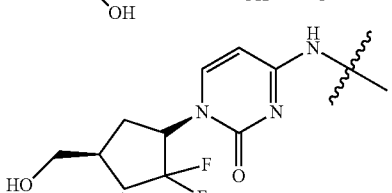
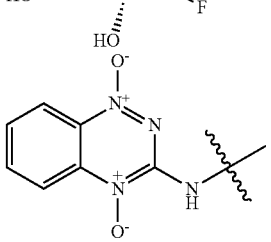
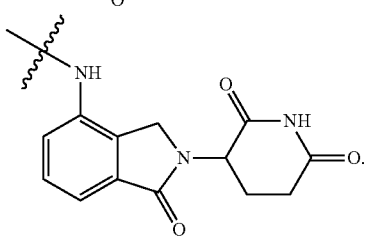
In the general structural formula (I) of the present invention, R may represent the following substituents:
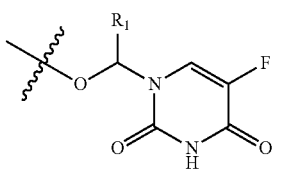
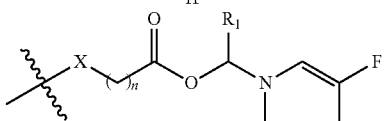
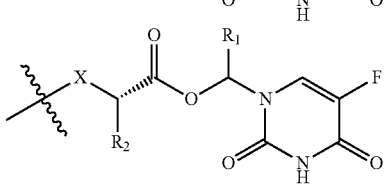

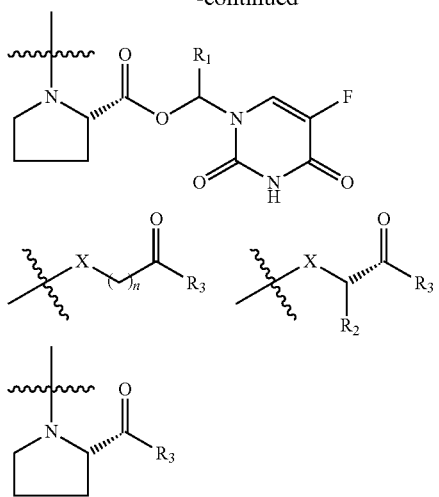
in the substituents above, n, X, $R_1$, $R_2$, $R_3$ are defined as above mentioned, $R_3$ represents:
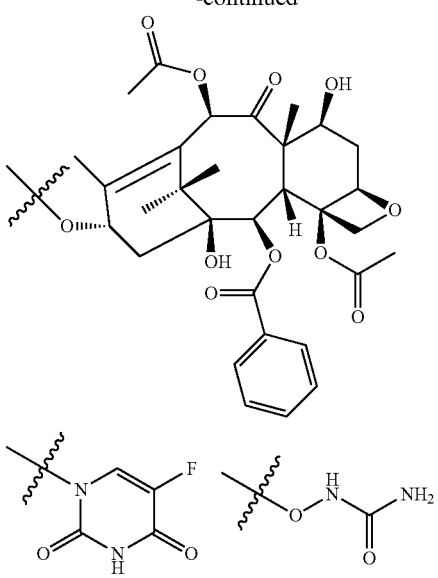
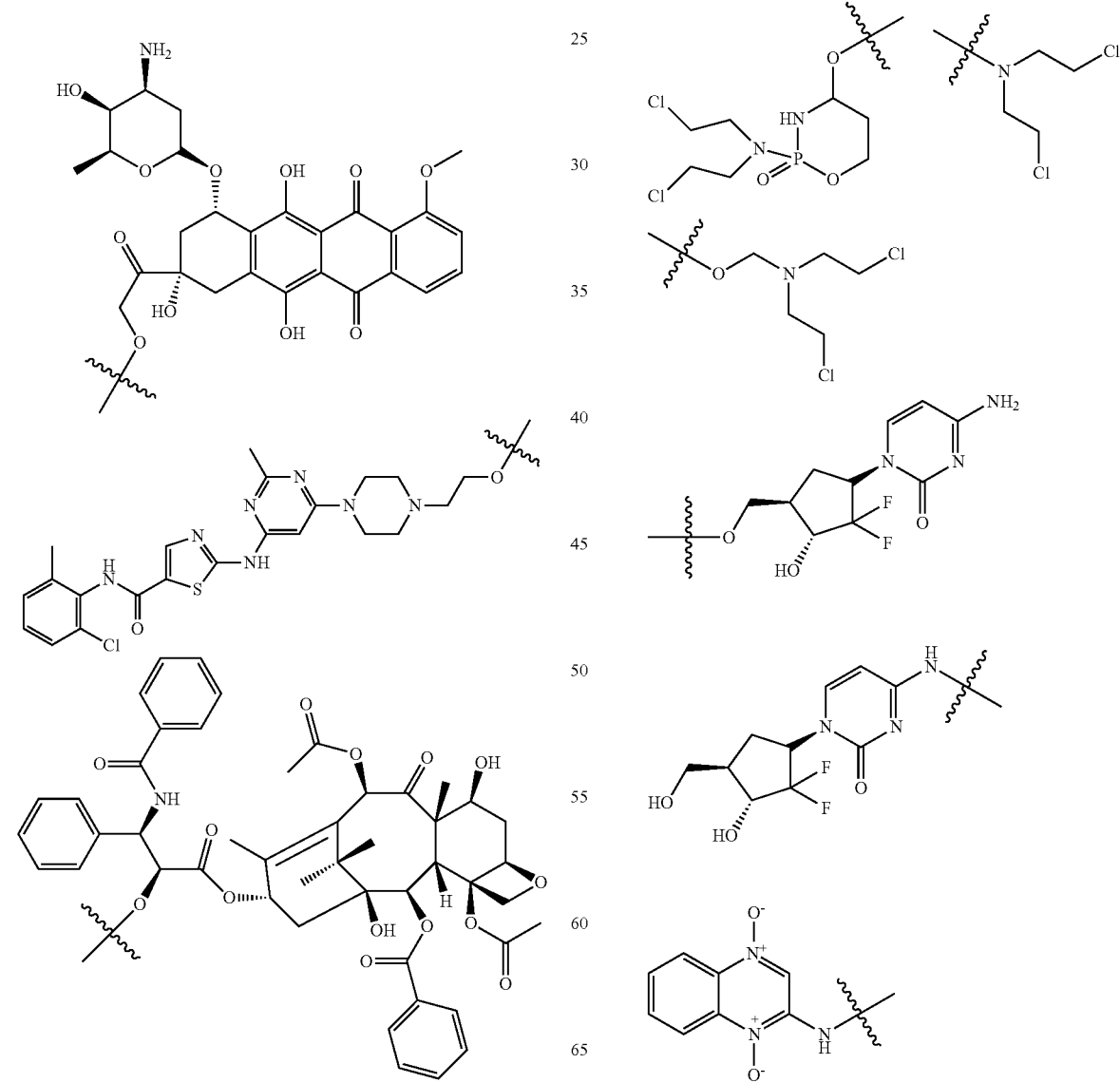

-continued
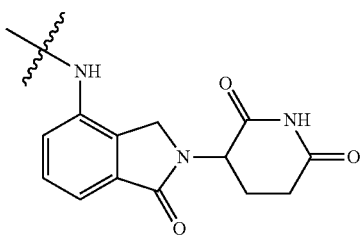
wherein, the structure of R is preferred to be one of the structures below:
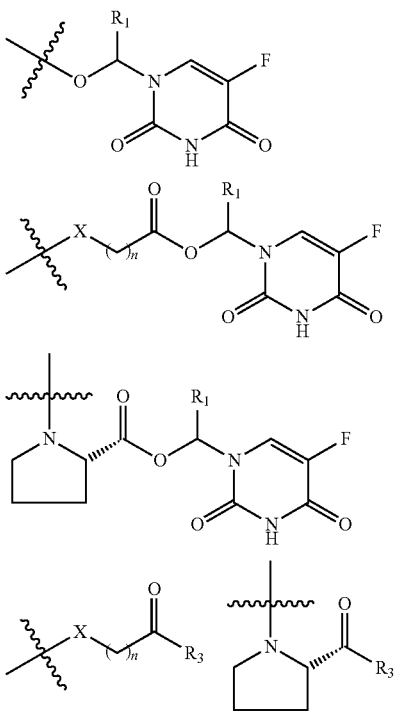
in the substituents above, n represents 1~4; X represents NH or O; $R_1$ represents H;
$R_3$ is especially preferred to represent:
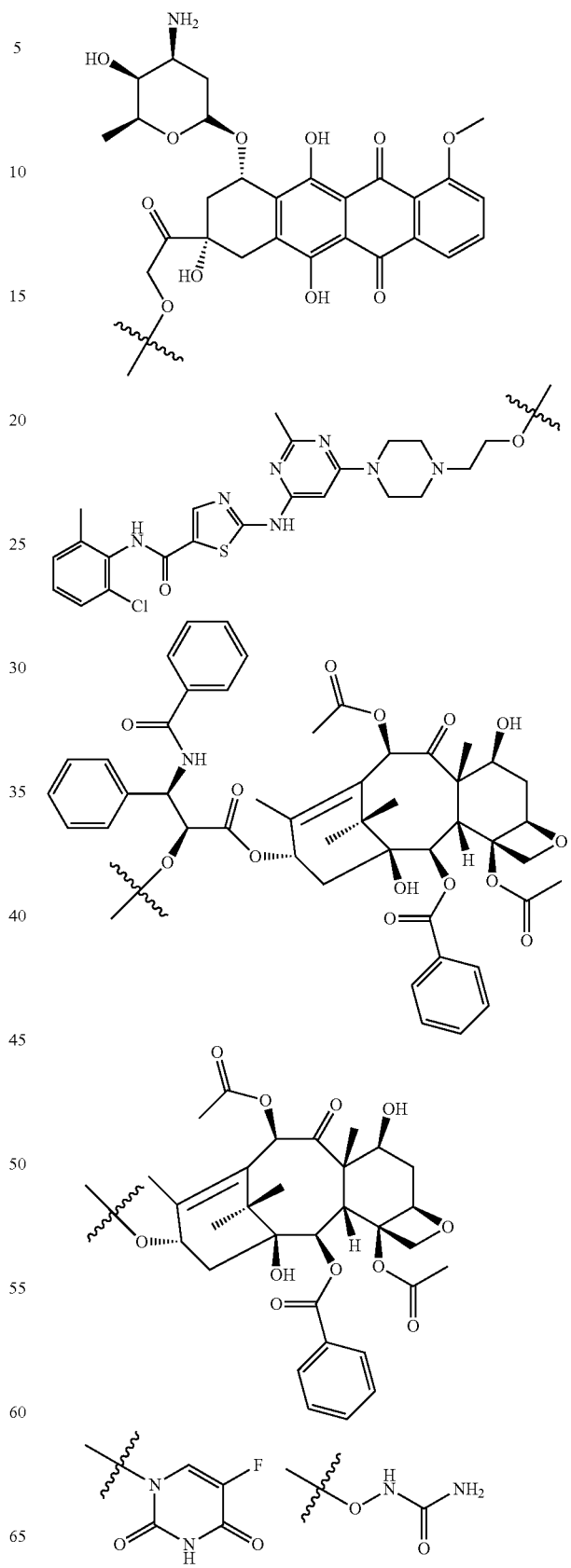

-continued
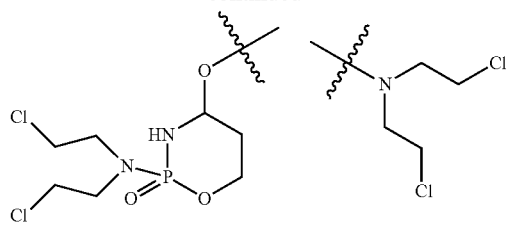
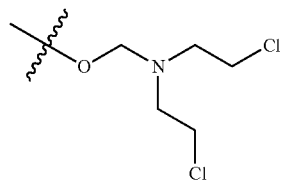
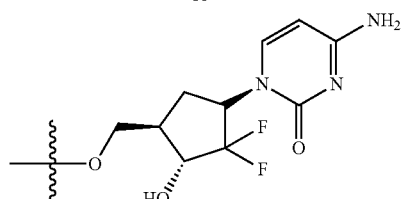
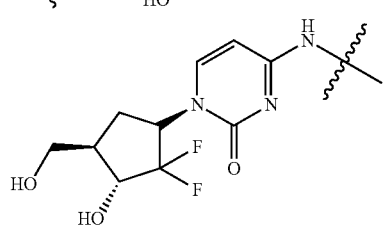
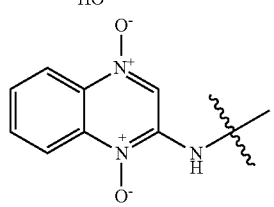
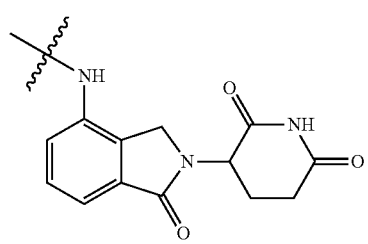
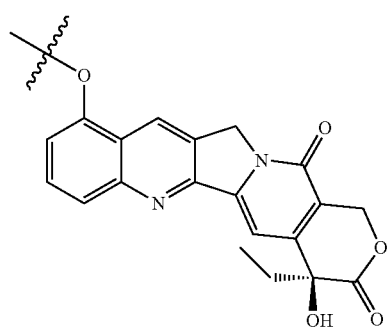
R is especially preferred to represent:
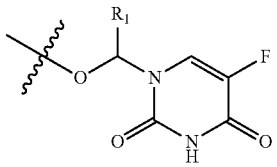
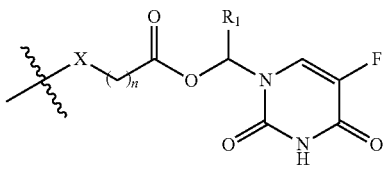
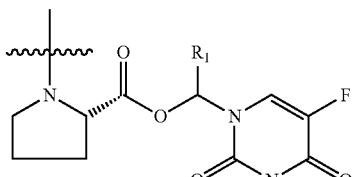
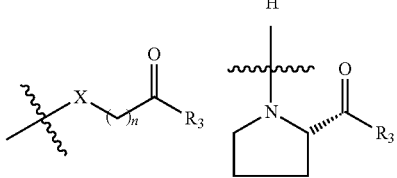
in the substituents above, n represents 1 or 2; X represents NH or O; $R_1$ represents H;
$R_3$ represents:
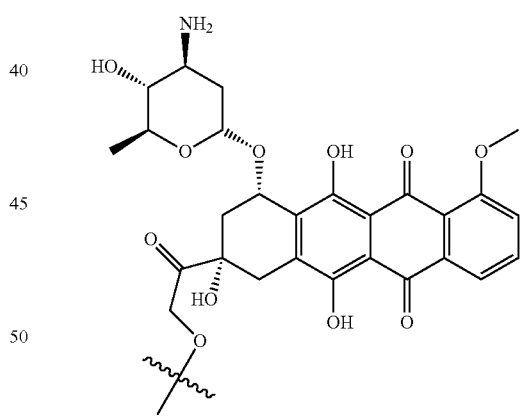
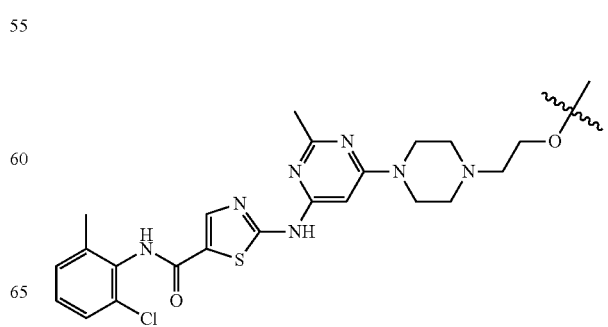

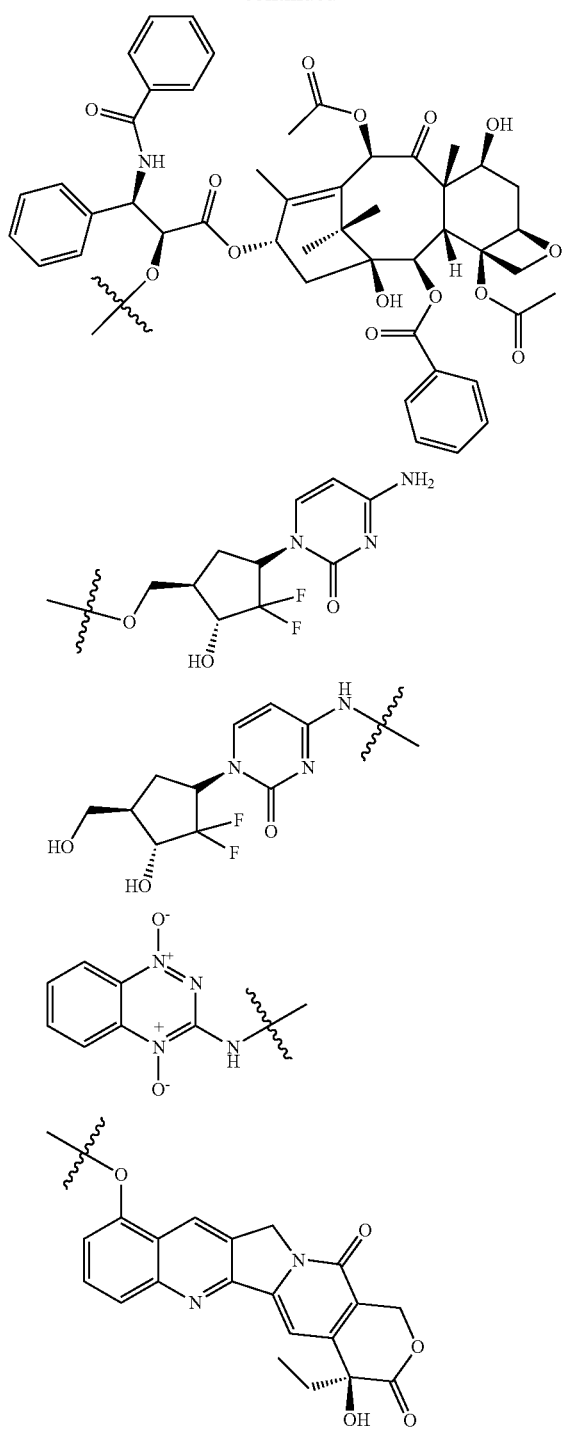

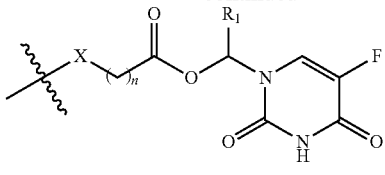

in the substituents above, n represents 1; X represents NH; $R_1$ represents H;

In the general structural formula (I) of the present invention, R may represent the following substituent:

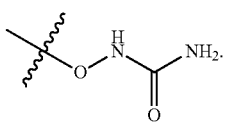 [SMILES: *ONC(N)=O]

In the general structural formula (I) of the present invention, R may represent the following substituent:

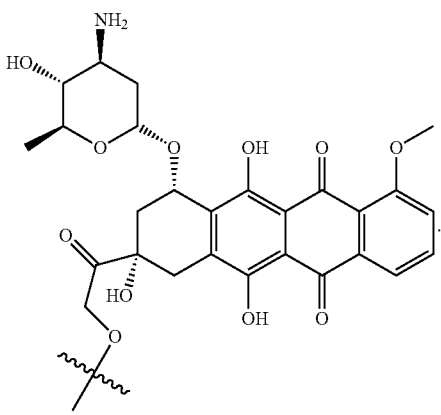

In the general structural formula (I) of the present invention, R may represent the following substituents:

The most preferred R represents:

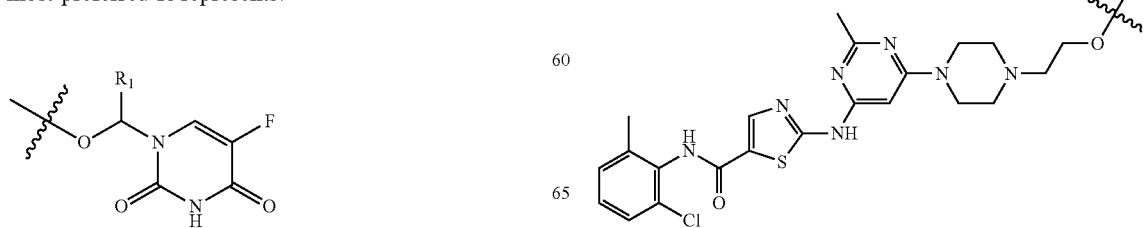

29
-continued
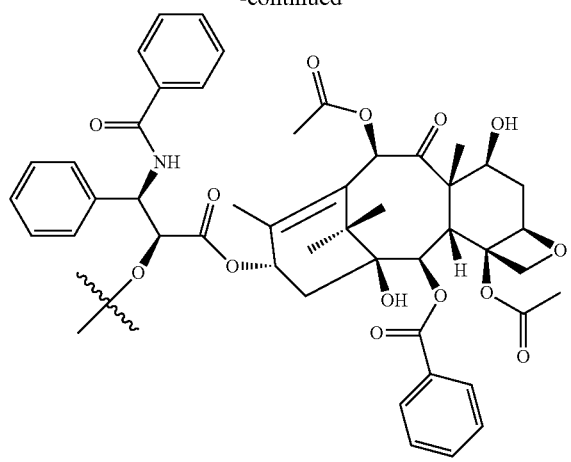
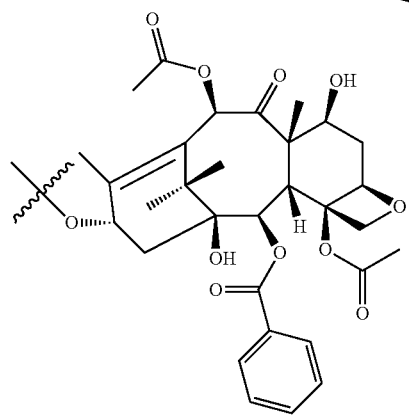
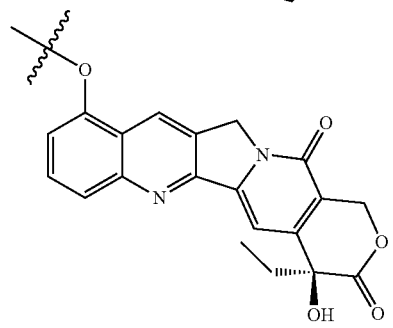
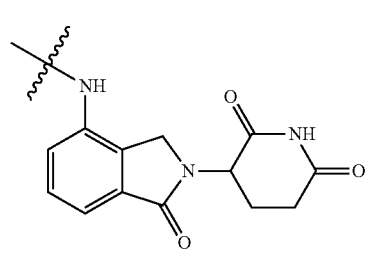
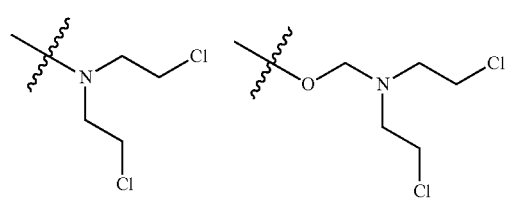
30
-continued
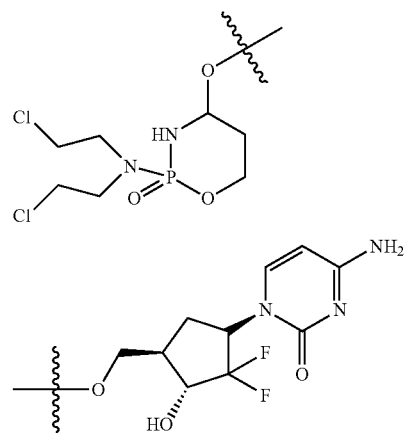
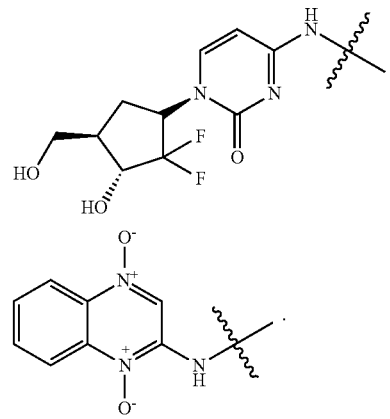
wherein, the structure of preferred R is:
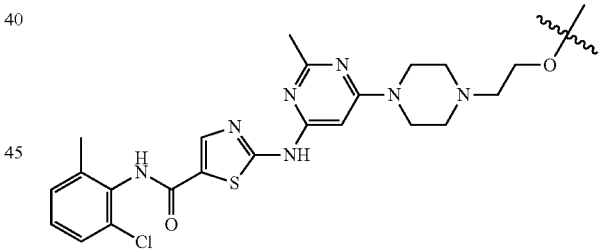
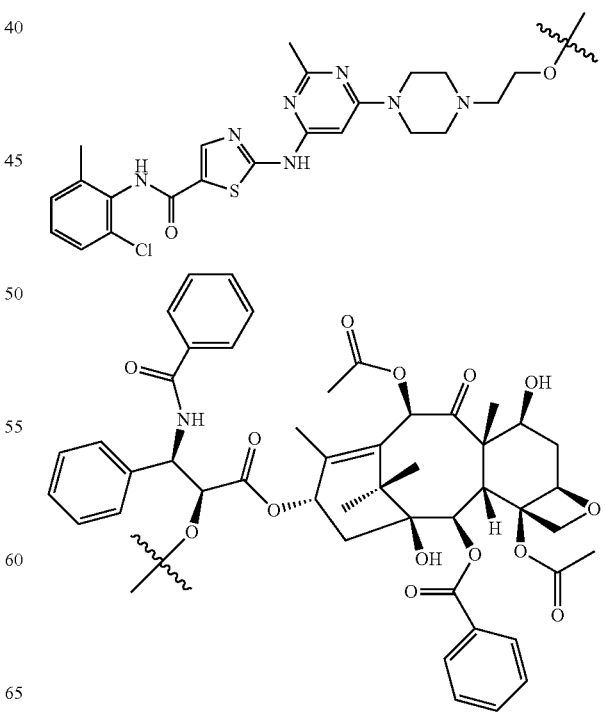

-continued
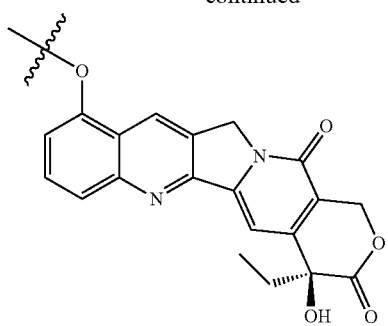
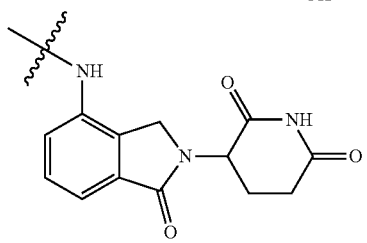
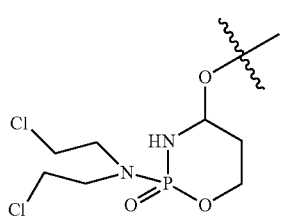
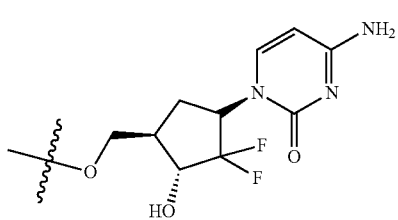
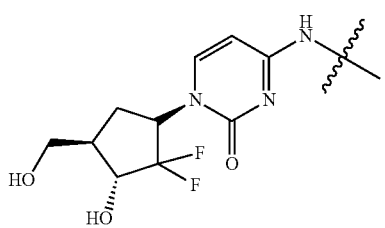
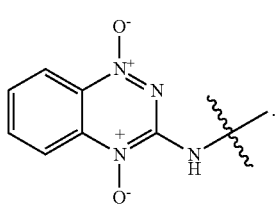
The especially preferred R is:
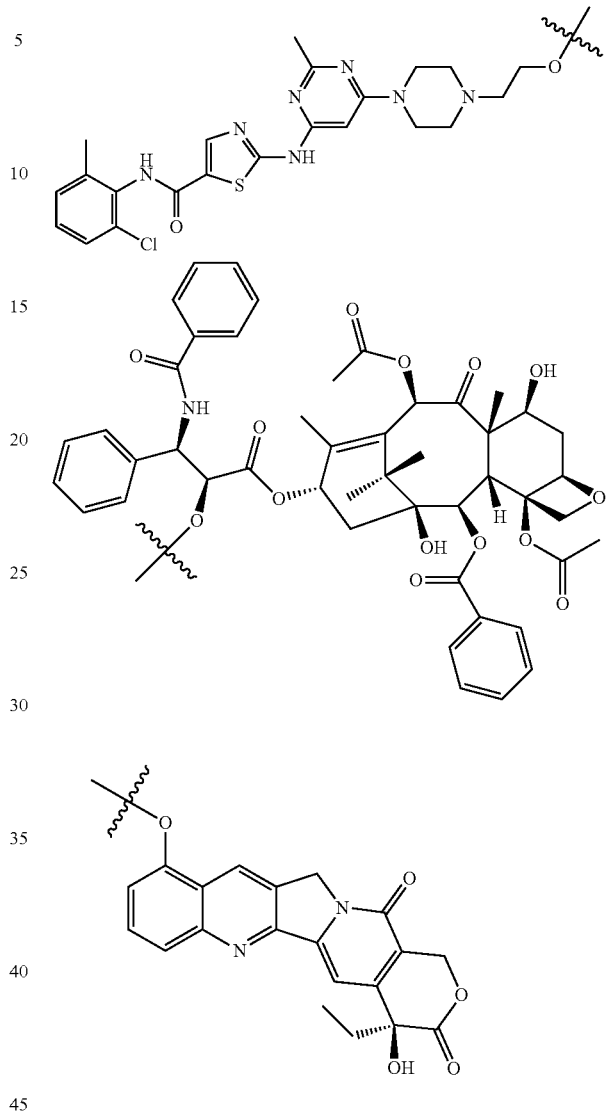
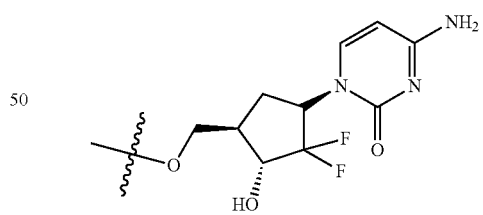
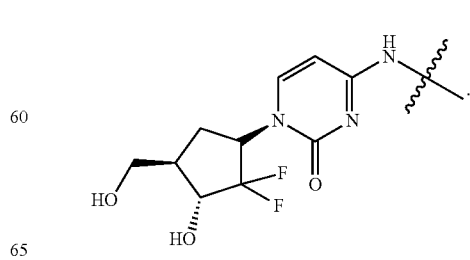

The most preferred R is:
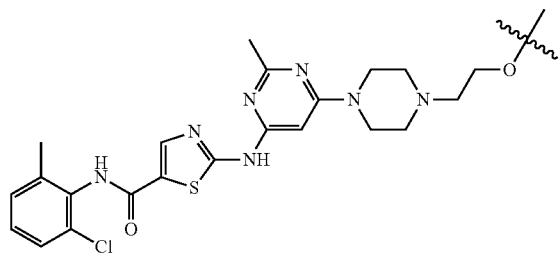
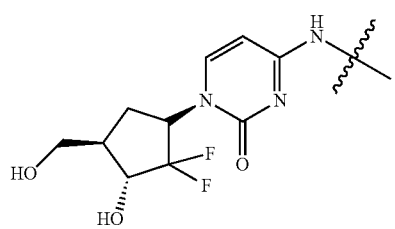
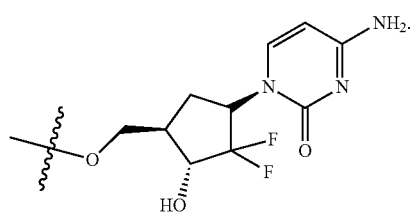
In the general structural formula (I) of the present invention, R may represent the following substituents:
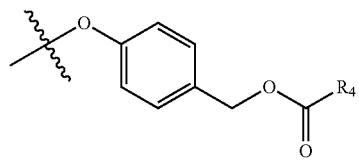
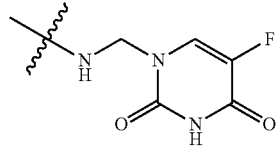
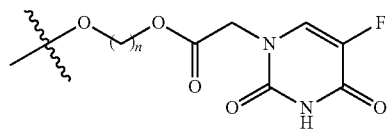
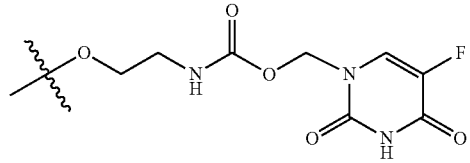
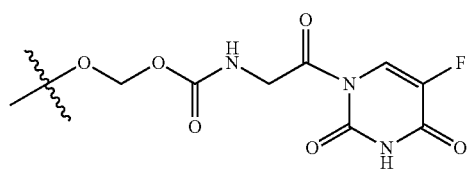
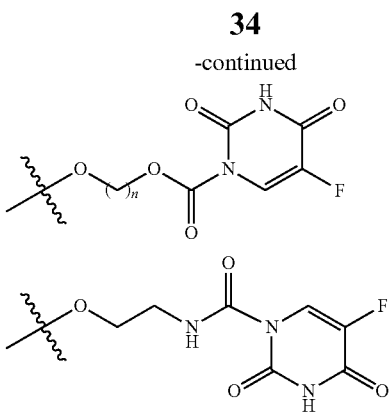
in the substituents above, n represents 1~6;
$R_4$ represents:
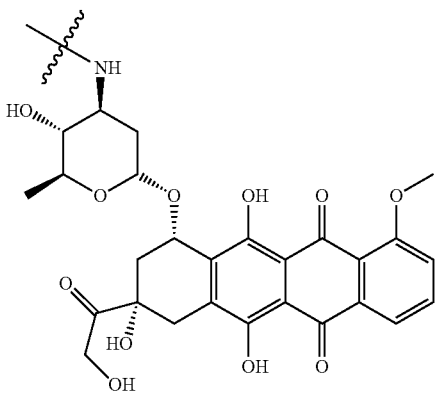
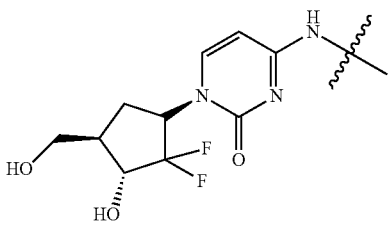
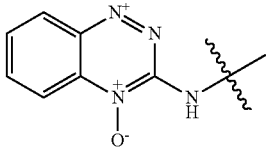
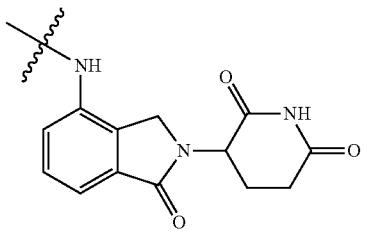
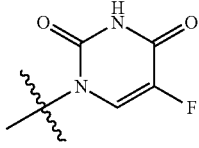

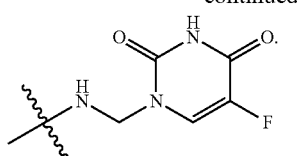
wherein, the structure of preferred R is:
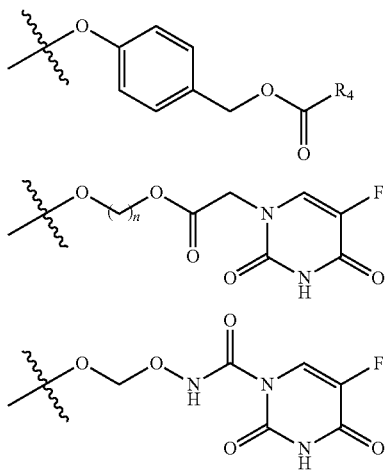
in the substituents above, n represents 1~6; R₄ represents:
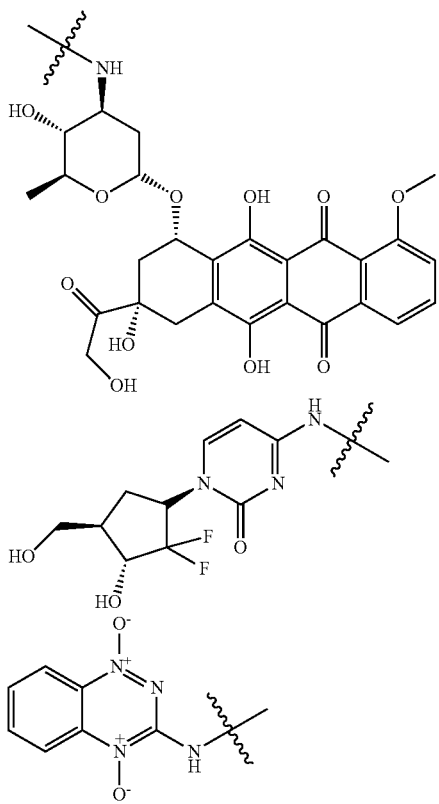
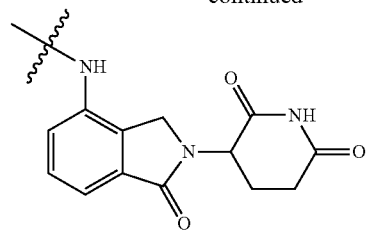
The especially preferred R is:
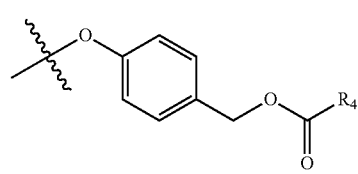
in the substituents above, R₄ represents:
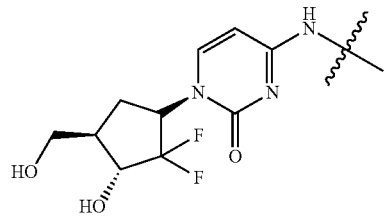
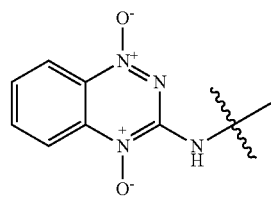
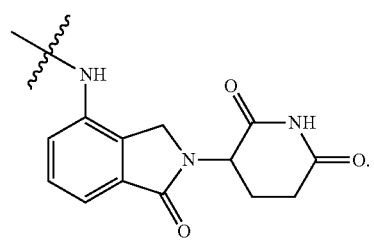
The most preferred group for R is:
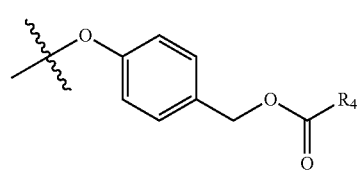

in the substituents above, $R_4$ represents:

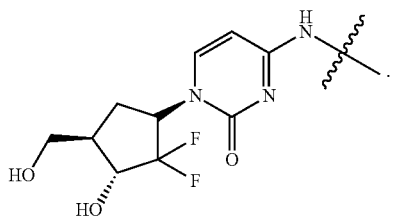

In the multi-targeted Ubenimex pro-drug derivative of the present invention, the term "pharmaceutically acceptable salt" is intended to mean a compound represented by formula (I) in salt form that retaining therapeutic effect and nontoxicity. It can be formed to be a cation salt by any alkaline group (such as amino). It is well known that many of the salts are cation salts formed by any alkaline groups (such as amino) in the art. Some salt of those are known to the art. The cation salt can be formed by reaction of a corresponding acid with alkali (I), examples of such acids include inorganic acids, for example, hydrochloric acid, sulfuric acid, nitric acid, phosphoric acid and the like; or organic acids such as acetic acid, trifluoroacetic acid, propionic acid, glycolic acid, 2-hydroxy propionic acid, 2-oxopropionic acid, oxalic acid, malonic acid, succinic acid, maleic acid, fumaric acid, malic acid, tartaric acid, 2-hydroxy-1,2,3-tricarballylic acid, methyl sulfonic acid, ethyl sulfonic acid, benzene sulfonic acid, 4-methyl benzene sulfonic acid, cyclohexyl sulfinic acids, 2-hydroxy benzoic acid, 4-amino-2-hydroxy benzoic acid, and so on. These salts are well known by the skilled person in the art, all the salts in the prior art can be prepared by the skilled person in the art. In addition, the skilled person can take some salts instead of other salts based on factors, such as solubility, stability, easy preparation, etc. The determination and optimization of the salts are within experiences of the skilled person.

In the present invention, THF represents tetrahydrofuran, DCC represents dicyclohexylcarbodiimide, DMAP represents 4-dimethylaminopyridine, HCl-AcOE represents ethyl acetate solution saturated by hydrochloric acid, DCM represents dichloromethane, EDCI represents 1-(3-Dimethylaminopropyl)-3-ethylcarbodiimide hydrochloride, HOBt represents 1-hydroxybenzotriazole, PPTS represents pyridinium 4-toluenesulfonate, DHP represents 3,4-dihydro-2H-pyran, Pd/C, $H_2$ represents palladium carbon hydrogen, $(Boc)_2O$ represents di-tert-butyl dicarbonate.

The preparation method of the multi-targeted ubenimex pro-drug derivative according to the present invention includes: 5-fluorouracil is reacted with an aldehyde 1-1 to provide intermediate 2', intermediate 2' is reacted with Boc-L-leucine via condensation reaction to give intermediate 3', protecting group of intermediate 3' is removed to provide compound 4', compound 4' is reacted with Boc-AHPA via condensation reaction to give compound 5', compound 5' is deprotected to give target compound 6'; the specific synthesis route thereof is as follows:

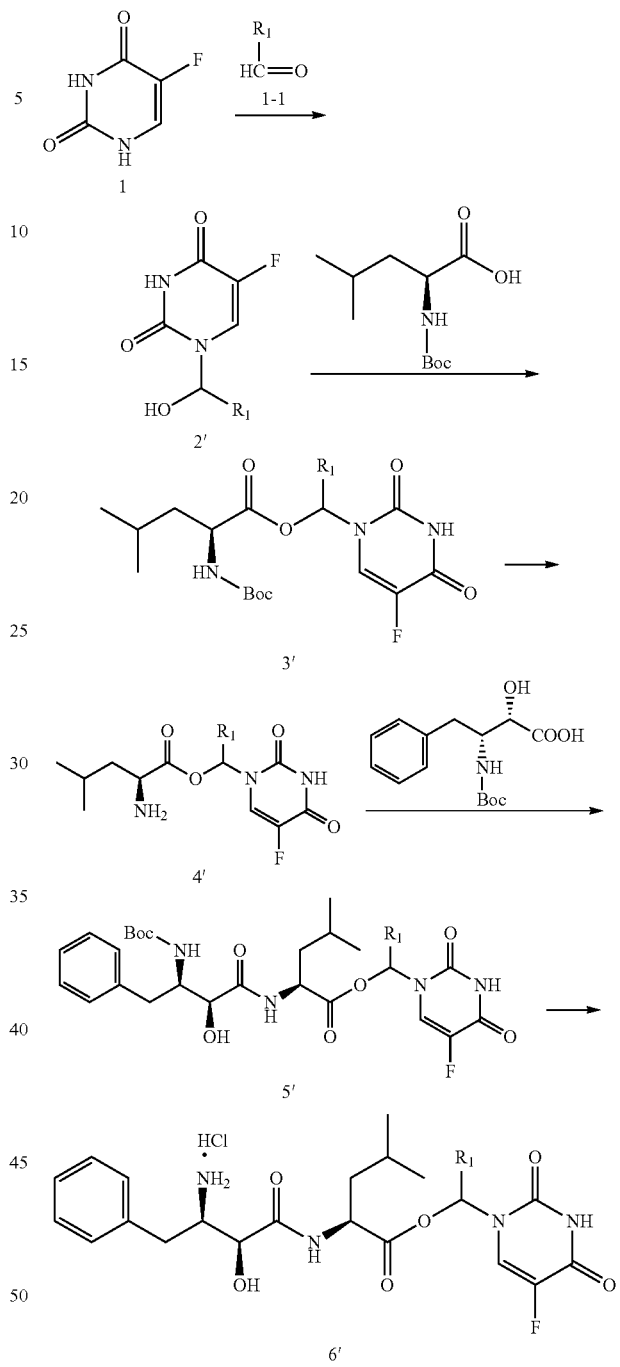

wherein, $R_1$ represents: H, $CH_3$, or $CH_2CH_3$.

Specifically, for example, the synthesis process of BC-01 (the skilled in the art can prepare other compound 6' based on the following synthesis process of BC-01) includes: 5-fluorouracil is reacted with 37% formaldehyde solution to provide intermediate 2, intermediate 2 is reacted with Boc-L-leucine via condensation reaction to give intermediate 3, protecting group of intermediate 3 is removed to provide compound 4, compound 4 is reacted with Boc-AHPA via condensation reaction to give compound 5, compound 5 is deprotected to give target compound 6 (BC-01); the specific synthesis route thereof is as follows:

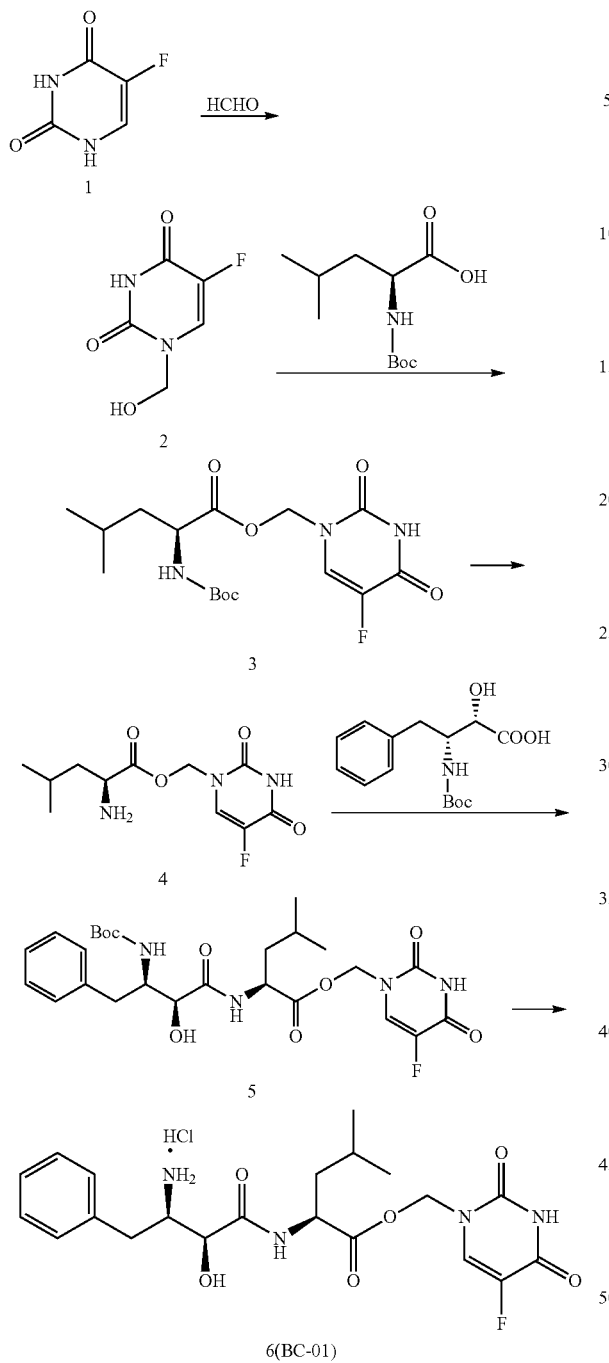

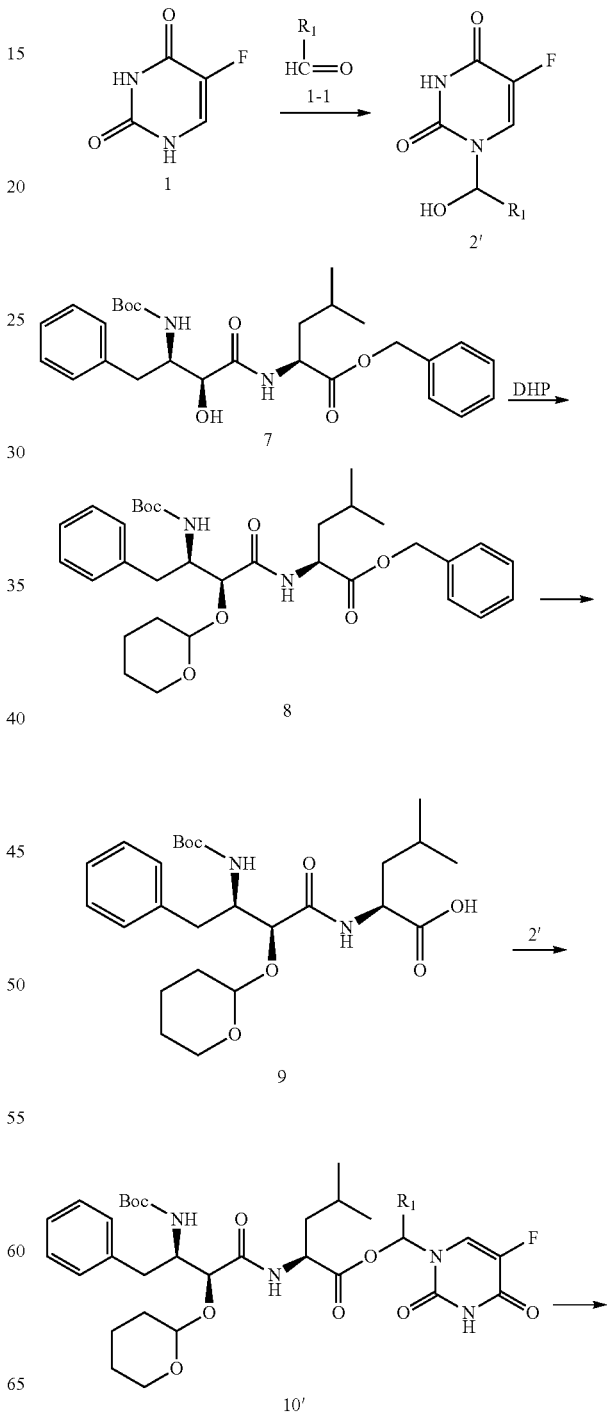

The preparation method of the multi-targeted ubenimex pro-drug derivative according to the present invention includes: 5-fluorouracil is reacted with an aldehyde 1-1 to provide intermediate 2'; the hydroxyl group of compound 7 is protected by DHP to give intermediate 8, the benzyl group of intermediate 8 is removed to provide compound 9, compound 9 is condensed with intermediate 2' to give compound 10', compound 10' is deprotected via acid to provide target compound 6'; the specific synthesis route thereof is as follows:

More specifically, 5-fluorouracil is dissolved in 37% formaldehyde solution to have a reaction at room temperature to provide intermediate 2, intermediate 2 dissolved in anhydrous THF is reacted with Boc-L-leucine in presence of catalyst DCC and DMAP to give intermediate 3, protecting group of intermediate 3 is removed in HCl-AcOE solution to provide compound 4, compound 4 is condensed with Boc-AHPA via EDCl and HOBt in anhydrous DCM to give compound 5, compound 5 is deprotected via ethyl acetate saturated by hydrochloric acid to give target compound 6 (BC-01).

Any specific conditions of each reaction in the synthesis route above can be routine reaction conditions known in the art.

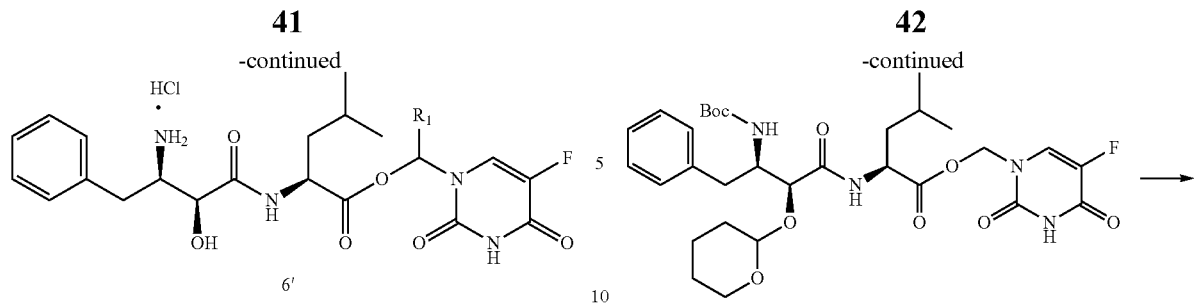

wherein, $R_1$ represents: H, $CH_3$, or $CH_2CH_3$, DHP represents 3,4-dihydro-2H-pyran.

Specifically, for example, the synthesis process of BC-01 (the skilled in the art can prepare other compound 6' based on the following synthesis process of BC-01) includes: 5-fluorouracil is reacted with 37% formaldehyde solution to provide intermediate 2, the hydroxyl group of compound 7 is protected by DHP to give intermediate 8, the benzyl group of intermediate 8 is removed to provide compound 9, compound 9 is condensed with intermediate 2 to give compound 10, compound 10 is deprotected via acid to provide target compound 6 (BC-01); the specific synthesis route thereof is as follows:

More specifically, 5-fluorouracil is dissolved in 37% formaldehyde solution to have a reaction at room temperature to provide intermediate 2, the hydroxyl group of compound 7 dissolved in anhydrous DCM is protected to give intermediate 8 by reacting with DHP and PPTS, the benzyl group of intermediate 8 is removed to provide compound 9 by being treated with Pd/C in $H_2$, compound 9 is condensed with intermediate 2 via EDCl and HOBt in anhydrous DCM to give compound 10, compound 10 is deprotected via ethyl acetate saturated by hydrochloric acid to give target compound 6 (BC-01).

Any specific conditions of each reaction in the synthesis route above can be routine reaction conditions known in the art.

The preparation method of the multi-targeted ubenimex pro-drug derivative according to the present invention includes: compound 14' or its cationic salt is condensed with compound 9 via EDCl and HOBt in anhydrous DCM to give compound 15', compound 15' is deprotected via acid to give target compound 16'; the specific synthesis route thereof is as follows:

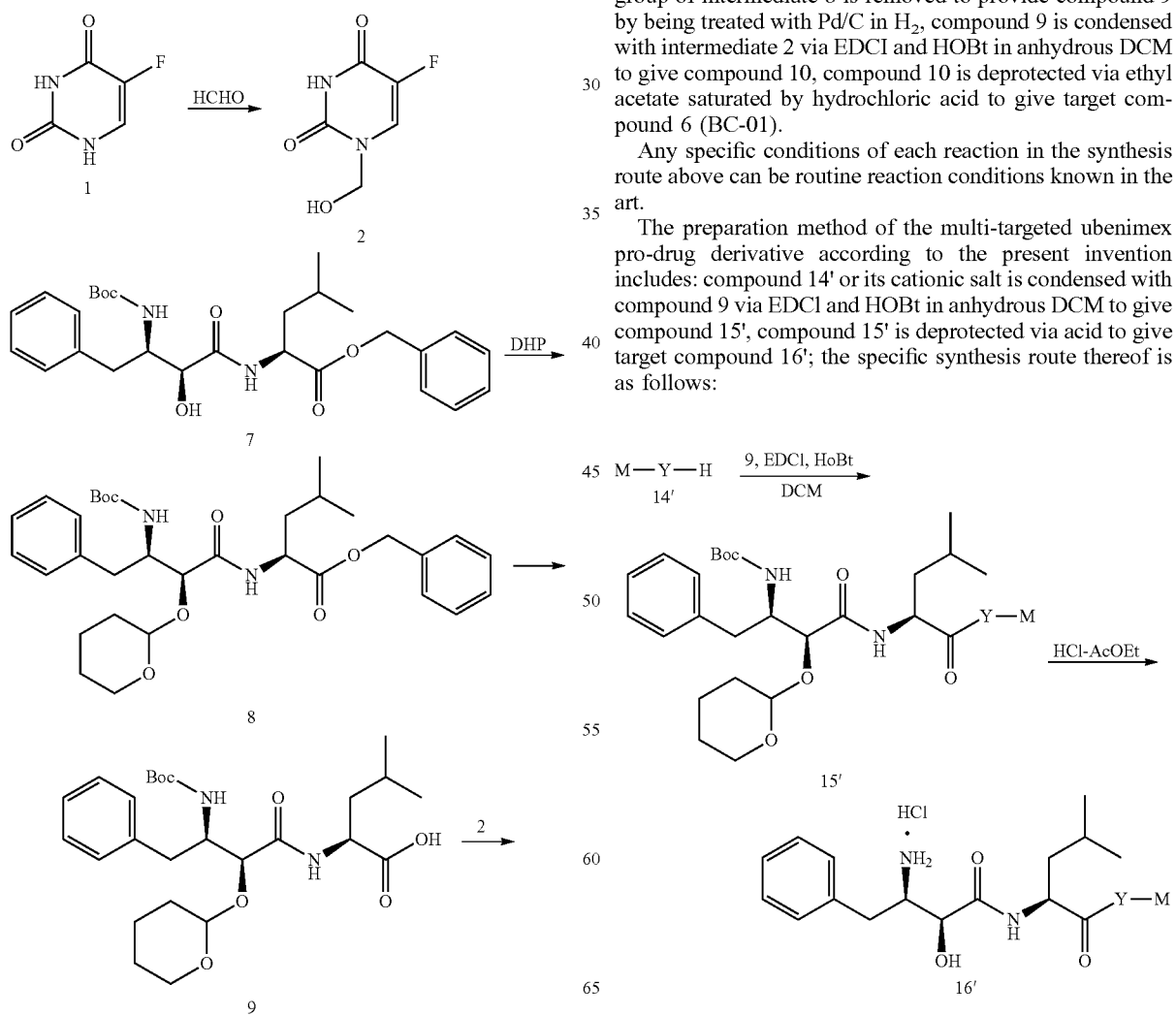

wherein, compound 9 represents

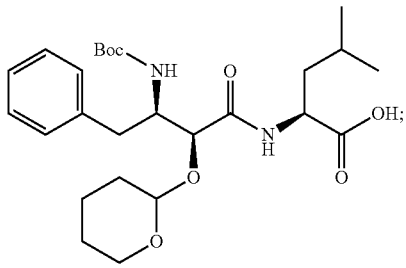

wherein, compound 14' represents

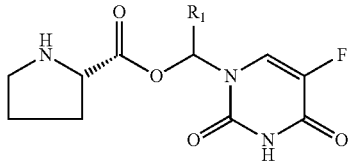

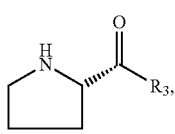

alternatively in compound 14', Y represents O or NH, M represents:

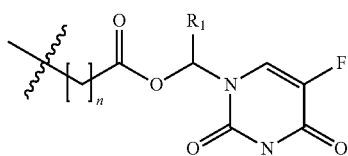

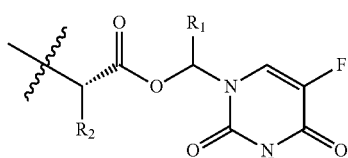

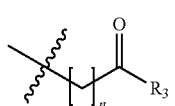

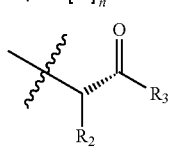

wherein, n, $R_1$, $R_2$ and $R_3$ are defined as above. Preferred cationic salt is hydrochloride.

when Y represents NH and M represents

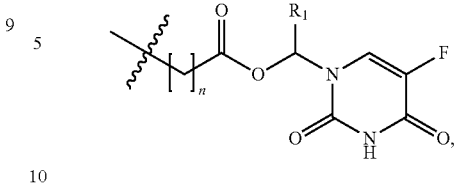

the preparation method of compound 14' comprises: L-glycine 11 is protected via $(Boc)_2O$ to give the compound 12, compound 12 is condensed with compound 2' to give compound 13', compound 13' is deprotected via acid to give target compound 14',

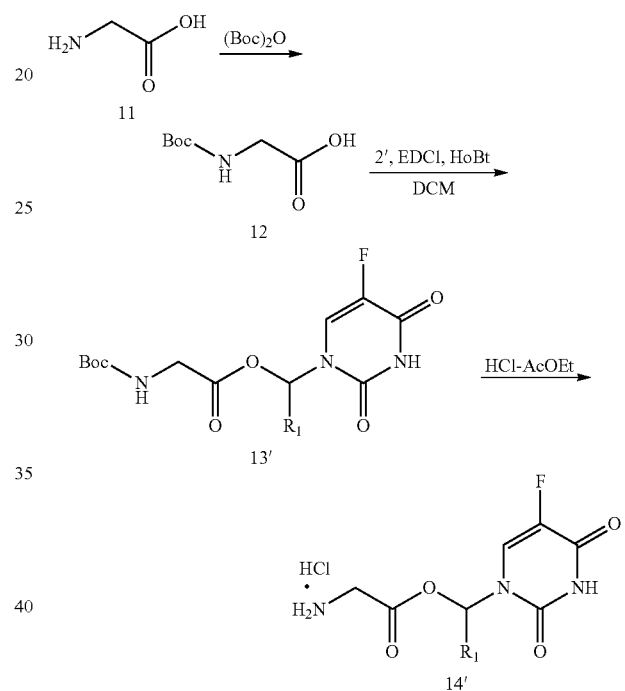

wherein compound 2' represents

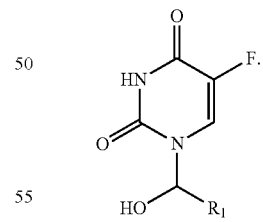

Specifically, for example, the synthesis process of BC-02 (the skilled in the art can prepare other compound 16' based on the following synthesis process of BC-02) includes: L-glycine is protected via $(Boc)_2O$ to give the compound 12, compound 12 is condensed with compound 2 to give compound 13, compound 13 is deprotected via acid to give target compound 14, compound 14 is condensed with compound 9 to give compound 15, compound 15 is deprotected via acid to give target compound 16 (BC-02). The specific synthesis route thereof is as follows:

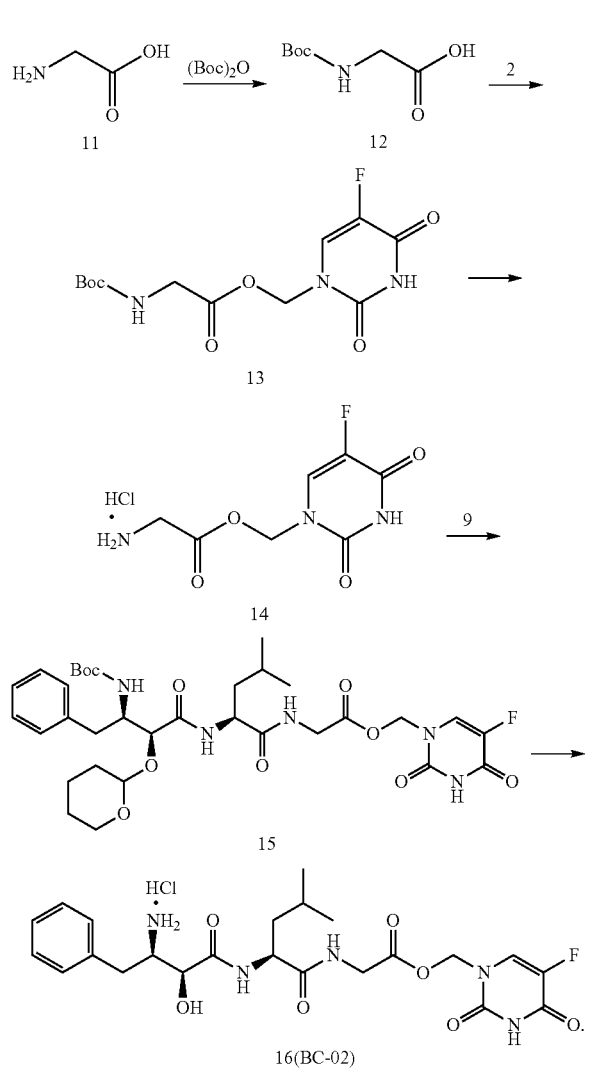

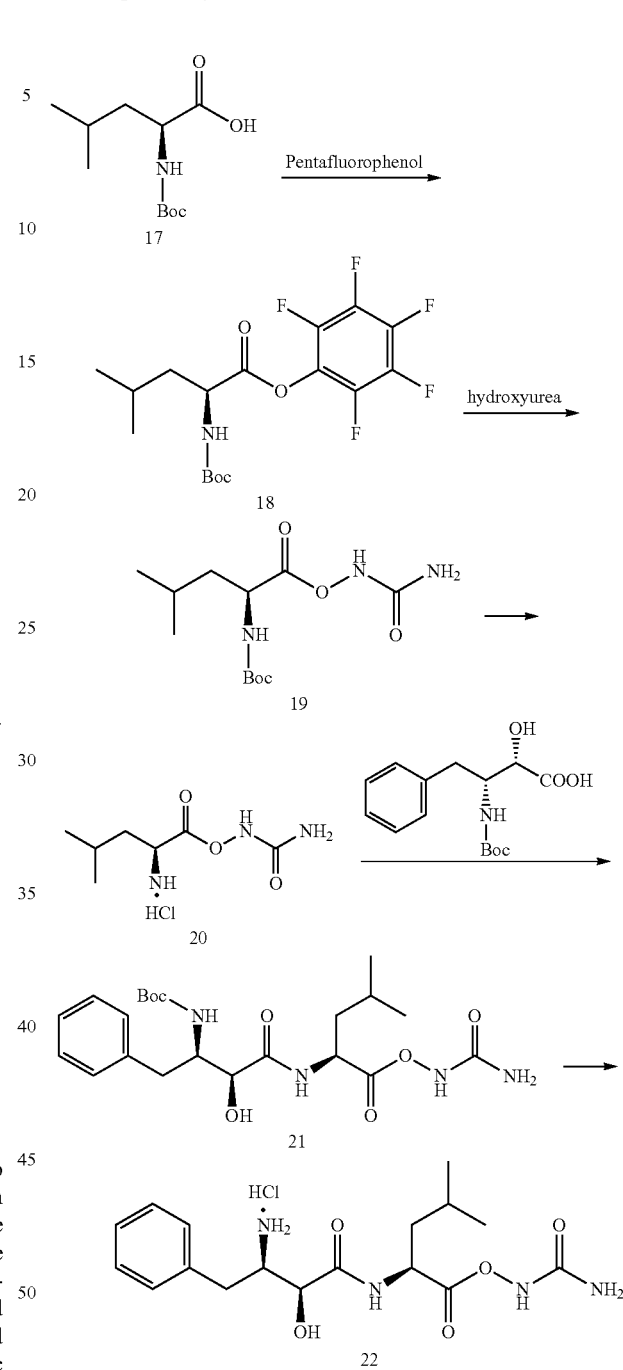

the specific synthesis route thereof is as follows:

More specifically, L-glycine is protected via (Boc)₂O to give the compound 12, compound 12 is condensed with compound 2 via EDCl and HOBt in anhydrous DCM to give compound 13, compound 13 is deprotected via ethyl acetate saturated by hydrochloric acid to give compound 14, compound 14 is condensed with compound 9 via EDCl and HOBt in anhydrous DCM to give compound 15, compound 15 is deprotected via ethyl acetate saturated by hydrochloric acid to give target compound 16 (BC-02).

Any specific conditions of each reaction in the synthesis route above can be routine reaction conditions known in the art.

The preparation method of the multi-targeted ubenimex pro-drug derivative according to the present invention includes: Boc-L-Leucine 17 is condensed with pentafluorophenol to give intermediate 18, intermediate 18 is reacted with hydroxyurea to provide compound 19, protecting group of compound 19 is removed via acid to give compound 20, compound 20 is condensed with Boc-AHPA to give compound 21, compound 21 is deprotected to provide target compound 22;

More specifically, Boc-L-Leucine dissolved in anhydrous THF is reacted with pentafluorophenol in presence of EDCI to give intermediate 18, compound 19 was provided from compound 18 in presence of N-methylmorpholine, protecting group of compound 19 is removed in ethyl acetate solution saturated by hydrochloric acid to give compound 20, compound 20 is condensed with via EDCl and HOBt in anhydrous DCM to give compound 21, compound 21 is deprotected via ethyl acetate saturated by hydrochloric acid to give target compound 22.

Any specific conditions of each reaction in the synthesis route above can be routine reaction conditions known in the art.

The preparation method of the multi-targeted Ubenimex pro-drug derivative according to the present invention includes: Epirubicin is protected via (Boc)₂O to give compound 24, compound 24 is condensed with Cbz-L-leucine to give compound 25, an amino-protecting group of compound 25 is removed to give compound 26, compound 26 is condensed with Boc-AHPA to give compound 27, compound 27 is deprotected to give target compound 28; the specific synthesis route thereof is as follows:

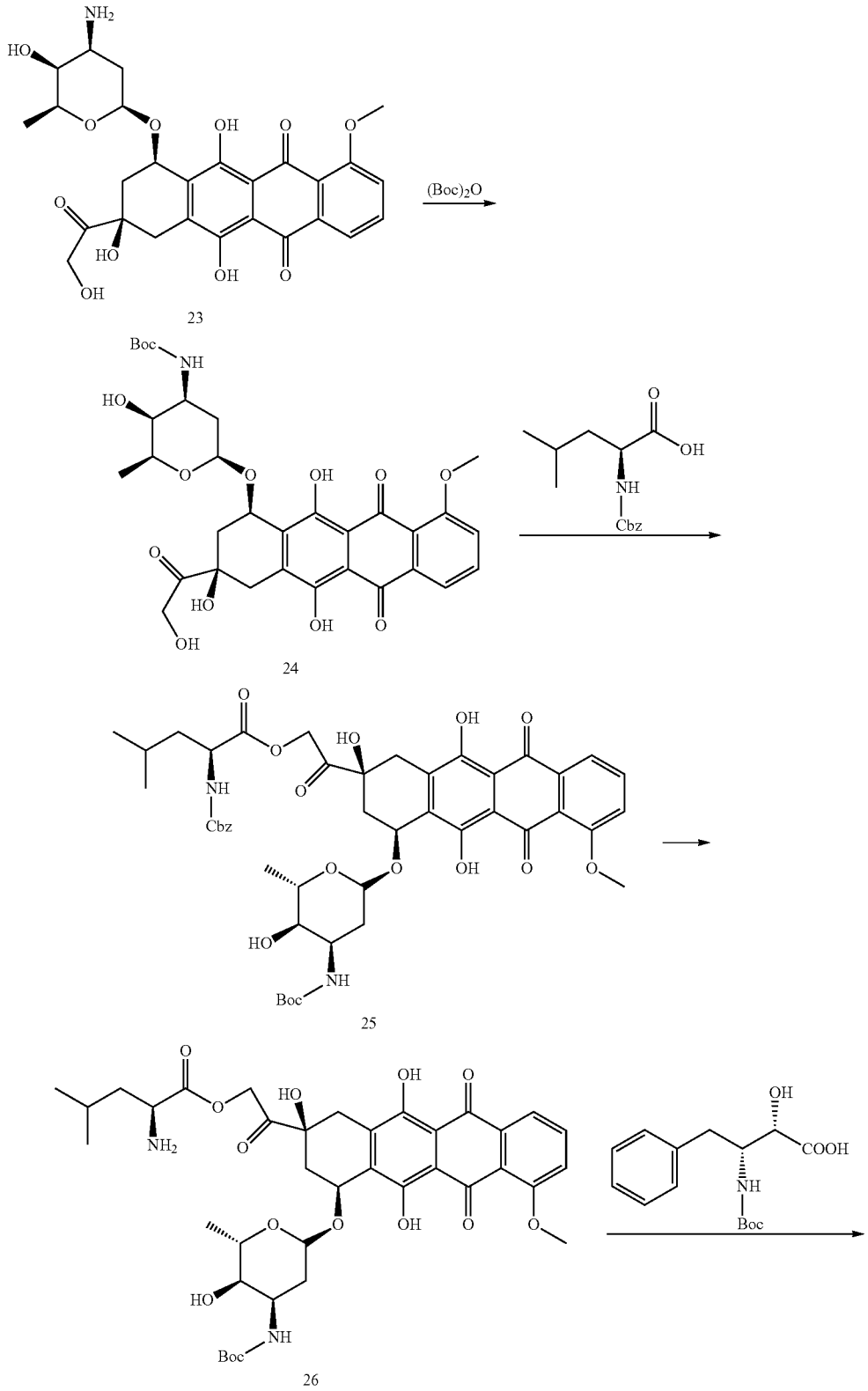

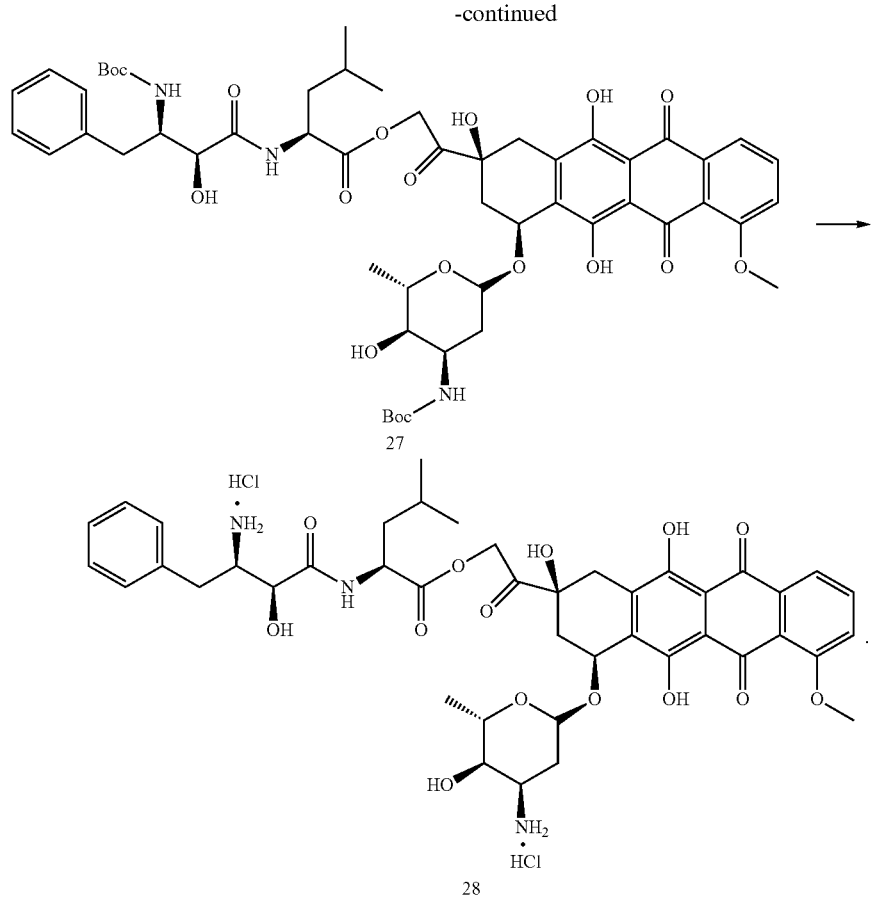

More specifically, Epirubicin is protected via (Boc)₂O to give compound 24, compound 24 is condensed with Cbz-L-leucine via EDCI and HOBt in anhydrous DCM to give compound 25, the amino-protecting group of compound 25 is removed by palladium carbon hydrogen to give compound 26, compound 26 is condensed with Boc-AHPA via EDCI and HOBt in anhydrous DCM to give compound 27, compound 27 is deprotected via ethyl acetate saturated by hydrochloric acid to give target compound 28.

Any specific conditions of each reaction in the synthesis route above can be routine reaction conditions known in the art.

The preparation method of the multi-targeted ubenimex pro-drug derivative according to the present invention includes: Boc-L-leucine 17 is condensed with compound A-E-H to give compound 29', compound 29' is deprotected via acid to give compound 30', compound 30' is condensed with Boc-AHPA to give compound 31', compound 31' is deprotected to give target compound 32'; the specific synthesis route thereof is as follows:

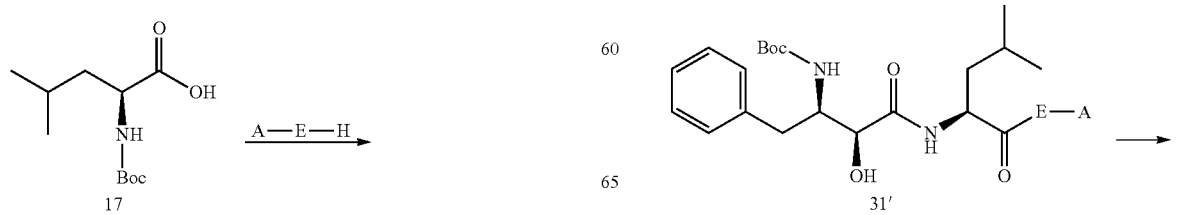

51
-continued

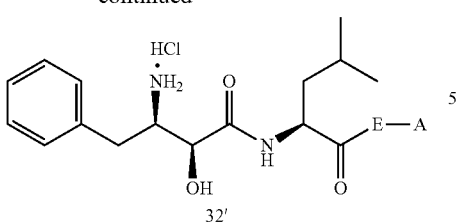
32' wherein, A-E-H represents

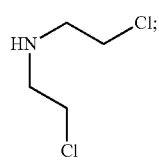

or E represents NH or O, A represents:

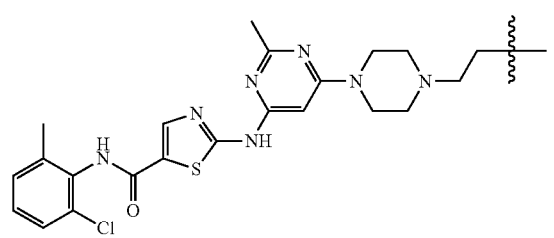

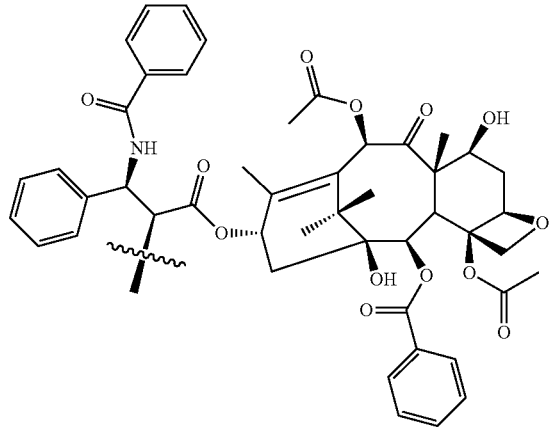

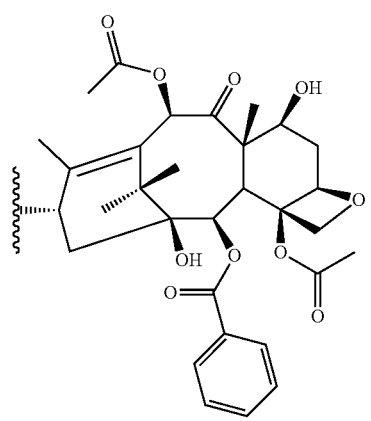

52
-continued

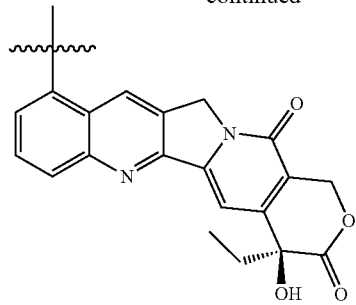

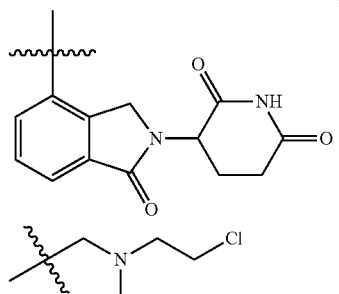

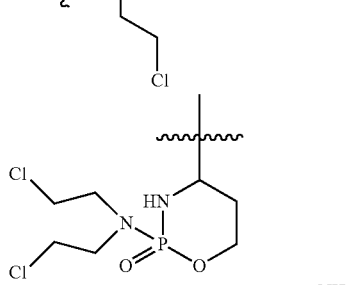

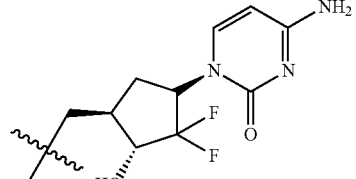

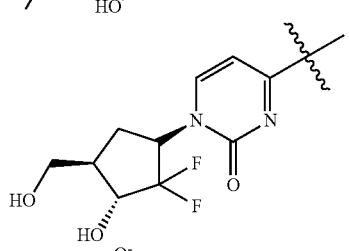

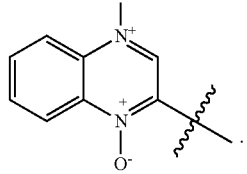

Specifically, for example, the synthesis process of dasatinib derivative 32 (the skilled in the art can prepare other compound 32' based on the following synthesis process of dasatinib derivative 32) includes: Boc-L-leucine is condensed with dasatinib to give compound 29, compound 29 is deprotected via acid to give compound 30, compound 30 is condensed with Boc-AHPA to give compound 31, compound 31 is deprotected to give target compound 32; the specific synthesis route thereof is as follows:

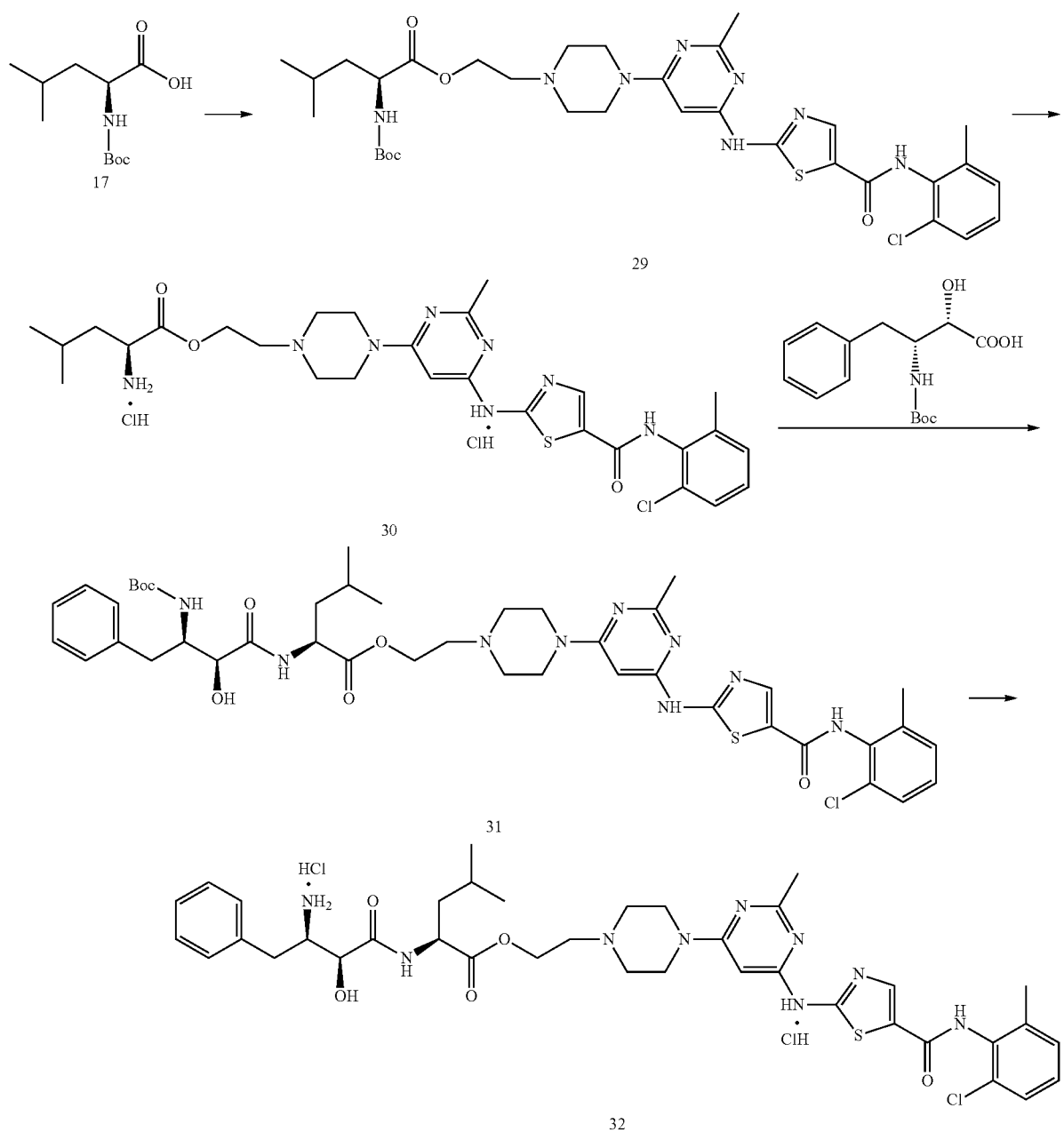

More specifically, Boc-L-leucine is condensed with dasatinib via EDCl and HOBt in anhydrous DCM to give compound 29, compound 29 is deprotected via ethyl acetate saturated by hydrochloric acid to give compound 30, compound 30 is condensed with Boc-AHPA via EDCl and HOBt in anhydrous DCM to give compound 31, compound 31 is deprotected via ethyl acetate saturated by hydrochloric acid to give target compound 32.

Any specific conditions of each reaction in the synthesis route above can be routine reaction conditions known in the art.

The preparation method of the multi-targeted ubenimex pro-drug derivative according to the present invention includes: compound 9 is condensed with Q-Y-H to give target compound 33;

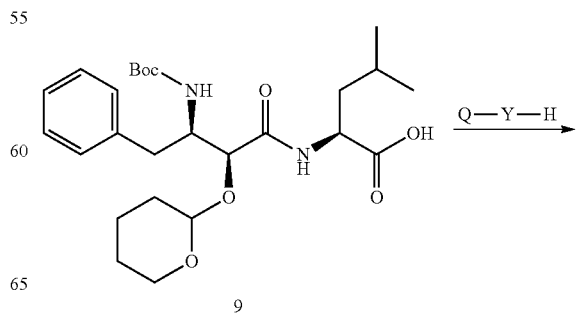

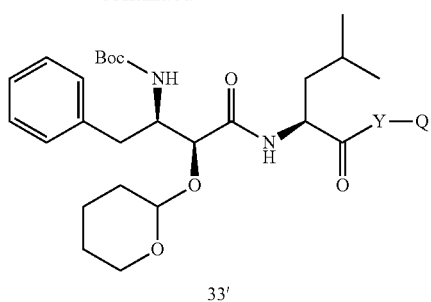

33' wherein, in Q-Y-H, Y represents NH or O, Q represents:

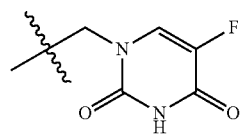

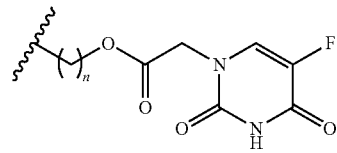

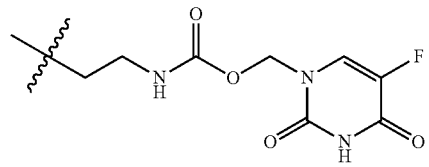

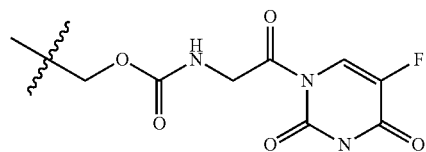

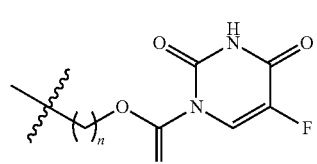

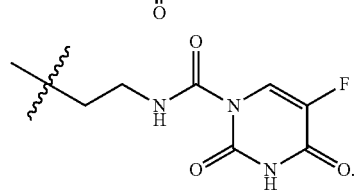

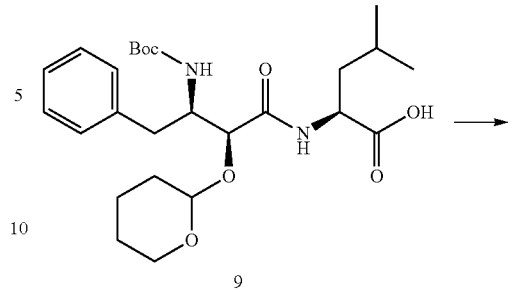

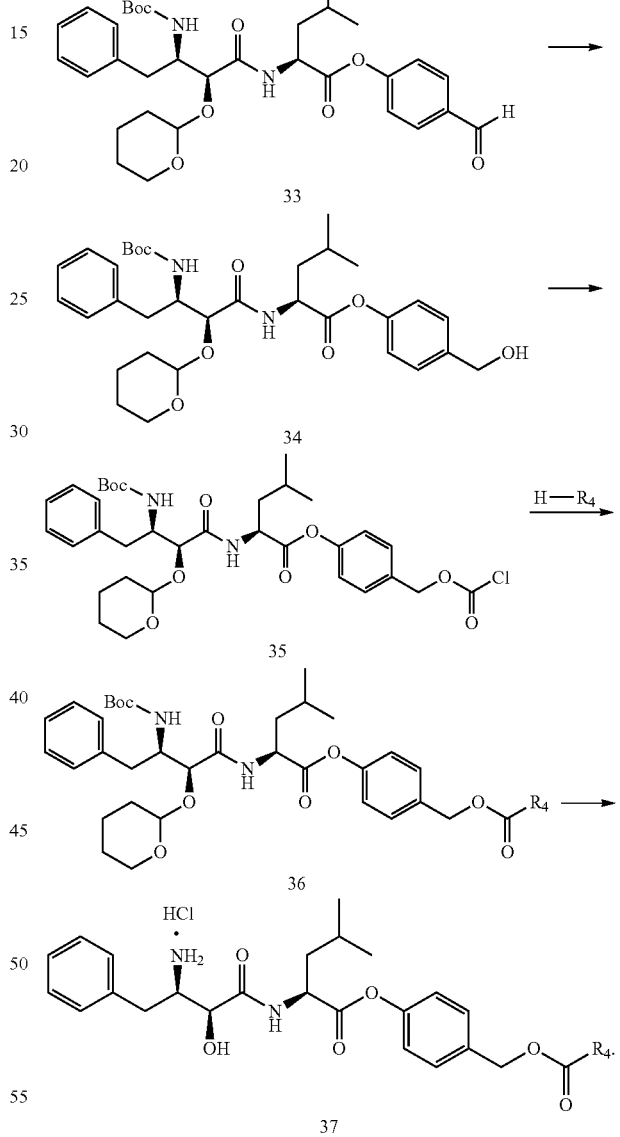

Specifically, the preparation method of the multi-targeted ubenimex pro-drug derivative according to the present invention includes: compound 9 is condensed with p-hydroxybenzaldehyde to give compound 33, compound 33 is reduced to give alcohol 34, alcohol 34 is reacted with triphosgene to give compound 35, compound 35 is reacted with H—$R_4$ to form compound 36, compound 36 is deprotected to give target compound 37; the specific synthesis route thereof is as follows:

In the present invention, the drugs and simple derivatives thereof, for binding with ubenimex, can be prepared by method known in the art.

The multi-targeted ubenimex pro-drug derivative in the present invention can be used to treat or prevent a variety of tumors, especially be used as a drug for solid tumors resistant to chemotherapy drugs, and especially be used as anti-malignant tumor (especially the solid tumors) drugs in medical field.

The multi-targeted ubenimex pro-drug derivative in the present invention can be used to treat or prevent a variety of tumors. Wherein, the tumors represent solid tumors resistant to chemotherapy drugs preferably.

According to the pro-drug principle and hybridization principle, the present invention has the structural framework of ubenimex be modified but retaining its group which can chelate with zinc iron so that to find out a novel anti-tumor drug. We designed and synthesized a series of novel mutual pro-drugs by blending a CD13 inhibitor ubenimex into the molecular structure of another marketed drug (such as 5-FU, hydroxyurea, epirubicin, dasatinib, and paclitaxel) through an ester bond or an amido bond by using pharmacophore hybridization method. These pro-drugs retain an inhibition activity against CD13, which will play a targeted anti-cancer role on inhibiting tumor stem cells by inhibiting CD13 after these CD13 inhibitors entering into body. In addition, These pro-drugs would be metabolized in presence of esterase catalyst in vivo to release ubenimex and another anti-cancer dung fragment, and ubenimex keeps targeting CD13 to inhibit stem cells, on the other hand, another released anti-cancer drug fragment performs its special pharmacodynamic effect, so as to realize a synergistic anti-cancer effect of two drugs, then to improve anti-tumor activity effectively. Furthermore, all the mutual pro-drugs designed by us are salts which can improve water solubility, and be suitable to oral and intravenous administration, while can improve the bioavailability of the two drugs. What's more, the anti-cancer drugs (such as 5-FU, hydroxyurea, epirubicin, dasatinib, paclitaxel, gemcitabine, and hydroxycamptothecine) we selected are broad-spectrum anti-cancer drugs wildly used in clinic and have a good therapeutic effect on treating liver cancer. In a broad sense, therefore, we expect the mutual drug can prolong residence time of its two drugs in vivo, and improve its pharmacokinetic properties and its bioavailability. The pro-drugs in the present invention could improve anti-tumor activity by the synergistic effect between ubenimex, which can inhibit tumor stem cells and angiogenesis of tumor microenvironment, and other anti-cancer drugs such as 5-FU with cytotoxicity, especially have anti-recurrence and anti-metastasis effect by inhibiting tumor stem cells.

DETAILED DESCRIPTION OF THE EMBODIMENTS

Figure 1:
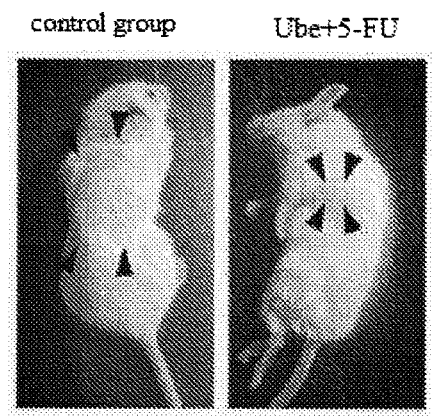
FIG. 1 illustrates the tumor size of control mice and combination of ubenimex and 5-FU treated mice.
Figure 2:
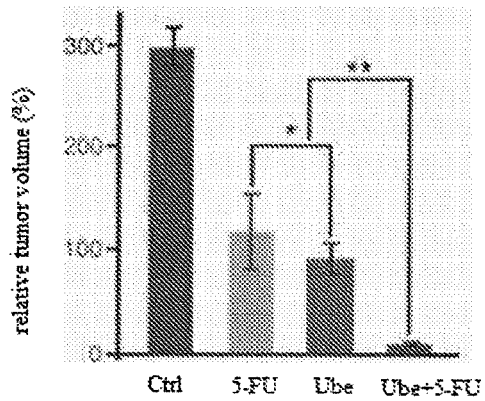
FIG. 2 illustrates the tumor volume of Kunming mice.

The following examples are served to exemplify the present invention, but not to limit the scope of the invention.

EXAMPLE 1

Preparation of 5-fluoro-1-hydroxymethylpyrimidine-2,4(1H,3H)-dione (2)

5-FU (0.26 g, 2 mmol) was dissolved in 1 mL of 37% formaldehyde solution and the mixture was reacted at 60° C. for 2 h under oil bath. After evaporating the solvent under reduced pressure, the residue was dried under vacuum to get colorless viscous oil 2 (0.3 g, yield: 94%).

EXAMPLE 2

Preparation of (S)-(5-fluoro-2,4-dioxo-3,4-dihydropyrimidinyl-1(2H))methyl-2-((tert-butoxycarbonyl)amino)-4-methylpentanoate (3)

2 (0.3 g, 1.9 mmol) was dissolved in acetonitrile, followed by adding Boc-L-leucine (0.7 g, 2.8 mmol), DCC (0.6 g, 2.8 mmol) and DMAP (0.03 g) into it while stirring under ice bath. After the ice bath was removed, the obtained mixture was stirred at room temperature for 12 h. Filtered and evaporated the solvent, extracted with ethyl acetate, the organic phase was washed with water, 1 M citric acid, saturated sodium bicarbonate and saturated sodium chloride solution in turn. Dried with anhydrous sodium sulfate, filtered it and evaporated the solvent to get colorless oil 3 (0.42 g, 60%).

EXAMPLE 3

Preparation of (S)-(5-fluoro-2,4-dioxo-3,4-dihydropyrimidinyl-1(2H))methyl-2-(amino)-4-methylpentanoate hydrochloride (4)

3 (0.37 g, 1.0 mmol) was dissolved in ethyl acetate solution saturated by chloride hydrogen, and the solution was reacted at room temperature for 2 h. Filtered the solution then to get white powder 4 (0.26 g, 83%).

EXAMPLE 4

Preparation of (S)-(5-fluoro-2,4-dioxo-3,4-dihydropyrimidinyl-1(2H))methyl-2-((2S,3R)-3-((tert-butoxycarbonyl)amino)-2-hydroxy-4-phenylbutyryl)-4-methylpentanoate (5)

Boc-AHPA (0.3 g, 1.0 mmol) was dissolved in anhydrous dichloromethane, and followed by the addition of EDCI (0.3 g, 1.5 mmol) and HOBt (0.2 g, 1.5 mmol) under ice bath, after stirring for 0.5 h, 4 (0.3 g, 1 mmol) and 0.2 mL of triethylamine were added into the solution. The mixture was reacted for 5 h at room temperature after the ice bath was removed. After the reaction was accomplished, the organic layer was washed with water, 1 M citric acid, saturated sodium bicarbonate and saturated sodium chloride solution respectively, then dried with anhydrous sodium sulfate, filtered it and evaporated the solvent to get white solid 5 (0.33 g, 55%).

EXAMPLE 5

Preparation of (S)-(5-fluoro-2,4-dioxo-3,4-dihydropyrimidinyl-1(2H))methyl-2-((2S,3R)-3-(amino)-2-hydroxy-4-phenylbutyryl)-4-methylpentanoate hydrochloride (6(BC-01))

5 (0.33 g, 0.55 mmol) was dissolved in ethyl acetate solution saturated by chloride hydrogen, and the solution was reacted at room temperature for 2 h. Filtered it to get white solid 6(BC-01) (0.23 g, 85%). ESI-MS m/z:451.6 (M+H)$^+$, $^1$H-NMR (600 MHz DMSO): δ 0.84-0.87 (m, 6H), 1.53 (m, 1H), 1.60-1.68 (m, 2H), 2.89-2.95 (m, 2H), 3.99-4.03 (m, 2H), 4.25 (m, 1H), 5.56-5.61 (m, 2H), 6.80 (s, 1H), 7.26-7.35 (m, 5H), 8.04 (s, 3H), 8.13 (d, J=6.6 Hz, 1H), 8.47 (d, J=7.2 Hz, 1H), 12.01 (s, 1H). mp: 128-130° C.

EXAMPLE 6

Preparation of (S)-benzyl-2-((2S,3R)-3-((tert-butoxycarbonyl)amino)-2-hydroxy-4-phenylbutyryl)-4-methylpentanoate (7)

Boc-AHPA (6 g, 20.3 mmol) was dissolved in dichloromethane, and followed by the addition of HOBt (3 g, 22.3 mmol) and EDCI (4.5 g, 22.3 mmol) under ice bath. And after 0.5 h, L-leucine benzyl ester toluene-4-sulfonate (8.5 g, 22.3 mmol) and 3.1 mL of triethylamine were added into the solution. The mixture was reacted for 5 h after the ice bath was removed. The reactant solution was washed with 10% citric acid, saturated NaHCO$_3$ and saturated NaCl for 3 times respectively, then dried with anhydrous sodium sulfate. Filtered it and evaporated the solvent to achieve a yellowish white solid 7 (4.8 g, 47.5%).

EXAMPLE 7

Preparation of (2S)-benzyl-2-((2S,3R)-3-((tert-butoxycarbonyl)amino)-4-phenyl-2-(2-(2H)-tetrahydropyranoxy)butyryl)-4-methylpentanoate (8)

7 (12 g, 24 mmol) was dissolved in dry dichloromethane, followed by addition of PPTS (0.6 g, 2.4 mmol) and DHP (3.6 g, 43.2 mmol) dropwise. The mixture was reacted at 35° C. for 24 h until TLC test gave the reaction was accomplished, 0.5 g of K$_2$CO$_3$ were added, and the mixture was stirred for 20 min, then the solution was washed with saturated NaCl for three times. After dried with anhydrous sodium sulfate, filtered it and evaporated the solvent under reduced pressure to get yellowish white solid 8 (12.6 g, 90.8%).

EXAMPLE 8

Preparation of (2S)-2-((2S,3R)-3-((tert-butoxycarbonyl)amino)-4-phenyl-2-(2-(2H)-tetrahydropyranoxy)butyryl)-4-methylpentanoate (9)

8 (12.6 g, 21.6 mmol) was dissolved in methanol, then 1.3 g Pd/C (10%) was added in several times. The air in the reactant bottle was removed out and was filled with hydrogen by a hydrogen balloon, after being reacted for 12 h, filtered the mixture with two layers of filter papers. The solvent was evaporated until the residue was dried to get colorless foam like solid 9 (10.2 g, 96.0%).

EXAMPLE 9

Preparation of (S)-(5-fluoro-2,4-dioxo-3,4-dihydropyrimidinyl-1(2H))methyl-2-((2S,3R)-3-((tert-butoxycarbonyl)amino)-4-phenyl-2-(2-(2H)-tetrahydropyranoxy)acyl)-4-methylpentanoate (10)

9 (6 g, 20.3 mmol) was dissolved in re-distilled dichloromethane, followed by addition of HOBt (3.6 g, 26.92 mmol) and EDCI (5.2 g, 26.92 mmol) under ice bath. After 0.5 h, 2 (4.3 g, 26.92 mmol) in acetonitrile solution and 3.7 mL of triethylamine were added into the solution, and the mixture was reacted for 20 h after the ice bath was removed. The reactant solution was washed with 10% citric acid, saturated NaHCO$_3$ and saturated NaCl for three times, and dried with anhydrous sodium sulfate. Filtered it and evaporated the solvent to get yellow oil, and separated the oil by using flash column chromatography to obtain colorless oil 10 (8.8 g, 67%).

EXAMPLE 10

Preparation of (S)-(5-fluoro-2,4-dioxo-3,4-dihydropyrimidinyl-1(2H))methyl-2-((2S,3R)-3-(amino)-2-hydroxy-4-phenylbutyryl)-4-methylpentanoate hydrochloride (6(BC-01))

10 (8.8 g, 13.9 mmol) was dissolved in ethyl acetate solution saturated by chloride hydrogen, and let the solution react at room temperature for 2 h. Filtered it to get white solid 6(BC-01) (5.94 g, 88%). ESI-MS m/z:451.5 (M+H)$^+$, $^1$H-NMR (600 MHz DMSO): δ 0.85-0.89 (m, 6H), 1.51-1.56 (m, 1H), 1.59-1.66 (m, 2H), 2.87-2.94 (m, 2H), 4.01-4.05 (m, 2H), 4.24-5.28 (m, 1H), 5.60-5.63 (m, 2H), 6.75 (s, 1H), 7.23-7.32 (m, 5H), 8.09 (s, 3H), 8.16 (d, J=6.6 Hz, 1H), 8.48 (d, J=7.2 Hz, 1H), 12.05 (s, 1H). mp: 128-129° C.

EXAMPLE 11

Preparation of 2-((tert-butoxycarbonyl)amino)acetic acid (12)

L-Glycine (2.3 g, 30 mmol) was dissolved in 1 mol/L NaOH, and (Boc)$_2$O (7.2 g, 33 mmol) in tetrahydrofuran solution was added into the mixture dropwise while stirring mechanically under ice bath. After finishing adding and for 0.5 h, the ice bath was removed. The pH of the reactant solution was retained at 10 by using 2 mol/L NaOH, and then reacted overnight. After tetrahydrofuran was evaporated, the residue was extracted with petroleum ether for 3 times, and the pH of water phase was adjusted to 2-3 by using 3 mol/L HCl, and then extracted it with ethyl acetate, dried with anhydrous sodium sulfate. After filtering, evaporating and being dried for 24 h in vacuum, a white solid 12 (5.1 g, 96%) was obtained.

EXAMPLE 12

Preparation of (5-fluoro-2,4-dioxo-3,4-dihydropyrimidinyl-1-(2H))methyl-2-((tert-butoxycarbonyl)amino)acetate (13)

12 (1.1 g, 6.3 mmol) was dissolved in re-distilled dichloromethane, followed by addition of HOBt (1.2 g, 8.8 mmol)

and EDCI (1.7 g, 8.8 mmol) under ice bath. After 0.5 h, 2 (1.4 g, 8.8 mmol) in acetonitrile solution and 1.2 mL of trimethylamine were added into the solution, and the mixture was reacted for 20 h after the ice bath was removed. The reactant solution was washed with 10% citric acid, saturated NaHCO$_3$ and saturated NaCl for three times, and dried with anhydrous sodium sulfate. Filtered it and evaporated the solvent to get yellow oil, and separated the oil by using flash column chromatography to obtain colorless oil 13 (1.3 g, 67%).

EXAMPLE 13

Preparation of (5-fluoro-2,4-dioxo-3,4-dihydropyrimidinyl-1-(2H))methyl-2-amino)acetate hydrochloride (14)

13 (1.3 g, 4.2 mmol) was dissolved in ethyl acetate solution saturated by chloride hydrogen, and the solution was reacted at room temperature for 3 h. Filtered it to give a white solid 14 (0.93 g, 88%).

EXAMPLE 14

Preparation of (6R,7S,10S)-(5-fluoro-2,6-dioxo-1,2,3,6-tetrahydropyrimidin-3-yl)methyl-6-benzyl-10-isobutyl-2,2-dimethyl-4,8,11-trioxo-7-(2-2H-tetrahydropyranoxy)-3-oxo-5,9,12-triazatetradecanoate (15)

9 (1.21 g, 2.45 mmol) was dissolved in anhydrous dichloromethane, followed by addition of EDCI (0.65 g, 3.4 mmol) and HOBt (0.46 g, 3.4 mmol) under ice bath, and after 0.5 h, 14 (0.93 g, 3.4 mmol) and 0.48 mL of triethylamine were added into the solution. The mixture was reacted for 5 h at room temperature after the ice bath was removed. Until the reaction was accomplished, evaporated the solvent and its residue was separated by column chromatography to obtain white solid 15 (0.86 g, 51%).

EXAMPLE 15

Preparation of (5-fluoro-2,4-dioxo-3,4-dihydropyrimidinyl-1(2H))methyl-2-((S)-2-((2S,3R)-3-amino-2-hydroxy-4-phenylbutanamido)-4-methylpentanamido)acetate hydrochloride (16(BC-02))

15 (0.86 g, 1.24 mmol) was dissolved in ethyl acetate solution saturated by chloride hydrogen, and let the solution react at room temperature for 2 h. Filtered it to get a white solid 16(BC-02) (0.57 g, 85%). ESI-MS m/z:508.4 (M+H)$^+$, $^1$H-NMR (400 MHz DMSO): δ 0.86-0.89 (m, 6H), 1.49-1.53 (m, 2H), 1.62-1.66 (m, 1H), 2.87-2.97 (m, 2H), 3.55-3.57 (m, 1H), 3.80-3.92 (m, 2H), 4.00-4.06 (m, 1H), 4.31-4.32 (m, 1H), 5.57-5.80 (m, 2H), 6.73 (s, 1H), 7.25-7.37 (m, 5H), 8.02-8.08 (m, 4H), 8.14 (d, J=6.6 Hz, 1H), 8.59-8.62 (m, 1H), 12.01 (s, 1H). mp: 136-137° C.

EXAMPLE 16

The following Compounds were prepared as the general procedure as described in BC-02.

(S)-(5-fluoro-2,4-dioxo-3,4-dihydropyrimidinyl-1 (2H))methyl-2-((S)-2-((2S,3R)-3-amino-2-hydroxy-4-phenylbutanamido)-4-methylpentanamido)propanoate hydrochloride (BC-03)

ESI-MS m/z:521.5 (M+H)$^+$, $^1$H-NMR (400 MHz DMSO): δ 0.85-0.91 (m, 6H), 1.25-1.28 (m, 3H), 1.43-1.51 (m, 2H), 1.60-1.64 (m, 1H), 2.87-2.94 (m, 2H), 3.53-3.57 (m, 1H), 3.99-4.04 (m, 1H), 4.24-4.31 (m, 2H), 5.54-5.64 (m, 2H), 7.27-7.34 (m, 5H), 7.98-8.00 (m, 4H), 8.12 (d, J=6.6 Hz, 1H), 8.61 (d, J=6.8 Hz, 1H), 11.99 (s, 1H). mp: 111-112° C.

(5-fluoro-2,4-dioxo-3,4-dihydropyrimidinyl-1(2H)) methyl-4-((S)-2-((2S,3R)-3-amino-2-hydroxy-4-phenylbutanamido)-4-methylpentanamido)propanoate hydrochloride (BC-04)

ESI-MS m/z:522.5 (M+H)$^+$, $^1$H-NMR (400 MHz DMSO): δ 0.84-0.88 (m, 6H), 1.45-1.59 (m, 4H), 2.86-2.97 (m, 2H), 3.20-3.31 (m, 2H), 3.56-3.57 (m, 1H), 4.00-4.06 (m, 1H), 4.18-4.23 (m, 1H), 5.55-5.60 (m, 2H), 7.26-7.36 (m, 5H), 7.99-8.01 (m, 4H), 8.09-8.11 (m, 1H), 8.21-8.24 (m, 1H), 11.96 (s, 1H). mp: 119-120° C.

(5-fluoro-2,4-dioxo-3,4-dihydropyrimidinyl-1(2H)) methyl-6-((S)-2-((2S,3R)-3-amino-2-hydroxy-4-phenylbutanamido)-4-methylpentanamido)butanoate hydrochloride (BC-05)

ESI-MS m/z:536.4 (M+H)$^+$, $^1$H-NMR (400 MHz DMSO): δ 0.85-0.89 (m, 6H), 1.48-1.65 (m, 6H), 2.32-2.36 (m, 2H), 2.89-2.94 (m, 2H), 3.02-3.07 (m, 2H), 3.56-3.57 (m, 1H), 4.01-4.04 (m, 1H), 4.20-4.26 (m, 1H), 5.56-5.62 (m, 2H), 7.27-7.35 (m, 5H), 7.99-8.04 (m, 5H), 8.12-8.15 (m, 1H), 11.96 (s, 1H). mp: 117-118° C.

(5-fluoro-2,4-dioxo-3,4-dihydropyrimidinyl-1(2H)) methyl-4-((S)-2-((2S,3R)-3-amino-2-hydroxy-4-phenylbutanamido)-4-methylpentanamido)hexanoate hydrochloride (BC-06)

ESI-MS m/z:564.5 (M+H)$^+$, $^1$H-NMR (400 MHz DMSO): δ 0.86-0.89 (m, 6H), 1.16-1.24 (m, 2H), 1.36-1.38 (m, 2H), 1.46-1.52 (m, 5H), 2.28-2.32 (m, 2H), 2.89-3.02 (m, 4H), 3.55 (s, 1H), 3.99-4.04 (m, 1H), 4.22-4.26 (m, 1H), 5.56 (s, 2H), 7.27-7.35 (m, 5H), 7.99-8.15 (m, 6H), 11.96 (s, 1H). mp: 98-99° C.

(S)-(5-fluoro-2,4-dioxo-3,4-dihydropyrimidinyl-1 (2H))methyl-1-((S)-2-((2S,3R)-3-amino-2-hydroxy-4-phenylbutanamido)-4-methylpentanamido)-2-tetrahydropyrrolidine carboxylate hydrochloride (BC-07)

ESI-MS m/z:548.4 (M+H)$^+$, $^1$H-NMR (400 MHz DMSO): δ 0.87-0.92 (m, 6H), 1.39-1.41 (m, 1H), 1.46-1.49 (m, 1H), 1.65-1.71 (m, 1H), 1.85-1.99 (m, 2H), 2.16-2.17 (m, 1H), 2.89-2.91 (m, 2H), 3.48-3.53 (m, 4H), 3.70-3.72 (m, 1H), 3.96-4.04 (m, 1H), 4.31-4.34 (m, 1H), 4.46-4.53 (m, 1H), 5.54 (d, J=10.3 Hz, 1H), 5.67 (d, J=10.3 Hz, 1H), 6.71 (s, 1H), 7.27-7.36 (m, 5H), 8.02-8.03 (m, 3H), 8.11-8.14 (m, 2H), 12.00 (s, 1H). mp: 140-141° C.

EXAMPLE 17

Preparation of (S)-5 fluorophenyl-2-((tert-butoxycarbonyl)amino)-4-methy-pentanoate (18)

Boc-L-leucine (1.17 g, 5 mmol) was dissolved in anhydrous tetrahydrofuran, followed by addition of pentafluorophenol (1.01 g, 5.5 mmol) and EDCI (1.05 g, 5.5 mmol), and the mixture was reacted at room temperature for 12 h.

Evaporated the solvent and its residue was separated by column chromatography to get colorless oil 18 (1.7 g, 86%).

EXAMPLE 18

Preparation of (S)-1-((2-(tert-butoxycarbonylamino)-4-methylvaleryl)oxy)urea (19)

Hydroxyurea (0.35 g, 4.3 mmol) was dissolved in DMF, followed by addition of 0.52 mL of N-Methylmorpholine and 18 (1.7 g, 4.3 mmol) was added dropwise in the reactant solution, then the mixture was reacted for 12 h at room temperature. Evaporated the solvent and its residue was separated by column chromatography to get white solid 19 (0.75 g, 60%).

EXAMPLE 19

Preparation of (S)-1-((2-amino-4-methylvaleryl)oxy)urea hydrochloride (20): 19

(0.75 g, 2.58 mmol) was dissolved in ethyl acetate solution saturated by chloride hydrogen, and let the solution react at room temperature for 2 h. Filtered it to get a white solid 20 (0.47 g, 81%).

EXAMPLE 20

Preparation of (2R,3S)-3-(tert-butoxycarbonylamino)-2-hydroxy-N—((S)-4-methylvaleryl)oxy)ureido)-4-phenylbutanamide (21)

Boc-AHPA (1 g, 3.38 mmol) was dissolved in anhydrous dichloromethane, followed by addition of EDCI (0.71 g, 3.72 mmol) and HOBt (0.5 g, 3.72 mmol), and after 0.5 h, 20 (0.84 g, 3.72 mmol) and 0.54 mL of triethylamine were added into the solution. The mixture was reacted for 5 h at room temperature after the ice bath was removed. Until the reaction was accomplished, evaporated the solvent and its residue was separated by column chromatography to obtain white solid 21 (0.71 g, 45%).

EXAMPLE 21

Preparation of (2S,3R)-3-amino-2-hydroxy-N—((S)-4-methylvaleryl)oxy)ureido)-4-phenylbutanamide hydrochloride (22)

21 (0.71 g, 1.52 mmol) was dissolved in ethyl acetate solution saturated by chloride hydrogen, and let the solution react at room temperature for 2 h. Filtered it to get a white solid 22 (0.48 g, 78%). ESI-MS m/z:367.3 (M+H)$^+$, $^1$H-NMR (600 MHz DMSO): δ 0.80-0.92 (m, 6H), 1.56-1.75 (m, 3H), 2.90-3.05 (m, 2H), 4.01-4.06 (m, 2H), 4.53 (m, 1H), 6.48-6.55 (m, 2H), 6.88 (s, 1H), 7.26-7.38 (m, 5H), 8.02-8.09 (m, 3H), 8.63 (d, J=7.2 Hz, 1H), 9.77 (m, 1H). mp: 110-112° C.

EXAMPLE 22

Preparation of Boc-Epirubicin (24)

23 (1.09 g, 2 mmol) was dissolved in anhydrous dichloromethane, followed by addition of 0.84 mL of trimethylamine and (Boc)$_2$O (0.52 g, 2.4 mmol) in dichloromethane solution was added into the mixture dropwise, the mixture was reacted overnight at room temperature until TLC test gave the reaction was accomplished. After the reaction was accomplished, the reactant solution was washed with 10% citric acid and saturated NaCl for 3 times, dried with anhydrous sodium sulfate. Filtered it and evaporated the solvent to get compound 24 (1.09 g, 85%).

EXAMPLE 23

Preparation of (S)-2-((2S,4S)-4-((2S,4S,5R,6S)-4-((tert-butoxycarbonyl)amino)-5-hydroxy-6-methyl-2(2H)-tetrahydropyranyloxy)-2,5,12-trihydroxy-7-methoxy-6,11-dioxo-2-(1,2,3,4,6,11-hexahydrotetracenyl))-2-ethoxy-2-(benzyloxycarbonylamino)-4-methylpentanoate (25)

Cbz-L-leucine (0.5 g, 1.87 mmol) was dissolved in anhydrous dichloromethane, followed by addition of EDCI (0.36 g, 1.87 mmol) and HOBt (0.25 g, 1.87 mmol) under ice bath, and after 0.5 h, 24 (1.09 g, 1.7 mmol) was added into the solution. The mixture was reacted for 5 h at room temperature after the ice bath was removed. Until the reaction was accomplished, evaporated the solvent and its residue was separated by column chromatography to obtain white solid 25 (0.76 g, 50%).

EXAMPLE 24

Preparation of (S)-2-((2S,4S)-4-((2S,4S,5R,6S)-4-((tert-butoxycarbonyl)amino)-5-hydroxy-6-methy-2(2H)-tetrahydropyranyloxy)-2,5,12-trihydroxy-7-methoxy-6,11-dioxo-2-(1,2,3,4,6,11-hexahydrotetracenyl))-2-ethoxy-2-amino-4-methylpentanoate (26)

25 (0.76 g, 0.85 mmol) was dissolved in methanol, then 0.1 g Pd/C (10%) was added in several times. The air in the reactant bottle was removed out and was filled with hydrogen by a hydrogen balloon, after being reacted for 12 h, filtered the mixture with two layers of filter papers. The solvent was evaporated until the residue was dried to get colorless foam like solid 26 (0.6 g, 93.0%).

EXAMPLE 25

Preparation of (S)-2-((2S,4S)-4-((2S,4S,5R,6S)-4-((tert-butoxycarbonyl)amino)-5-hydroxy-6-methyl-2(2H)-tetrahydropyranyloxy)-2,5,12-trihydroxy-7-methoxy-6,11-dioxo-2-(1,2,3,4,6,11-hexahydrotetracenyl))-2-ethoxy-2-42S,3R)-3-((tert-butoxycarbonyl)amino)-2-hydroxy-4-phenylbutyryl)-4-methylpentanoate (27)

Boc-AHPA (0.27 g, 0.88 mmol) was dissolved in anhydrous dichloromethane followed by addition of EDCI (0.17 g, 0.88 mmol) and HOBt (0.27 g, 0.88 mmol) under ice bath, and after 0.5 h, 26 (0.6 g, 0.8 mmol) was added into the solution. The mixture was reacted for 5 h at room temperature after the ice bath was removed. Until the reaction was accomplished, evaporated the solvent and its residue was separated by column chromatography to obtain white solid 27 (0.47 g, 57%).

EXAMPLE 26

Preparation of (S)-2-((2S,4S)-4-((2S,4S,5R,6S)-4-((tert-butoxycarbonyl)amino)-5-hydroxy-6-methyl-2(2H)-tetrahydropyranyloxy))-2,5,12-trihydroxy-7-methoxy-6,11-dioxo-2-(1,2,3,4,6,11-hexahydrotetracenyl)-2-ethoxy-2-((2S,3R)-3-amino-2-hydroxy-4-phenylbutyryl)-4-methylpentanoate hydrochloride (28)

27 (0.47 g, 0.46 mmol) was dissolved in ethyl acetate solution saturated by chloride hydrogen, and let the solution react at room temperature for 2 h. Filtered it to get white solid 28 (0.36 g, 87%). ESI-MS m/z:833.7 (M+H)$^+$, $^1$H-NMR (600 MHz DMSO): δ 0.81-0.94 (m, 6H), 1.23 (d, J=7.2 Hz, 3H), 1.58-1.83 (m, 3H), 1.75-1.79 (m, 1H), 2.07-2.09 (m, 1H), 2.20-2.24 (m, 2H), 2.93-3.18 (m, 4H), 3.44-3.49 (m, 2H), 3.88 (s, 3H), 3.98 (t, J=5.4 Hz, 1H), 4.06-4.09 (m, 2H), 4.55 (m, 1H), 4.58-4.69 (m, 2H), 4.91-4.98 (m, 2H), 5.05-5.09 (m, 1H), 5.28-5.35 (m, 1H), 5.47 (s, 1H), 5.76 (s, 1H), 6.93 (s, 1H), 7.26-7.38 (m, 5H), 7.69 (m, 1H), 7.91-7.98 (m, 2H), 8.11-8.19 (m, 3H), 8.63 (d, J=7.2 Hz, 1H). mp: 136-138° C.

EXAMPLE 27

Preparation of (S)-2-(4-(6-(5-(2-chloro-6-methylphenyl)-2-thiazolylcarbonyl amino)-2-methyl-4-pyrimidinyl)-1-piperazinyl)ethyl-2-(tert-butoxycarbonylamino)-4-methylpentanoate (29)

Boc-L-leucine (0.25 g, 1.1 mmol) was dissolved in anhydrous dichloromethane, followed by addition of EDCI (0.21 g, 1.1 mmol) and HOBt (0.15 g, 1.1 mmol) under ice bath, and after 0.5 h, Dasatinib (0.51 g, 1 mmol) and 0.2 mL of triethylamine were added into the solution. The mixture was reacted for 5 h at room temperature after the ice bath was removed. After the reaction was accomplished, the organic layer was washed with water, 1 M citric acid, saturated sodium bicarbonate and saturated sodium chloride solution respectively, then dried with anhydrous sodium sulfate, filtered it and evaporated the solvent to get white solid 29 (0.28 g, 40%).

EXAMPLE 28

Preparation of (S)-2-(4-(6-(5-(2-chloro-6-methylphenyl)-2-thiazolylcarbonyl amino)-2-methyl-4-pyrimidinyl)-1-piperazinyl)ethyl-2-amino-4-methylpentanoae hydrochloride (30)

29 (0.7 g, 1 mmol) was dissolved in ethyl acetate solution saturated by chloride hydrogen, and let the solution react at room temperature for 2 h. Filtered it to get white solid 30 (0.54 g, 80%).

EXAMPLE 29

Preparation of (S)-2-(4-(6-(5-((2-chloro-6-methylphenyl)-2-thiazolylcarbonyl amino)-2-methyl-4-pyrimidinyl)-1-piperazinyl)ethyl-2-((2S,3R)-3-((tert-butoxycarbonyl)amino)-2-hydroxy-4-phenylbutyryl)-4-methylpentanoate (31)

Boc-AHPA (0.16 g, 0.55 mmol) was dissolved in anhydrous dichloromethane, followed by addition of EDCI (0.11 g, 0.55 mmol) and HOBt (0.08 g, 0.55 mmol) under ice bath, and after 0.5 h, 30 (0.34 g, 0.5 mmol) was added into the solution. The mixture was reacted for 5 h at room temperature after the ice bath was removed. Until the reaction was accomplished, evaporated the solvent and its residue was separated by column chromatography to obtain white solid 31 (0.22 g, 51%).

EXAMPLE 30

Preparation of (S)-2-(4-(6-(5-(2-chloro-6-methylphenyl)-2-thiazolylcarbonyl amino)-2-methyl-4-pyrimidinyl)-1-piperazinyl)ethyl-2-((2S,3R)-3-amino-2-hydroxy-4-phenylbutyryl)-4-methylpentanoate hydrochloride (32)

31 (0.22 g, 0.25 mmol) was dissolved in ethyl acetate solution saturated by chloride hydrogen, and let the solution react at room temperature for 2 h. Filtered it to get white solid 32 (0.18 g, 84%). ESI-MS m/z:777.5 (M+H)$^+$, $^1$H-NMR (600 MHz DMSO): δ 0.83-0.95 (m, 6H), 1.59-1.85 (m, 3H), 2.13 (s, 3H), 2.26 (s, 3H), 2.54-2.58 (m, 6H), 2.90-3.05 (m, 2H), 3.60-3.70 (m, 6H), 4.01-4.06 (m, 2H), 4.53-4.58 (m, 1H), 6.09 (s, 1H), 6.88 (s, 1H), 7.26-7.38 (m, 7H), 7.48 (d, J=7.2 Hz, 1H), 8.02-8.09 (m, 3H), 8.22 (s, 1H), 8.63 (d, J=7.2 Hz, 1H), 9.57-9.59 (m, 2H), 9.77-9.78 (m, 2H). mp: 174-176° C.

EXAMPLE 31

Inhibition Activity Against Enzyme In Vitro

1: Materials and Methods

Aminopeptidase N and L-Leu-p-nitroanilide as substrate were purchased from Sigma cooperation.

Preparation of Buffer Solution: 12.89 g Na$_2$HPO$_4$.12H$_2$O and 2.18 g NaH$_2$PO$_4$.2H$_2$O were dissolved in a 1000 mL volumetric flask, then the mixture was diluted to 1000 mL with fresh distilled water to obtain 50 mM Phosphate Buffer solution (PBS, pH 7.2), which was kept at room temperature to spare.

Aminopeptidase N was dissolved in the buffer solution to obtain 0.1 IU/mL solution.

The substrate was dissolved in DMSO to obtain a 16 mmol/mL solution, which was kept in refrigerator to spare.

2: Experimental Procedure

| No. | Aminopeptidase N solution (μL) | substrate solution (μL) | buffer solution (μL) | Inhibitor |
|---|---|---|---|---|
| 100% control group | 10 | 5 | 185 | 0 |
| Blank control group | 0 | 5 | 195 | 0 |
| Inhibitor group | 10 | 5 | 145 | 40 |

The aminopeptidase N solution 10 μL, the substrate solution 5 μL and compound with different concentration 40 μL were added into a 96-well cell plate, and then adjusted to 200 μL with phosphate buffer saline solution (pH 7.2). 100% group did not include inhibitor. And the substrate solution 5 μL of blank group was adjusted to 200 μL with buffer solution. The mixture was incubated at 37° C. for 0.5 h, and absorbance was then determined at 405 nm wavelength Inhibitory ratio can be calculated as follows:

Inhibitory ratio (%) =

$$\frac{\text{absorbance of 100\%} - \text{absorbance of compound}}{\text{absorbance of 100\%} - \text{absorbance of blank group}} \times 100\%$$

According to concentration of compound and corresponding inhibitory ratio, the $IC_{50}$ value was calculated by using a fitting curve of Origin 7.5 software.

3: Experimental Results:

The inhibition activity against aminopeptidase N of the compound represented by formula (I) of the present invention and ubenimex as positive control drug are shown in the following table:

| Compd(compound) | $IC_{50}(\mu M)$ APN |
|---|---|
| 6(BC-01) | 6.98 |
| 16(BC-02) | 0.38 |
| BC-03 | 0.36 |
| BC-04 | 1.30 |
| BC-05 | 1.39 |
| BC-06 | 4.66 |
| BC-07 | 0.15 |
| 22 | 2.92 |
| 28 | 5.56 |
| 32 | 7.88 |
| ubenimex | 5.12 |

The result of inhibition activity against enzyme in vitro showed that, the target compounds BC-01, BC-02, BC-03, BC-04, BC-05, BC-06, BC-07, 22, 28 and 32 represented by formula (I) of the present invention all established an inhibitory activity against aminopeptidase N, wherein Compounds BC-02, BC-03, BC-04, BC-05, BC-06 and BC-07 were much more potent than the positive control drug ubenimex, especially, BC-07 showed great activity with 0.15 μM. Compounds BC-01, 22, 28 and 32 showed a comparable activity with ubenimex. This indicated that synergetic fragment linked at carboxyl group of ubenimex may increase its activity against enzyme without destroying inhibition activity against enzyme of the whole structure.

EXAMPLE 32

Pharmacodynamic Experiment In Vitro (MTT Method)

Human leukemia cell line K562, clear-cell ovarian carcinoma cell line ES-2, human prostate cancer cell line PC-3, human breast cancer cell line MCF-7, cell line Hela, human liver cancer cell line H7402 and human ovarian cancer cell line 3-AO were transferred into a culture flask and were cultured in a medium at 37° C. in a 5% $CO_2$ and saturation humidity. One bottle of cells in logarithmic growth phase was picked out and was blew and beaten to be uniform with a pipette, then took some cell suspension solution to prepare blood counting plate smear to count cells under inverted microscope, and then adjusted the cell number to be $1 \times 10^5$/mL by adding some culture medium. Cells were seeded on a 96-well plate on which also drug tests performed. Blank control group, negative control group, positive control group and drug test group were established on the plate while the surrounding wells of the plate were not used (but filled with sterile PBS), wherein the blank control groups were prepared by addition of culture medium 150 μL per well, the negative control groups were prepared by addition of cell suspension solution 100 μL per well and culture medium 50 μL per well, the positive control groups were prepared by addition of cell suspension solution 100 μL per well and positive control drug solution 50 μL per well, the drug test groups were prepared by addition of cell suspension solution 100 μL per well and test compound solution 50 μL per well, and there were 5 different concentrations of drug in the positive control group and the drug test group respectively: 0.01, 0.1, 1, 10, 100 $\mu mol \cdot L^{-1}$, each concentration was established with 3 parallel wells. After the drug was added, the 96-well plate was incubated for 48 h at 37° C. in a $CO_2$ incubator of 5% $CO_2$ and saturation humidity. Upon completion of the incubation, 20 μL MTT solution (concentration was 5 mg/mL) was added to each well and incubated for an additional 4 h, and after the 96-well plate was centrifuged at 2000 rpm for 30 min, medium of each well was suck out carefully and removed and 100 μL DMSO was added instead, followed by vibrating on a tablet shaker for 15 min to re-dissolve formazan crystals completely. OD value of each well was measured at 570 nm wavelength using an enzyme-linked immunosorbent assay reader to calculate cellular proliferation inhibitory ratio of each drug in different concentrations. And half-inhibitory concentration ($IC_{50}$) was calculated using statistical software SPSS 16.0, wherein the cellular proliferation inhibitory ratio can be calculated as following equation:

$$\text{cellular proliferation inhibitory ratio} = \frac{\text{OD mean value in well of negative control} - \text{OD mean value in well of drug test}}{\text{OD mean value in well of negative control} - \text{OD mean value in well of blank control}} \times 100\%$$

The results of proliferation inhibition activity of target compounds BC-01, BC-02, 22, 28, 32 and positive control drugs ubenimex and 5-fluorouracil (5-FU) against clear-cell ovarian carcinoma cell line ES-2, human leukemia cell line K562, human prostate cancer cell line PC-3, human breast cancer cell line MCF-7, cell line Hela, human liver cancer cell line H7402 and human ovarian cancer cell line 3-AO are shown in following table:

| Compd | $EC_{50}$ (μM) | | | | | | |
|---|---|---|---|---|---|---|---|
| | ES-2 | K562 | PC-3 | MCF-7 | Hela | H7402 | 3-AO |
| 6(BC-01) | 2.53 | 5.82 | 10.71 | 1.35 | 0.73 | 1.86 | 2.59 |
| BC-02 | 1.34 | ND | 3.45 | ND | ND | 10.98 | ND |
| 22 | 5.66 | 6.52 | 13.34 | 6.74 | 5.55 | 7.98 | 9.06 |
| 28 | 3.34 | 4.35 | 7.67 | 2.55 | 1.99 | 4.02 | 3.02 |

| Compd | EC$_{50}$ (μM) | | | | | | |
|---|---|---|---|---|---|---|---|
| | ES-2 | K562 | PC-3 | MCF-7 | Hela | H7402 | 3-AO |
| 32 | 6.45 | 6.33 | 14.13 | 3.65 | 3.23 | 6.75 | 4.89 |
| 5-FU | ND | 16.03 | 15.70 | 76.92 | 132.99 | 385.38 | 60.81 |
| Uubenimex | >400 | >400 | >400 | 32.70 | 79.59 | 188.54 | >400 |

ND: not determined.

The results of bioactivities showed that, the target compounds BC-01, BC-02, 22, 28 and 32 represented by formula (I) of the present invention established an obvious anti-proliferation effect against all the tumor cells above. By comparing with the positive drugs ubenimex and 5-fluorouracil (5-FU), BC-01 showed much higher proliferation inhibition activity against cell line Hela, and had an obvious proliferation inhibition activity against clear-cell ovarian carcinoma cell line ES-2, human leukemia cell line K562, human prostate cancer cell line PC-3, human breast cancer cell line MCF-7, human liver cancer cell line H7402 and human ovarian cancer cell line 3-AO as well; BC-02 established a great proliferation inhibition activity against clear-cell ovarian carcinoma ES-2 cell line. Compounds 22, 28 and 32 were much more potent than 5-FU on proliferation inhibition activity.

The results of cells test in vitro showed that, the target compounds BC-01, BC-02, 22, 28 and 32 represented a great proliferation inhibition activity against 7 cell lines.

EXAMPLE 33

Inhibition Assay of the Target Compounds Against Liver Cancer H22

1: Establishment of Transplanting Tumor Bearing Mice Models

Extracted the ascites from H22 ascites tumour bearing mice, washed the ascites with sterile PBS for three times and then resuspended the cells with sterile PBS (cells counts: 3.75×10$^7$ cells/mL), inoculated it into right oxter of Kunming mice 100 uL per mouse. After getting rid of the Kunming mice overweight or underweight, the tumor-bearing mice were randomized to several groups, and then the mice was began to administrate drug based on administration strategy, henceforth administrated once a day with two days off when having administrated for 5 days until two cycles one of which had 7 days (the volume of administration was: 200 uL/20 g once per mouse, the method of administration was: oral gavage). The body weight of mouse was recorded at the beginning and ending of every cycle, and the average volume of administration was 200 uL/20 g once per mouse; the method of administration was: oral gavage, and administrated once a day.

2: Pharmacodynamic Experiment 2.1 Inhibition Assay of Oral Administration Against Liver Cancer H22

The H22 tumor bearing mice were randomized to 4 groups (10 mice per group) after being weighted. (1) the negative control: PBS; (2) Xeloda group: 100 mg/kg/d; (3) TFU group: 70 mg/kg/d; (4) BC-01 group: 100 mg/kg/d. And administrated once a day with two days off when having administrated for 5 days until two cycles one of which had 7 days (the volume of administration was: 200 uL/20 g once per mouse, the method of administration was: oral gavage). The size of tumor was measured by using a vernier calliper and weight of mouse by using an electronic balance at the beginning and ending of every cycle, then calculated their mean value. The mice were sacrificed after 13 days and the tumors were taken out and weighted. Tumor volume and inhibitory ratio were calculated as the following equation (L and W referred to length and width of tumor respectively):

$$\text{Tumor volume} = \frac{1}{2}LW^2$$

Inhibitory ratio of tumor weight (100%) =

$$\left(1 - \frac{\text{mean tumor weight of test group}}{\text{mean tumor weight of control group}}\right) \times 100\%$$

Inhibitory ratio of tumor volume (100%) =

$$\left(1 - \frac{\text{mean tumor volume of test group}}{\text{mean tumor volume of control group}}\right) \times 100\%$$

2.2: Inhibition Assay of Intravenous Administration Against Liver Cancer H22

The H22 tumor-bearing mice were randomized to 4 groups (7 mice per group) after being weighted. (1) the negative control: PBS; (2) 5-FU group: 20 mg/kg/d; (3) BC-01 group: 50 mg/kg/d; (4) BC-01 group: 70 mg/kg/d; (5) BC-02 group: 70 mg/kg/d; (6) combination group of ubenimex and 5-FU: 5-FU: 15 mg/kg/d (intravenous injection), ubenimex: 30 mg/kg/d (oral administration). And administrated once a day with two days off when having administrated for 5 days until two cycles one of which had 7 days (the volume of administration was: 200 uL/20 g once per mouse, the method of administration was: tail intravenous injection). The size of tumor was measured by using a vernier calliper and weight of mouse by using an electronic balance at the beginning and ending of every cycle, then calculated their mean value. The mice were sacrificed after 13 days and the tumors were taken out and weighted. Tumor volume and inhibitory ratio were calculated as the following equation (L and W referred to length and width of tumor respectively):

$$\text{Tumor volume} = \frac{1}{2}LW^2$$

Inhibitory ratio of tumor weight (100%) =

$$\left(1 - \frac{\text{mean tumor weight of test group}}{\text{mean tumor weight of control group}}\right) \times 100\%$$

Inhibitory ratio of tumor volume (100%) =

$$\left(1 - \frac{\text{mean tumor volume of test group}}{\text{mean tumor volume of control group}}\right) \times 100\%$$

Figure 3:
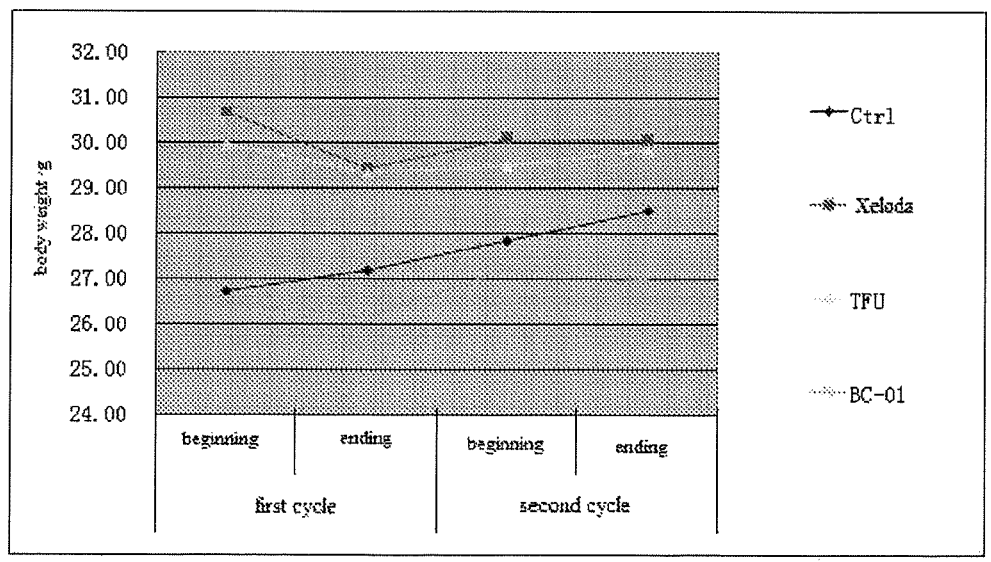
FIG. 3 illustrates the body weight changing curve of Kunming mice by oral administration.
Figure 4:
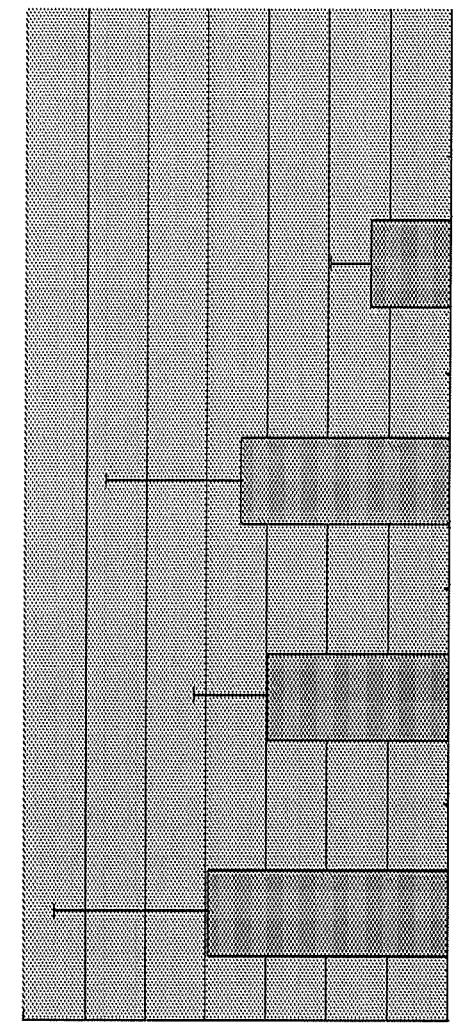
FIG. 4 illustrates the tumor weight of Kunming mice by oral administration.
Figure 5:
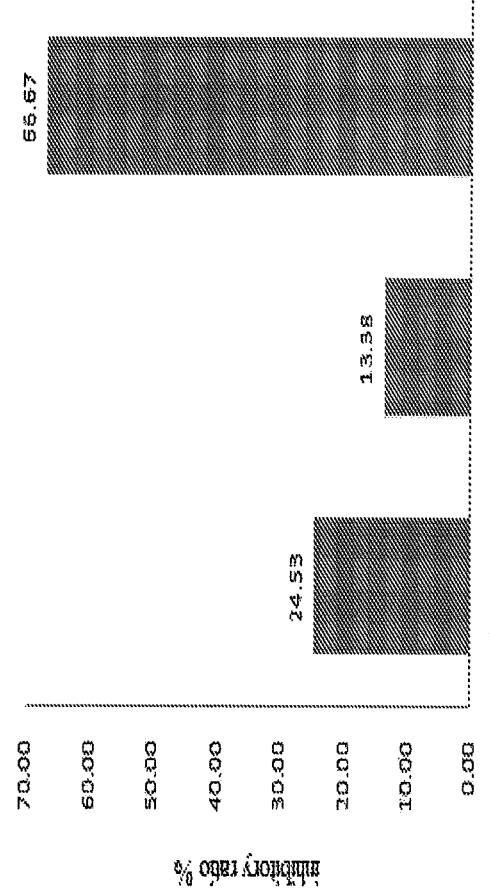
FIG. 5 illustrates the tumor inhibitory ratio of compounds by oral administration.
Figure 6:
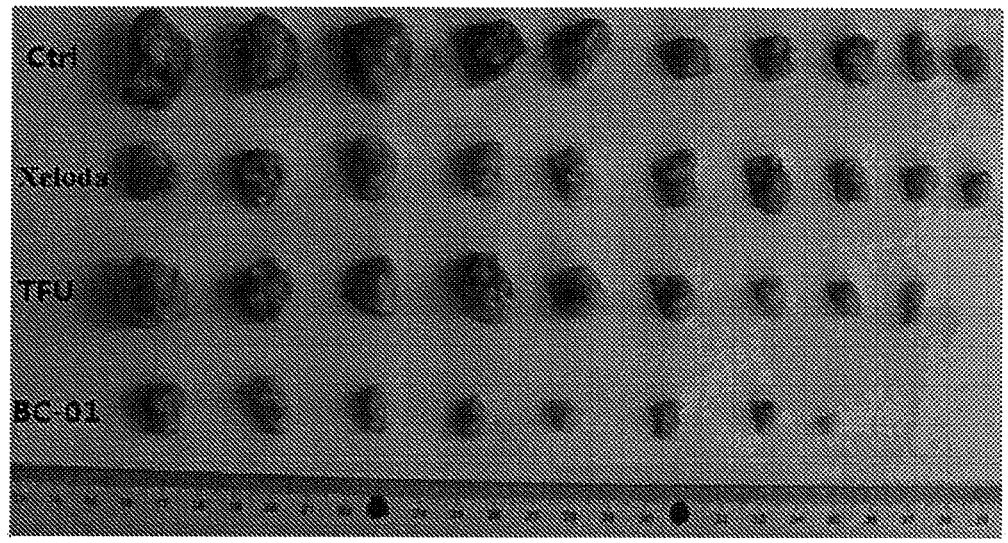
FIG. 6 illustrates the photographs of tumors of every groups by oral administration.

3: Experimental Results
3.1: Experimental Results of Inhibition Assay of Oral Administration Against Liver Cancer H22 (Shown in FIGS. 3, 4, 5 and 6)

|  | Ctrl (control group) | Xeloda | TFU | BC-01 |
|---|---|---|---|---|
| tumor weight | 0.79 | 0.60 | 0.68 | 0.26 |
| SD | 0.52 | 0.25 | 0.45 | 0.13 |
| inhibitory ratio (%) |  | 24.53 | 13.38 | 66.67 |

Figure 7:
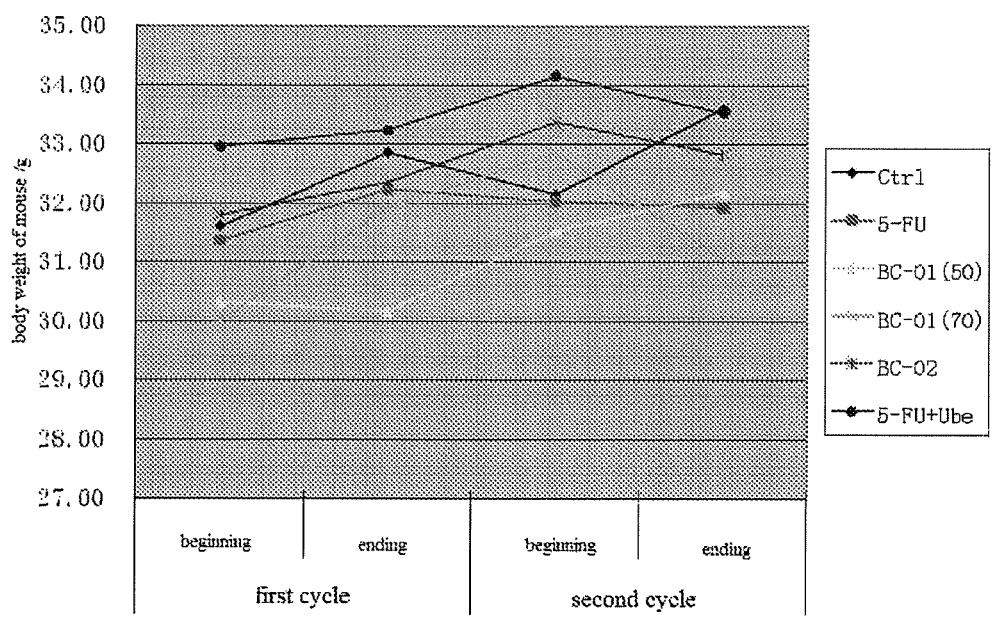
FIG. 7 illustrates the body weight changing curve of Kunming mice by intravenous injection.
Figure 8:
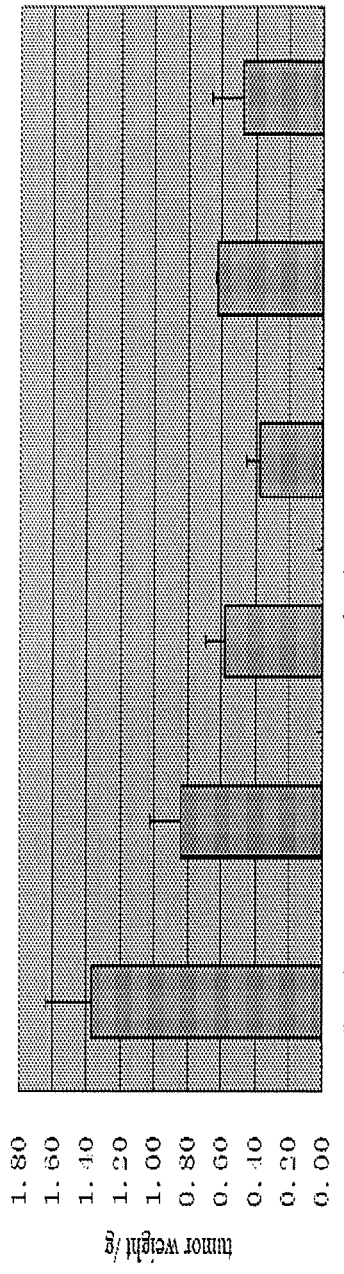
FIG. 8 illustrates the tumor weight of Kunming mice by intravenous injection.
Figure 9:
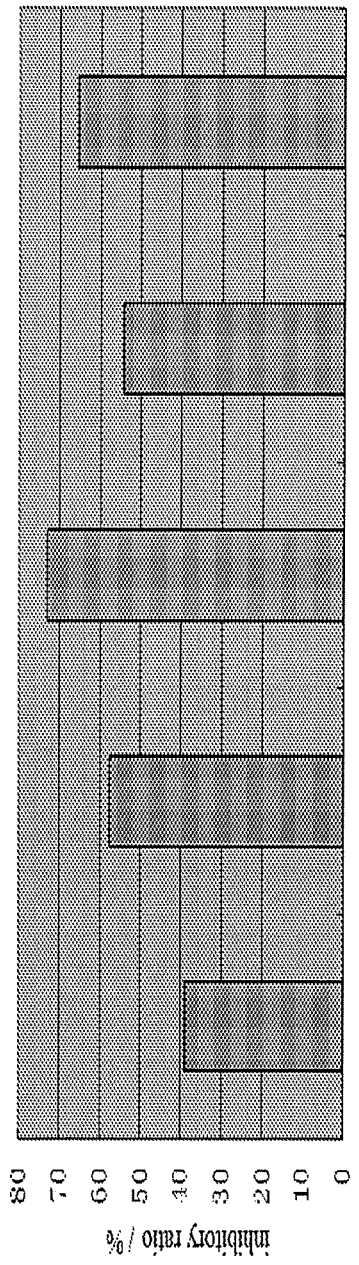
FIG. 9 illustrates the tumor inhibitory ratio of compounds by intravenous injection.
Figure 10:
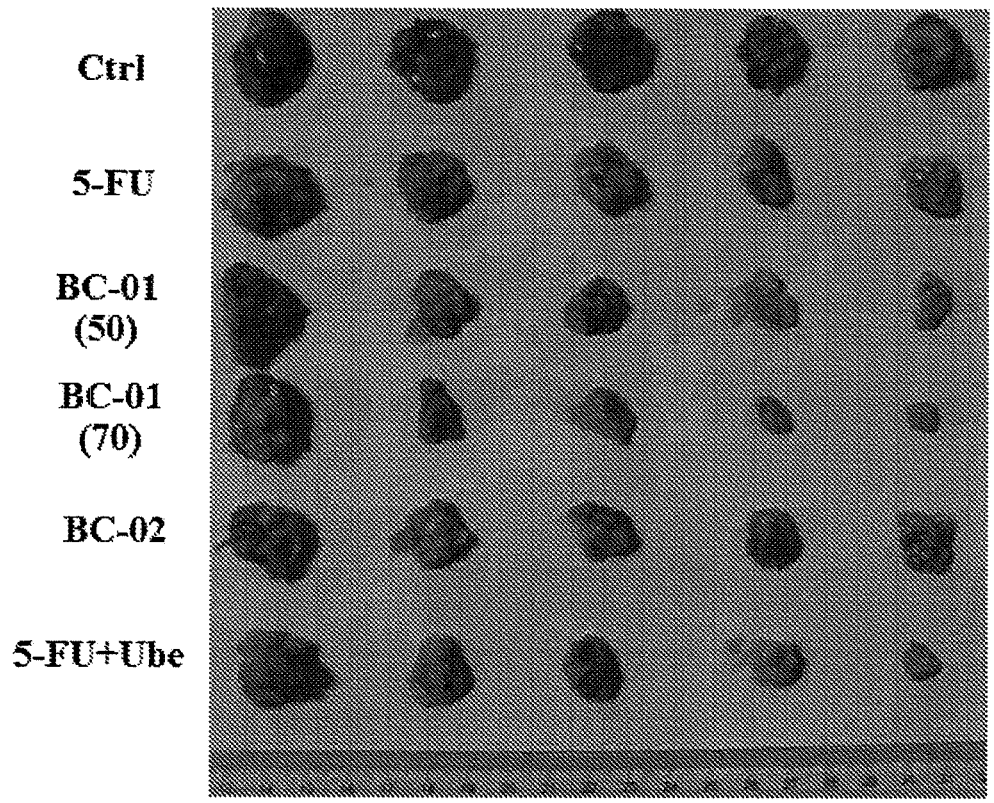
FIG. 10 illustrates the photographs of tumors of every groups by intravenous injection.

3.2: Experimental Results of Inhibition Assay of Intravenous Administration Against Liver Cancer H22 (Shown in FIGS. 7, 8, 9 and 10)

| Compd | Number of mice alive | Body weight(g) beginning(g) | Body weight(g) ending(g) | Tumor weight(g) | inhibitory ratio (%) |
|---|---|---|---|---|---|
| Ctrl(control group) | 7 | 31.60 ± 4.33 | 33.61 ± 4.21 | 1.37 ± 0.27 | |
| 5-FU | 7 | 31.37 ± 4.05 | 31.92 ± 4.98 | 0.84 ± 0.19 | 38.83 |
| BC-01(50) | 7 | 30.32 ± 1.57 | 31.53 ± 4.71 | 0.58 ± 0.12 | 57.66 |
| BC-01(70) | 7 | 30.00 ± 1.15 | 31.05 ± 1.78 | 0.37 ± 0.08 | 73.00 |
| BC-02 | 7 | 31.81 ± 4.99 | 32.83 ± 4.64 | 0.63 ± 0.01 | 54.31 |
| 5-FU + Bes | 7 | 32.96 ± 1.75 | 34.54 ± 1.18 | 0.47 ± 0.19 | 65.55 |

EXAMPLE 34

Evaluation of Activities of Compounds in H22 Tumor Cells Bearing Kunming Mice Models 1. Grouping and Dosage:

| Group | Administration dosage | Method of administration | Number of mice |
|---|---|---|---|
| Ctrl group | Equivalent PBS solution | Intravenous injection | 8 |
| Xeloda | 108 mg/kg/d (0.3 mmol/kg/d) | Oral gavage | 8 |
| BC-01 | 120 mg/kg/d (0.25 mmol/kg/d) | Oral gavage | 8 |
| BC-02 | 130 mg/kg/d (0.25 mmol/kg/d) | Oral gavage | 8 |
| 5-FU | 20 mg/kg/d (0.15 mmol/kg/d) | Intravenous injection | 8 |
| BC-01 | 50 mg/kg/d (0.1 mmol/kg/d) | Intravenous injection | 8 |
| BC-07 | 58.3 mg/kg/d (0.1 mmol/kg/d) | Intravenous injection | 8 |
| BC-02 | 55 mg/kg/d (0.1 mmol/kg/d) | Intravenous injection | 8 |
| BC-02 | 79 mg/kg/d (0.15 mmol/kg/d) | Intravenous injection | 8 |

Wherein, d represents day.

2. Experimental Procedure

The ascites was extracted from H22 tumour bearing mice with well growth, followed by adding sterile PBS to dilute the ascites to a concentration of $8.5 \times 10^7$ cells/mL. 100 uL of the cells solution was suck up by a 1 mL sterile injector to inoculate into right oxter of mice. After 3 days, the mice were weighted and randomized to several groups (almost 8 mice per group, and a bit more in control group). These mice were administrated a predetermined dosage by intravenous or oral gavage with two days off when having administrated for 5 days until two cycles one of which had 7 days. The body weight of mouse was recorded at the beginning and ending of every cycle, After being administrated for two cycles, the mice were weighted and recorded, then sacrificed by cervical dislocation to get lung, liver and spleen weighted respectively.

Overall difference was calculated by the function of one-way analysis of variance (One-Way ANOVA) in Origin 7.5 software; and t-test was used for pair-comparison between drug administrated group and blank group, and the inhibitory ratio of drug in each group was calculated based on the following equation: inhibitory ratio (100%)=(mean tumor weight of control group−mean tumor weight of drug administrated group)/mean tumor weight of control group× 100.

Figure 11:
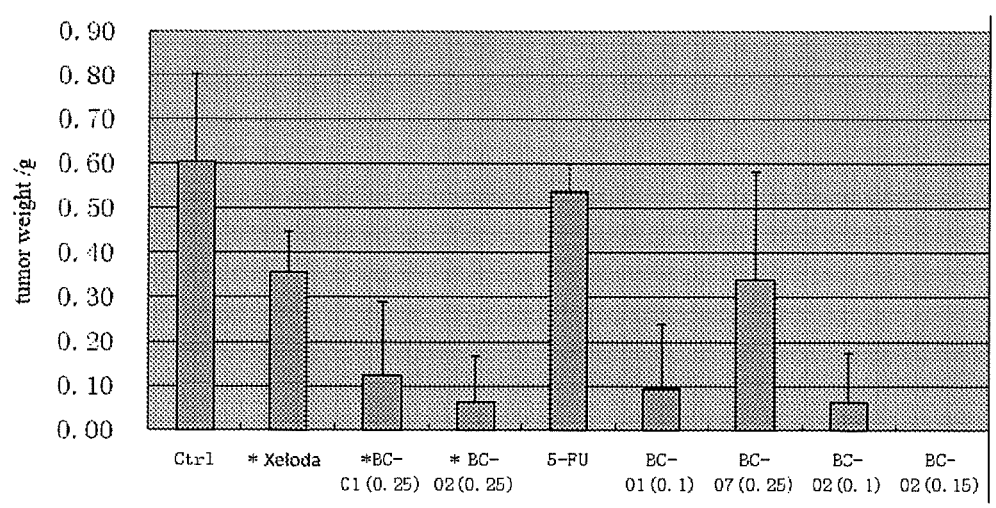
FIG. 11 illustrates the tumor weight and its deviation, wherein, *signed groups were treated by oral gavage, the other were treated by tail intravenous injection.
Figure 12:
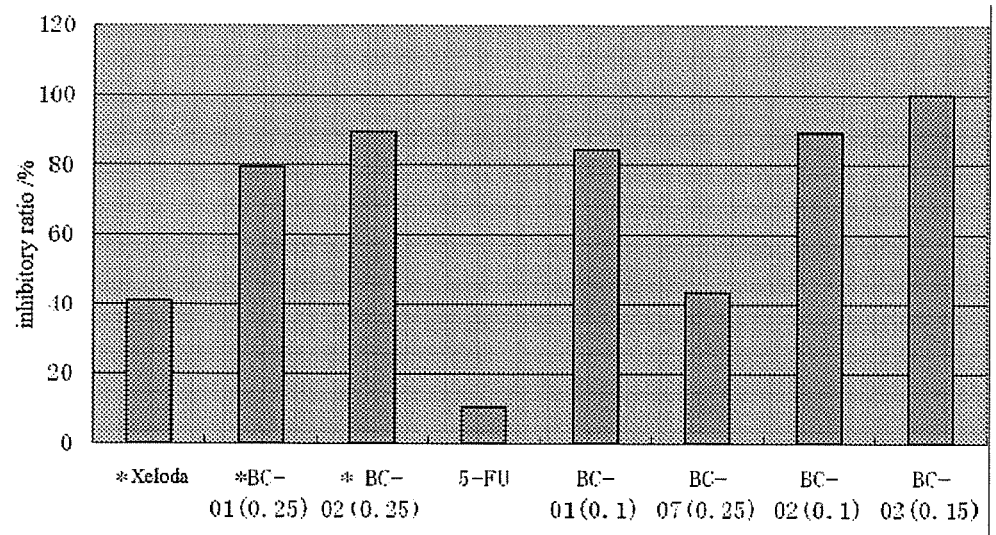
FIG. 12 illustrates the inhibitory ratio of compounds, wherein, *signed groups were treated by oral gavage, the other were treated by tail intravenous injection.
Figure 13:
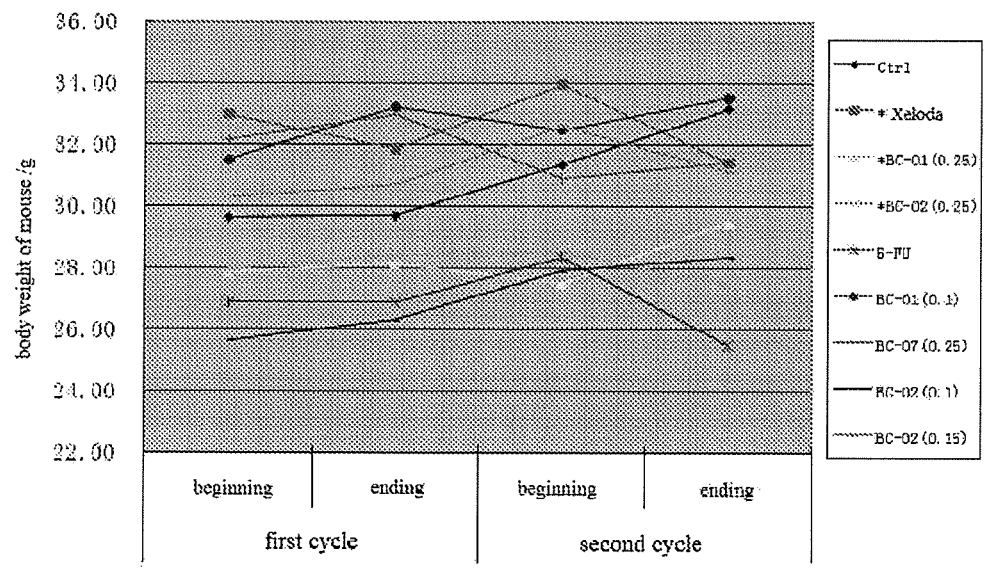
FIG. 13 illustrates animal weight changing curve, wherein, *signed groups were treated by oral gavage, the other were treated by tail intravenous injection.
Figure 14:
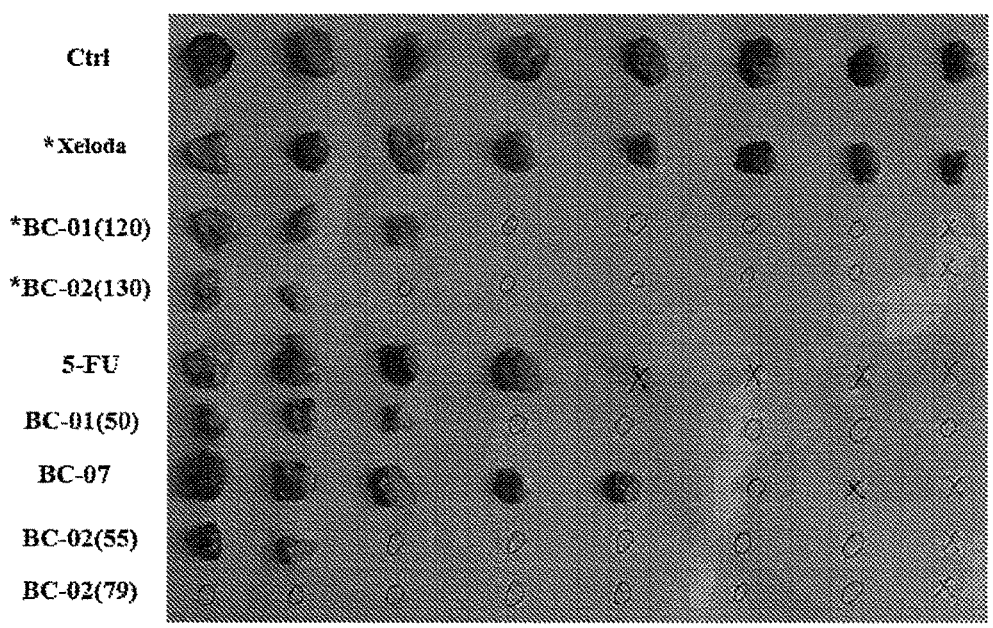
FIG. 14 illustrates the photographs of tumors obtained in experiments, wherein, *signed groups were treated by oral gavage, the other were treated by intravenous injection, besides, the "O" means no tumor detected, while the "X" means animal dead.

3. Experimental Results (Shown in FIGS. 11, 12, 13 and 14)

| Groups | Number of mice alive | Body weight(g) Beginning(g) | Body weight(g) Ending(g) | Tumor weight (g) | Tumor growth inhibition (%) |
|---|---|---|---|---|---|
| Ctrl group | 8 | 29.66 ± 3.60 | 31.37 ± 4.97 | 0.60 ± 0.20 | |
| *Xeloda | 7 | 33.00 ± 1.81 | 31.42 ± 3.56 | 0.35 ± 0.09 | 40.95 |
| *BC-01(50) | 7 | 27.87 ± 2.55 | 29.50 ± 2.15 | 0.12 ± 0.16 | 79.52 |
| *BC-02(70) | 7 | 27.98 ± 3.73 | 27.49 ± 4.94 | 0.06 ± 0.11 | 89.76 |
| 5-FU | 4 | 26.89 ± 2.06 | 25.51 ± 4.50 | 0.54 ± 0.06 | 10.41 |
| BC-01(50) | 8 | 31.52 ± 3.63 | 31.78 ± 5.76 | 0.09 ± 0.14 | 84.38 |
| BC-07 | 6 | 32.17 ± 3.86 | 31.44 ± 5.01 | 0.34 ± 0.24 | 43.61 |
| BC-02 | 7 | 25.67 ± 2.62 | 28.35 ± 3.71 | 0.06 ± 0.11 | 89.52 |
| BC-02 | 7 | 30.32 ± 4.42 | 31.13 ± 3.55 | 0.0 ± 0.0 | 100 |

In this table, *signed groups were treated by oral gavage

As observed in FIGS. 11-14, compounds BC-01 and BC-02 all showed excellent anti-tumor growth activity, what's more, at a dosage of 0.15 mmol/kg/d of intravenous administrated BC-02, no tumor appeared until the end of the experiment.

At the end of experiments, there is no significant changes in visceral organs by visual observation of dissected mice, it indicates that compounds at administration dosage have no evident toxicity.

What is the claimed is:

1. A multi-targeted Ubenimex pro-drug derivative represented by general structural formula (I), as well as an enantiomer, a diastereoisomer, a racemate or a pharmaceutically acceptable salt or solvate thereof:

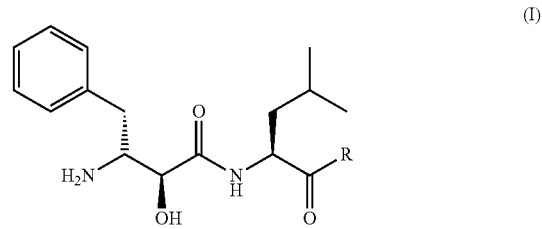

(I)

wherein, R is selected from:

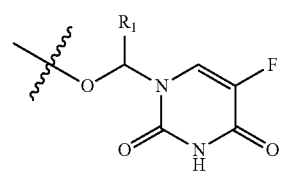

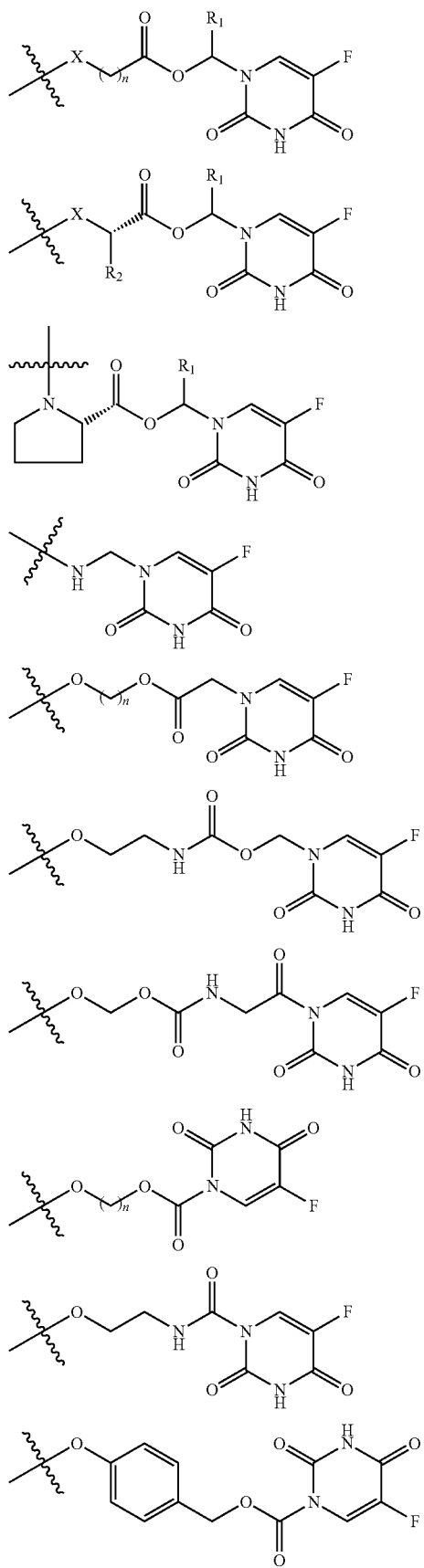

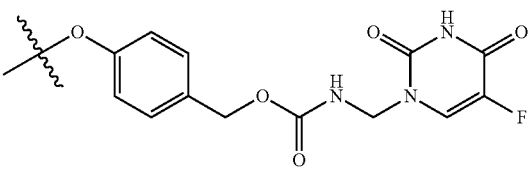

wherein n is 1-6; wherein X is NH or O; wherein $R_1$ is H, $CH_3$ or $CH_2CH_3$; and wherein $R_2$ is selected from H, $CH_3$, $CH_2CH_3$, $CH(CH_3)_2$, $CH_2CH(CH_3)_2$, $CH_3CH_2CH(CH_3)$, $CH_2OH$, $CH_3CH(OH)$, $CH_3SCH_2CH_2$, $CH_2Ph$, or OH-p-PhCH_2.

2. The multi-targeted Ubenimex pro-drug derivative according to claim 1, wherein R is:

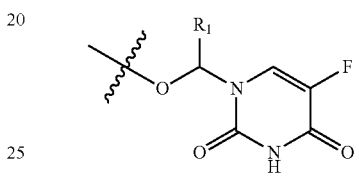

wherein, $R_1$ is H, $CH_3$ or $CH_2CH_3$.

3. The multi-targeted Ubenimex pro-drug derivative according to claim 1, R is selected from:

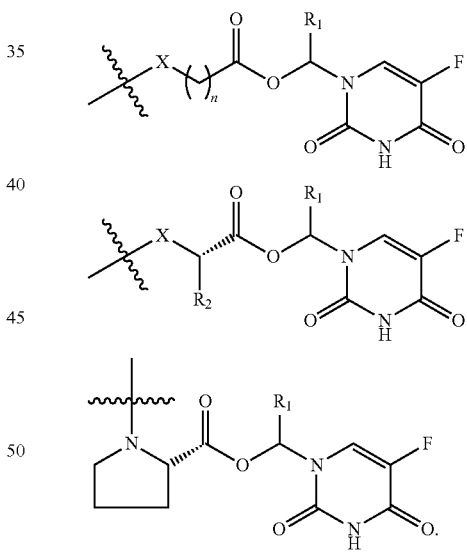

4. The multi-targeted Ubenimex pro-drug derivative according to claim 1, wherein R is selected from:

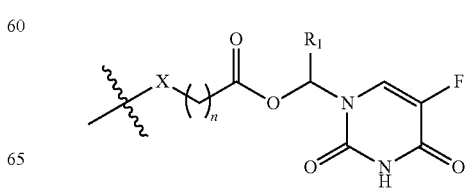

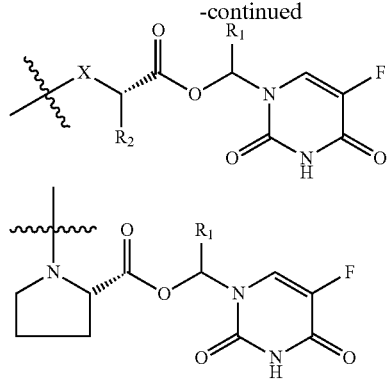
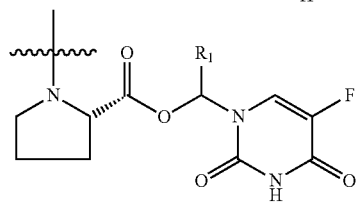
wherein n is 1-6.
* * * * *